US007579152B2

(12) United States Patent
Yeh

(10) Patent No.: US 7,579,152 B2
(45) Date of Patent: Aug. 25, 2009

(54) SENP1 AS A MARKER OF CANCER DEVELOPMENT AND TARGET FOR CANCER THERAPY

(75) Inventor: Edward T. H. Yeh, Houston, TX (US)

(73) Assignee: Board of Regents, the University of Texas System, Austin, TX (US)

(*) Notice: Subject to any disclaimer, the term of this patent is extended or adjusted under 35 U.S.C. 154(b) by 0 days.

(21) Appl. No.: 11/214,440

(22) Filed: Aug. 29, 2005

(65) Prior Publication Data

US 2006/0057623 A1 Mar. 16, 2006

Related U.S. Application Data

(60) Provisional application No. 60/604,862, filed on Aug. 27, 2004.

(51) Int. Cl.
*C12Q 3/00* (2006.01)
*G01N 33/53* (2006.01)
(52) U.S. Cl. .................................. 435/6; 435/7.1
(58) Field of Classification Search .................. 435/6, 435/7.1
See application file for complete search history.

(56) References Cited

OTHER PUBLICATIONS

Tockman et al (Cancer Res., 1992, 52:2711s-2718s).*
Alberts et al. (Molecular Biology of the Cell, 3rd edition, 1994, p. 465).*
Lewin, B. (Genes VI, Oxford University Press, Inc., NY, Chapter 29, 1997).*
Greenbaum et al. (Genome Biology, 2003, vol. 4, Issue 9, pp. 117.1-117.8).*
Mallampalli et al. (Biochem. J. vol. 318, 1996, pp. 333-341).*
Fu et al (EMBO Journal, 1996, vol. 15, pp. 4392-4401).*
Bachant et al., "The SUMO-1 Isopeptidase Smt4 Is Linked to Centromeric Cohesion through SUMO-1 Modification of DNA Topoisomerase II," *Molecular Cell*, 9: 1169-1182, 2002.
Best et al., "SUMO-1 protease-1 regulates gene transcription through PML," *Mol. Cell*, 10: 843-855, 2002.
Chauchereau et al., "Sumoylation of the progesterone receptor and of the steroid receptor coactivator SRC-1," *J. Biol. Chem.*, 278(14): 12335-43, 2003.
Colombo et al., "The adenovirus protein Gam1 interferes with sumoylation of histone deacetylase 1," *EMBO Rep.*, 3: 1062-1068, 2002.
Culig, "Androgen receptors in prostate cancer," *J. Urol.*, 170: 1363-1369, 2003.
David et al., "SUMO-1 modification of histone deacetylase 1 (HDAC1) modulates its biological activities," *J. Biol. Chem.*, 277(26): 23658-63, 2002.
De Marzo et al., "Pathological and molecular aspects of prostate cancer," *Lancet*, 361: 955-964, 2003.
De Ruijter et al., "Histone deacetylases (HDACs): characterization of the classical HDAC family," *Biochem. J.*, 370: 737-749, 2003.
Debes et al., "The role of androgens and the androgen receptor in prostate cancer," *Cancer Letters*, 187: 1-7, 2002.

Desterro et al., "SUMO-1 Modification of IκBα Inhibits NF-κB Activation," *Molecular Cell*, 2: 233-239, 1998.
Duprez et al., "SUMO-1 modification of the acute promyelocytic leukaemia protein PML: implications for nuclear localisation," *Journal of Cell Science*, 112: 381-393, 1999.
Freiman et al., "Regulating the Regulators: Lysine Modifications Make Their Mark," *Cell*, 112: 11-17, 2003.
Fu et al., "Androgen Receptor Acetylation Governs *trans* Activation and MEKK1-Induced Apoptosis without Affecting In Vitro Sumoylation and *trans*-Repression Function," *Mol. Cell. Biol.*, 22(10): 3373-3388, 2002.
Gaughan et al., "Tip60 and Histone Deacetylase 1 Regulate Androgen Receptor Activity through Changes to the Acetylation Status of the Receptor," *J. Biol. Chem.*, 277(29): 25904-25913, 2002.
Gelmann, "Molecular Biology of the Androgen Receptor," *J. Clin. Oncol.*, 20(13): 3001-3015, 2002.
Gill, "Post-translational modifiation by the small ubiquitin-related modifier SUMO has big effects on transcription factor activity," *Curr. Opin. Genet. Dev.*, 13: 108-113, 2003.
Girdwood et al., "p300 Transcriptional Repression Is Mediated by SUMO Modification," *Molecular Cell*, 11: 1043-1054, 2003.
Glass et al., "The coregulator exchange in transcriptional functions of nuclear receptors," *Genes & Development*, 14: 121-141, 2000.
Gong et al., "Differential regulation of sentrinized proteins by a novel sentrin-specific protease," *J. Biol. Chem.*, 275: 3355-3359, 2000.
Gong et al., "Molecular cloning and characterization of human AOS1 and UBA2, components of the sentrin-activating enzyme complex," *FEBS Letters*, 448: 185-189, 1999.
Gong et al., "Preferential Interaction of Sentrin with a Ubiquitin-conjugating Enzyme, Ubc9," *J. Biol. Chem.*, 272(45): 28198-28201, 1997.
Gostissa et al., "Activation of p53 by conjugation to the ubiquitin-like protein SUMO-1," *The EMBO Journal*, 18(22): 6462-6471, 1999.
Grossmann et al., "Androgen Receptor Signaling in Androgen-Refractory Prostate Cancer," *Journal of the National Cancer Institute*, 93(22): 1687-1697, 2001.
Hang et al., "Association of the human SUMO-1 protease SENP2 with the nuclear pore," *J. Biol. Chem.*, 277: 19961-19966, 2002.
Hay, "Protein modification by SUMO," *TRENDS in Biochemical Sciences*, 26(5): 332-333, 2001.
Heinlein et al., "Androgen Receptor (AR) Coregulators: An Overview," *Endocrine Reviews*, 23(2): 175-200, 2002.
Hochstrasser, "SP-RING for SUMO: New Functions Bloom for a Uniquitin-like Protein," *Cell*, 107: 5-8, 2001.
Johnson et al., "An E3-like Factor that Promotes SUMO Conjugation to the Yeast Septins," *Cell*, 106: 735-744, 2001.
Kagey et al., "The Polycomb Protein Pc2 Is a SUMO E3," *Cell*, 113: 127-137, 2003.

(Continued)

*Primary Examiner*—Sean E Aeder
(74) *Attorney, Agent, or Firm*—Fulbright & Jaworski LLP

(57) ABSTRACT

The present invention relates to compositions and methods for the use of SENP1 as a marker for cancer diagnosis, specifically prostate cancer. Still further, it relates to the use of inhibitors of SENP1 to inhibit cell proliferation of a neoplasm or tumor cell and to treat a hyperproliferative disease.

10 Claims, 34 Drawing Sheets

OTHER PUBLICATIONS

Kahyo et al., "Involvement of PIAS1 in the Sumoylation of Tumor Suppressor p53," *Molecular Cell*, 8: 713-718, 2001.

Kamitani et al., "Identification of Three Major Sentrinization Sites in PML," *J. Biol. Chem.*, 273(41): 26675-26682, 1998.

Kamitani et al., "Preferential Modification of Nuclear Proteins by a Novel Ubiquitin-like Molecule," *J. Biol. Chem.*, 272(22): 14001-14004, 1997.

Kim et al., "A new SUMO-1-specific protease, SUSP1, that is highly expressed in reproductive organs," *J. Biol. Chem.*, 275: 14102-14106, 2000.

Kirsh et al., "The SUMO E3 ligase RanBP2 promotes modification of the HDAC4 deacetylase," *EBMO J.*, 21: 2682-2691, 2002.

Kotaja et al., "The nuclear receptor interaction domain of GRIP1 is modulated by covalent attachment of SUMO-1," *J. Biol. Chem.*, 277: 30283-30288, 2002.

Le Drean et al., "Potentiation of Glucocorticoid Receptor Transcriptional Activity by Sumoylation," *Endocrinology*, 143(9): 3482-3489, 2002.

Lee et al., "Recent advances in androgen receptor action," *Cell. Mol. Life Sci.*, 60: 1613-1622, 2003.

Li et al., "A new protease required for cell-cycle progression in yeast," *Nature*, 398: 246-251, 1999.

Li et al., "Heterogeneous Expression and Functions of Androgen Receptor Co-Factors in Primary Prostate Cancer," *American Journal of Pathology*, 161(4): 1467-1474, 2002.

Li et al., "The yeast ULP2 (SMT4) gene encodes a novel protease specific for the ubiquitin-like Smt3 protein," *Mol. Cell. Biol.*, 20: 2367-2377, 2000.

Lin et al., "Phosphorylation-dependent ubiquitylation and degradation of androgen receptor by Akt require Mdm2 E3 ligase," *EMBO J.*, 21: 4037-4048, 2002.

Mahajan et al., "A Small Upbiquitin-Related Polypeptide Involved in Targeting RanGAP1 to Nuclear Pore Complex Protein RanBP2," *Cell*, 88: 97-107, 1997.

McKenna et al., "Combinatorial control of gene expression by nuclear receptors and coregulators," *Cell*, 108: 465-474, 2002.

Melchior, "SUMO—Nonclassical Ubiquitin," *Annu. Rev. Cell Dev. Biol.*, 16: 591-626, 2000.

Muller et al., "c-Jun and p53 Activity Is Modulated by SUMO-1 Modification," *J. Biol. Chem.*, 275(18): 13321-13329, 2000.

Muller et al., "Sumo, Ubiquitin's Mysterious Cousin," *Nature Reviews*, 2: 202-210, 2001.

Nagy et al., "Nuclear Receptor Repression Mediated by a Complex Containing SMRT, mSin3A, and Histone Deacetylase," *Cell*, 89: 373-380, 1997.

Nawaz et al., "Proteasome-dependent degradation of the human estrogen receptor," *Proc. Natl. Acad. Sci. USA*, 96: 1858-1862, 1999.

Nishida et al., "A novel mammalian Smt3-specific isopeptidase 1 (SMT3IP1) localized in the nucleolus at interphase," *Eur. J. Biochem.*, 267: 6423-6427, 2000.

Nishida et al., "Characterization of a novel mammalian SUMO-1/Smt3-specific isopeptidase, a homologue of rat axam, which is an axin-binding protein promoting beta-catenin degradation," *J. Biol. Chem.*, 276: 39060-39066, 2001.

Nishida et al., "PIAS1 and PIASxα Function as SUMO-E3 Ligases toward Androgen Receptor and Repress Androgen Receptor-dependent Transcription," *J. Biol. Chem.*, 277(44): 41311-41317, 2002.

Pichler et al., "The Nucleoporin RanBP2 Has SUMO1 E3 Ligase Activity," *Cell*, 108: 109-120, 2002.

Poukka et al., "Covalent modification of the androgen receptor by small ubiquitin-like modifier 1(SUMO-1)," *Proc. Natl. Acad. Sci. USA*, 97: 14145-14150, 2000.

Poukka et al., "Ubc9 interacts with the androgen receptor and activates receptor-dependent transcription," *J. Biol. Chem.*, 274: 19441-19446, 1999.

Ross et al., "SUMO-1 modification represses Sp3 transcriptional activation and modulates its subnuclear localization," *Mol. Cell*, 10: 831-842, 2002.

Saitoh et al., "SUMO-1: wrestling with a new ubiquitin-related modifier," *TIBS*, 22: 374-376, 1997.

Scherr et al., "National Comprehensive Cancer Network guidelines for the management of prostate cancer," *Urology*, 61(2 Suppl 1): 14-24, 2003.

Shang et al., "Formation of the Androgen Receptor Transcription Complex," *Molecular Cell*, 9: 601-610, 2002.

Stanbrough et al., "Prostatic intraepithelial neoplasia in mice expressing an androgen receptor transgene in prostate epithelium," *Proc. Natl. Acad. Sci. USA*, 98: 10823-10828, 2001.

Su et al., "JNK is involved in signal integration during costimulation of T lymphocytes," *Cell*, 77(5): 727-36, 1994 [abstract only].

Tian et al., "Small ubiquitin-related modifier-1 (SUMO-1) modification of the glucocorticoid receptor," *Biochem. J.*, 367: 907-911, 2002.

Tussie-Luna et al., "Physical and functional interactions of histone deacetylase 3 with TFII-I family proteins and PIASxbeta," *Proc. Natl. Acad. Sci. USA*, 99: 12807-12812, 2002.

Yeh et al., "Ubiquitin-like proteins: new wines in new bottles," *Gene*, 248: 1-14, 2000.

Yu et al., "Inhibition of Androgen Receptor-Mediated Transcription by Amino-Terminal Enhancer of split," *Mol. Cell. Biol*, 21(14): 4614-4625, 2001.

Zhang et al., "Enzymes of the SUMO Modification Pathway Localize to Filaments of the Nuclear Pore Complex," *Mol. Cell. Biol.*, 22(18): 6498-6508, 2002.

Zhang et al., "Interrogating androgen receptor function in recurrent prostate cancer," *Cancer Res.*, 63(15): 4552-60, 2003.

Andrianifahanana et al., "Mucin (MUC) Gene Expression in Human Pancreatic Adenocarcinoma and Chronic Pancreatitis: A Potential Role of MUC4 as a Tumor Marker of Diagnostic Significance1"; Clinical Cancer Research, Dec. 2001; 4033-4040: vol. 7.

Bailey et al., "Characterization of the Localization and Proteolytic Activity of the SUMO-specific Protease, SENP1"; J. Biol. Chem.; Jan. 2, 2004; 692-703, vol. 279(1).

Brahimi-Horn et al., "The role of the hypoxia-inducible factor in tumor metabolism growth and invasion"; Bulletin du Cancer, E73-80; 2006, vol. 93 (8), Electronic Journal of Oncology.

Kim et al., "Regulation of vascular endothelial growth factor expression by insulin-like growth factor-II in human keratinocytes, differential involvement of mitogen-activated protein kinases and feedback inhibition of protein kinase C", Br J Dermatol.; Mar. 2005; 418-25; vol. 152(3).

\* cited by examiner

SEQUENCE LISTING

<160> NUMBER OF SEQ ID NOS: 21

<210> SEQ ID NO 1
<211> LENGTH: 643
<212> TYPE: PRT
<213> ORGANISM: Homo sapiens

<400> SEQUENCE: 1

Met Asp Asp Ile Ala Asp Arg Met Arg Met Asp Ala Gly Glu Val Thr
 1               5                  10                  15

Leu Val Asn His Asn Ser Val Phe Lys Thr His Leu Leu Pro Gln Thr
                20                  25                  30

Gly Phe Pro Glu Asp Gln Leu Ser Leu Ser Asp Gln Gln Ile Leu Ser
             35                  40                  45

Ser Arg Gln Gly His Leu Asp Arg Ser Phe Thr Cys Ser Thr Arg Ser
     50                  55                  60

Ala Ala Tyr Asn Pro Ser Tyr Tyr Ser Asp Asn Pro Ser Ser Asp Ser
 65                  70                  75                  80

Phe Leu Gly Ser Gly Asp Leu Arg Thr Phe Gly Gln Ser Ala Asn Gly
                 85                  90                  95

Gln Trp Arg Asn Ser Thr Pro Ser Ser Ser Ser Leu Gln Lys Ser
                100                 105                 110

Arg Asn Ser Arg Ser Leu Tyr Leu Glu Thr Arg Lys Thr Ser Ser Gly
            115                 120                 125

Leu Ser Asn Ser Phe Ala Gly Lys Ser Asn His His Cys His Val Ser
130                 135                 140

Ala Tyr Glu Lys Ser Phe Pro Ile Lys Pro Val Pro Ser Pro Ser Trp
145                 150                 155                 160

Ser Gly Ser Cys Arg Arg Ser Leu Leu Ser Pro Lys Lys Thr Gln Arg
                165                 170                 175

Arg His Val Ser Thr Ala Glu Glu Thr Val Gln Glu Glu Arg Glu
            180                 185                 190

Ile Tyr Arg Gln Leu Leu Gln Met Val Thr Gly Lys Gln Phe Thr Ile
            195                 200                 205

Ala Lys Pro Thr Thr His Phe Pro Leu His Leu Ser Arg Cys Leu Ser
210                 215                 220

Ser Ser Lys Asn Thr Leu Lys Asp Ser Leu Phe Lys Asn Gly Asn Ser
225                 230                 235                 240

Cys Ala Ser Gln Ile Ile Gly Ser Asp Thr Ser Ser Gly Ser Ala
                245                 250                 255

Ser Ile Leu Thr Asn Gln Glu Gln Leu Ser His Ser Val Tyr Ser Leu
                260                 265                 270

Ser Ser Tyr Thr Pro Asp Val Ala Phe Gly Ser Lys Asp Ser Gly Thr
            275                 280                 285

Leu His His Pro His His His Ser Val Pro His Gln Pro Asp Asn
            290                 295                 300

Leu Ala Ala Ser Asn Thr Gln Ser Glu Gly Asp Ser Val Ile Leu
305                 310                 315                 320

Leu Lys Val Lys Asp Ser Gln Thr Pro Thr Pro Ser Thr Phe Phe
                325                 330                 335

Gln Ala Glu Leu Trp Ile Lys Glu Leu Thr Ser Val Tyr Asp Ser Arg
                340                 345                 350

Ala Arg Glu Arg Leu Arg Gln Ile Glu Glu Gln Lys Ala Leu Ala Leu

-continued

```
                355                 360                 365
Gln Leu Gln Asn Gln Arg Leu Gln Glu Arg Glu His Ser Val His Asp
        370                 375                 380
Ser Val Glu Leu His Leu Arg Val Pro Leu Glu Lys Glu Ile Pro Val
385                 390                 395                 400
Thr Val Val Gln Glu Thr Gln Lys Lys Gly His Lys Leu Thr Asp Ser
                405                 410                 415
Glu Asp Glu Phe Pro Glu Ile Thr Glu Met Glu Lys Glu Ile Lys
        420                 425                 430
Asn Val Phe Arg Asn Gly Asn Gln Asp Glu Val Leu Ser Glu Ala Phe
                435                 440                 445
Arg Leu Thr Ile Thr Arg Lys Asp Ile Gln Thr Leu Asn His Leu Asn
        450                 455                 460
Trp Leu Asn Asp Glu Ile Ile Asn Phe Tyr Met Asn Met Leu Met Glu
465                 470                 475                 480
Arg Ser Lys Glu Lys Gly Leu Pro Ser Val His Ala Phe Asn Thr Phe
                485                 490                 495
Phe Phe Thr Lys Leu Lys Thr Ala Gly Tyr Gln Ala Val Lys Arg Trp
                500                 505                 510
Thr Lys Lys Val Asp Val Phe Ser Val Asp Ile Leu Leu Val Pro Ile
        515                 520                 525
His Leu Gly Val His Trp Cys Leu Ala Val Val Asp Phe Arg Lys Lys
        530                 535                 540
Asn Ile Thr Tyr Tyr Asp Ser Met Gly Gly Ile Asn Asn Glu Ala Cys
545                 550                 555                 560
Arg Ile Leu Leu Gln Tyr Leu Lys Gln Glu Ser Ile Asp Lys Lys Arg
                565                 570                 575
Lys Glu Phe Asp Thr Asn Gly Trp Gln Leu Phe Ser Lys Lys Ser Gln
                580                 585                 590
Ile Pro Gln Gln Met Asn Gly Ser Asp Cys Gly Met Phe Ala Cys Lys
        595                 600                 605
Tyr Ala Asp Cys Ile Thr Lys Asp Arg Pro Ile Asn Phe Thr Gln Gln
        610                 615                 620
His Met Pro Tyr Phe Arg Lys Arg Met Val Trp Glu Ile Leu His Arg
625                 630                 635                 640
Lys Leu Leu

<210> SEQ ID NO 2
<211> LENGTH: 643
<212> TYPE: PRT
<213> ORGANISM: Homo sapiens

<400> SEQUENCE: 2

Met Asp Asp Ile Ala Asp Arg Met Arg Met Asp Ala Gly Glu Val Thr
1               5                   10                  15
Leu Val Asn His Asn Ser Val Phe Lys Thr His Leu Leu Pro Gln Thr
                20                  25                  30
Gly Phe Pro Glu Asp Gln Leu Ser Leu Ser Asp Gln Ile Leu Ser
        35                  40                  45
Ser Arg Gln Gly His Leu Asp Arg Ser Phe Thr Cys Ser Thr Arg Ser
        50                  55                  60
Ala Ala Tyr Asn Pro Ser Tyr Tyr Ser Asp Asn Pro Ser Ser Asp Ser
65                  70                  75                  80
Phe Leu Gly Ser Gly Asp Leu Arg Thr Phe Gly Gln Ser Ala Asn Gly
```

-continued

```
                    85                  90                  95
Gln Trp Arg Asn Ser Thr Pro Ser Ser Ser Ser Leu Gln Lys Ser
            100                 105                 110
Arg Asn Ser Arg Ser Leu Tyr Leu Glu Thr Arg Lys Thr Ser Ser Gly
            115                 120                 125
Leu Ser Asn Ser Phe Ala Gly Lys Ser Asn His His Cys His Val Ser
            130                 135                 140
Ala Tyr Glu Lys Ser Phe Pro Ile Lys Pro Val Pro Ser Pro Ser Trp
145                 150                 155                 160
Ser Gly Ser Cys Arg Arg Ser Leu Leu Ser Pro Lys Lys Thr Gln Arg
                    165                 170                 175
Arg His Val Ser Thr Ala Glu Glu Thr Val Gln Glu Glu Arg Glu
                    180                 185                 190
Ile Tyr Arg Gln Leu Leu Gln Met Val Thr Gly Lys Gln Phe Thr Ile
                    195                 200                 205
Ala Lys Pro Thr Thr His Phe Pro Leu His Leu Ser Arg Cys Leu Ser
            210                 215                 220
Ser Ser Lys Asn Thr Leu Lys Asp Ser Leu Phe Lys Asn Gly Asn Ser
225                 230                 235                 240
Cys Ala Ser Gln Ile Ile Gly Ser Asp Thr Ser Ser Gly Ser Ala
                    245                 250                 255
Ser Ile Leu Thr Asn Gln Glu Gln Leu Ser His Ser Val Tyr Ser Leu
            260                 265                 270
Ser Ser Tyr Thr Pro Asp Val Ala Phe Gly Ser Lys Asp Ser Gly Thr
            275                 280                 285
Leu His His Pro His His His Ser Val Pro His Gln Pro Asp Asn
290                 295                 300
Leu Ala Ala Ser Asn Thr Gln Ser Glu Gly Ser Asp Ser Val Ile Leu
305                 310                 315                 320
Leu Lys Val Lys Asp Ser Gln Thr Pro Thr Pro Ser Ser Thr Phe Phe
                    325                 330                 335
Gln Ala Glu Leu Trp Ile Lys Glu Leu Thr Ser Val Tyr Asp Ser Arg
            340                 345                 350
Ala Arg Glu Arg Leu Arg Gln Ile Glu Glu Gln Lys Ala Leu Ala Leu
            355                 360                 365
Gln Leu Gln Asn Gln Arg Leu Gln Glu Arg Glu His Ser Val His Asp
            370                 375                 380
Ser Val Glu Leu His Leu Arg Val Pro Leu Glu Lys Glu Ile Pro Val
385                 390                 395                 400
Thr Val Val Gln Glu Thr Gln Lys Lys Gly His Lys Leu Thr Asp Ser
                    405                 410                 415
Glu Asp Glu Phe Pro Glu Ile Thr Glu Glu Met Glu Lys Glu Ile Lys
            420                 425                 430
Asn Val Phe Arg Asn Gly Asn Gln Asp Glu Val Leu Ser Glu Ala Phe
            435                 440                 445
Arg Leu Thr Ile Thr Arg Lys Asp Ile Gln Thr Leu Asn His Leu Asn
450                 455                 460
Trp Leu Asn Asp Glu Ile Ile Asn Phe Tyr Met Asn Met Leu Met Glu
465                 470                 475                 480
Arg Ser Lys Glu Lys Gly Leu Pro Ser Val His Ala Phe Asn Thr Phe
            485                 490                 495
Phe Phe Thr Lys Leu Lys Thr Ala Gly Tyr Gln Ala Val Lys Arg Trp
            500                 505                 510
```

```
Thr Lys Lys Val Asp Val Phe Ser Val Asp Ile Leu Leu Val Pro Ile
            515                 520                 525
His Leu Gly Val His Trp Cys Leu Ala Val Val Asp Phe Arg Lys Lys
        530                 535                 540
Asn Ile Thr Tyr Tyr Asp Ser Met Gly Gly Ile Asn Asn Glu Ala Cys
545                 550                 555                 560
Arg Ile Leu Leu Gln Tyr Leu Lys Gln Ser Ile Asp Lys Lys Arg
                565                 570                 575
Lys Glu Phe Asp Thr Asn Gly Trp Gln Leu Phe Ser Lys Lys Ser Gln
            580                 585                 590
Ile Pro Gln Gln Met Asn Gly Ser Asp Cys Gly Met Phe Ala Cys Lys
            595                 600                 605
Tyr Ala Asp Cys Ile Thr Lys Asp Arg Pro Ile Asn Phe Thr Gln Gln
        610                 615                 620
His Met Pro Tyr Phe Arg Lys Arg Met Val Trp Glu Ile Leu His Arg
625                 630                 635                 640

Lys Leu Leu
```

<210> SEQ ID NO 3
<211> LENGTH: 2512
<212> TYPE: DNA
<213> ORGANISM: Homo sapiens

<400> SEQUENCE: 3

```
acctagcgac tcttccggtg ctgtgaaggc ggttccggtt cgcggcggtt cccgggtttt    60
gcgttccgcg cccggccgga aaccccttcg catggcagcc ggttccggtt cggactttgt   120
atctttgcta aagtcagtga tgtgaaaaga cttgaaatgg atgatattgc tgataggatg   180
aggatggatg ctggagaagt gactttagtg aaccacaact ccgtattcaa acccacctc   240
ctgcccacaaa caggttttcc agaggaccag cttcgctt ctgaccagca gattttatct   300
tccaggcaag gacatttgga ccgatctttt acatgttcca caagaagtgc agcttataat   360
ccaagctatt actcagataa tccttcctca gacagttttc ttggctcagg cgattaaga   420
acctttggcc agagtgcaaa tggccaatgg agaaattcta ccccatcgtc aagctcatct   480
ttacaaaaat caagaaacag ccgaagtctt tacctcgaaa cccgaaagac tcaagtgga   540
ttatcaaaca gttttgcggg aaagtcaaac catcactgcc atgtatctgc atatgaaaaa   600
tcttttccta ttaaacctgt tccagtcca tcttggagtg ttcatgtcg tcgaagtctt   660
ttgagcccca gaaaaactca gaggcgacat gttagtacag cagaagagac agttcaagaa   720
gaagaaagag agatttacag acagctgcta cagatggtca cagggaaaca gtttactata   780
gccaaaccca ccacacattt tcctttacac ctgtctcgat gtcttagttc cagtaaaaat   840
actttgaaag actcactgtt taaaaatgga aactcttgtg catctcagat cattggctct   900
gatacttcat catctggatc tgccagcatt ttaactaacc aggaacagct gtcccacagt   960
gtatattccc tatcttctta taccccagat gttgcatttg gatccaaaga ttctggtact  1020
cttcatcatc cccatcatca ccactctgtt ccacatcagc cagataactt agcagcttca  1080
aatacacaat ctgaaggatc agactctgtg attttactga agtgaaaga ttcccagact  1140
ccaactccca gttctacttt cttccaggca gagctgtgga tcaaagaatt aactagtgtt  1200
tatgattctc gagcacgaga aagattgcgc cagattgaag aacagaaggc attggcctta  1260
cagcttcaaa accagagatt gcaggagcgg gaacattcag tacatgattc agtagaacta  1320
```

```
catcttcgtg tacctcttga aaaggagatt cctgttactg ttgtccaaga aacacaaaaa   1380
aaaggtcata aattaactga tagtgaagat gaatttcctg aaattacaga ggaaatggag   1440
aaagaaataa agaatgtatt tcgtaatggg aatcaggatg aagttctcag tgaagcattt   1500
cgcctgacca ttacacgcaa agatattcaa actctaaacc atctgaattg gctcaatgat   1560
gagatcatca atttctacat gaatatgctg atggagcgaa gtaaagagaa gggcttgcca   1620
agtgtgcatg catttaatac cttttttctt actaaattaa aaacggctgg ttatcaggca   1680
gtgaaacgtt ggacaaagaa agtagatgta ttttctgttg acattctttt ggtgcccatt   1740
cacctgggag tacactggtg tctagctgtt gtggacttta aaagaagaa tattacctat   1800 tacgactcca tgggtgggat aaacaatgaa gcctgcagaa tactcttgca atacctaaag   1860
caagaaagca ttgacaagaa aaggaaagag tttgacacca atggctggca gcttttcagc   1920
aagaaaagcc agattcctca gcagatgaat ggaagtgact gtgggatgtt tgcctgcaaa   1980
tatgctgact gtattaccaa agacagacca atcaacttca cacagcaaca catgccatac   2040
ttccggaagc ggatggtctg ggagatcctc caccgaaaac tcttgtgaag actgtctcac   2100
ttagcagacc ttgaccatgt gggggaccag ctctttgttg tctacagcca gagaccttgg   2160
aaacagctgc tcccagccct ctgctgttgt aacacccttg atcctggacc aggccctggc   2220
gagatgcatt cacaagcaca tctgcctttc cttttgtatc tcagatacta ttttttgcaaa   2280 gaaactttgg tgctgtgaaa ggggtgaggg acatccctaa gctgaagaga gagactgctt   2340
ttcacttctt cagttctgcc atcttgtttt caaagggctc cagcctcact cagtccctaa   2400
ttatgggact gagaaaagct tggaaagaat cttggtttca tataaattct tgttgttagg   2460
ccttactaag aagtaggaaa gggcatgggc aaaaggtagg gataaaaacc ac           2512

<210> SEQ ID NO 4
<211> LENGTH: 4726
<212> TYPE: DNA
<213> ORGANISM: Homo sapiens

<400> SEQUENCE: 4
cctgctgtcc ggtggccgcg ctgtggccgc cggtggccgt taggctacct gaggccgttc     60
cttctggtct ctctctcctg ggccgcggag agaccgtctc cctgccgtta cagcaggccc    120
catcccagcg cccagccgta cttggggaaa ggccggttgc gattccgggg ctttcccgcc    180
agagctgggt cttctctggg gagagctgtt ttcaccggga agctcggctt tctgtggtac    240
cggcttcatc tcccgccttc cttgagaccc gagtgatatt tcttgactac ttctgcgtct    300
cacgtaaaca tttctccaac tctcctactc tgtggtatct ccctgagatg tgatatcgct    360
agtgccacca tcagaaagaa acgtctggac cctcctgctc aggactttgt atctttgcta    420
aagtcagtga tgtgaaaaga cttgaaatgg atgatattgc tgataggatg aggatggatg    480
ctggagaagt gactttagtg aaccacaact ccgtattcaa aacccacctc ctgccacaaa    540
caggttttcc agaggaccag ctttcgcttt ctgaccagca gattttatct tccaggcaag    600
gacatttgga ccgatctttt acatgttcca caagaagtgc agcttataat ccaagctatt    660
actcagataa tccttcctca gacagttttc ttggctcagg cgatttaaga acctttggcc    720
agagtgcaaa tggccaatgg agaaattcta ccccatcgtc aagctcatct ttacaaaaat    780
caagaaacag ccgaagtctt tacctcgaaa cccgaaagac ctcaagtgga ttatcaaaca    840
gttttgcggg aaagtcaaac catcactgcc atgtatctgc atatgaaaaa tcttttccta    900
ttaaacctgt tccaagtcca tcttggagtg gttcatgtcg tcgaagtctt ttgagcccca    960
```

-continued

```
agaaaactca gaggcgacat gttagtacag cagaagagac agttcaagaa gaagaaagag    1020
agatttacag acagctgcta cagatggtca cagggaaaca gtttactata gccaaaccca    1080
ccacacattt tcctttacac ctgtctcgat gtcttagttc cagtaaaaat actttgaaag    1140
actcactgtt taaaaatgga aactcttgtg catctcagat cattggctct gatacttcat    1200
catctggatc tgccagcatt ttaactaacc aggaacagct gtcccacagt gtatattccc    1260
tatcttctta taccccagat gttgcatttg atccaaaga ttctggtact cttcatcatc     1320
cccatcatca ccactctgtt ccacatcagc cagataactt agcagcttca aatacacaat    1380
ctgaaggatc agactctgtg attttactga aagtgaaaga ttcccagact ccaactccca    1440
gttctacttt cttccaggca gagctgtgga tcaaagaatt aactagtgtt tatgattctc    1500
gagcacgaga aagattcgcg cagattgaag aacagaaggc attggcctta cagcttcaaa    1560
accagagatt gcaggagcgg gaacattcag tacatgattc agtagaacta catcttcgtg    1620
tacctcttga aaaggagatt cctgttactg ttgtccaaga aacacaaaaa aaaggtcata    1680
aattaactga tagtgaagat gaatttcctg aaattacaga ggaaatggag aaagaaataa    1740
agaatgtatt tcgtaatggg aatcaggatg aagttctcag tgaagcattt cgcctgacca    1800
ttacacgcaa agatattcaa actctaaacc atctgaattg gctcaatgat gagatcatca    1860
atttctacat gaatatgctg atggagcgaa gtaaagagaa gggcttgcca agtgtgcatg    1920
catttaatac cttttctctc actaaaattaa aaacggctgg ttatcaggca gtgaaacgtt    1980
ggacaaagaa agtagatgta ttttctgttg acattctttt ggtgcccatt cacctgggag    2040
tacactggtg tctagctgtt gtggacttta gaaagaagaa tattacctat tacgactcca    2100
tgggtgggat aaacaatgaa gcctgcagaa tactcttgca atacctaaag caagaaagca    2160
ttgacaagaa aaggaaagag tttgacacca atggctggca gcttttcagc aagaaaagcc    2220
agattcctca gcagatgaat ggaagtgact gtgggatgtt tgcctgcaaa tatgctgact    2280
gtattaccaa agacagacca atcaacttca cacagcaaca catgccatac ttccggaagc    2340
ggatggtctg ggagatcctc caccgaaaac tcttgtgaag actgtctcac ttagcagacc    2400
ttgaccatgt ggggggaccag ctcttttgttg tctacagcca gagaccttgg aaacagctgc    2460
tcccagccct ctgctgttgt aacacccttg atcctggacc aggccctggc gagatgcatt    2520
cacaagcaca tctgcctttc cttttgtatc tcagatacta ttttttgcaaa gaaactttgg    2580
tgctgtgaaa ggggtgaggg acatccctaa gctgaagaga gagactgctt ttcacttctt    2640
cagttctgcc atcttgtttt caaagggctc cagcctcact cagtccctaa ttatgggact    2700
gagaaaagct tggaaagaat cttggttca tataaattct tgttgttagg ccttactaag     2760
aagtaggaaa gggcatgggc aaaaggtagg gataaaaacc accagcatat acatggacat    2820
acacacacac ccacacacac aaacacacac acacacacaa ttttcacgat gtatggtcag    2880
gaatgtgact gtaaactgga cttttggggcc caggcataag tcccttcctc caggaccttt    2940
cctatttata tgtccctata caaaatccat ctgctttat acgtagctgt tttatcatct     3000
gtagcttcat cctatccgga ggcacagcac atgagccctg acaggtccc aaagttccaa     3060
gcagtccttt ccgtaaaagc aggggtttgc atgtgctacc aacacatgat acggggaaga    3120
cccacccagg gagcggtttc agtggcgcaa caaagcacca cttttactgt tgcctacttc    3180
tgaccaagaa gaaaaaggac cttagtattt agcataaaat tccagcgctg gatgaatgca    3240
gatctagttt ggtctgtggc tagttttaat atgtttctaa ccacagagaa tttcatatat    3300
```

```
atatacatat atatatacac atacatatat atatatatat atgtatgtat aaaatttcac    3360
agggatatgc ttttttttt aaagactgaa tgtgttcacc atttagcctg tagatttatt     3420 tccatttttcc aaattccagc acacagagat cccagcccct atgagtaggg tgtttgtgga   3480
ctacctaatg gaatatttt gaggcctgga tgaactttgc catatgggta gaggttacag    3540
agggaggtga tattttcagc taaaaaaaaa aacgggtgga gtttggactg atcaacttga   3600
gatttaaaaa ctgctattcc ttttgttctt tctagcatct ctccccaccc tctgagagct   3660
cctcaggctt agatagtgaa gtgatcaaat gccagtgtca ttttgtactt aagttccaaa   3720
gtaggaacat tttatactt tttctgtatt gtaataggta gttttgtatg aaatcttttc    3780
tcctctcccg ttgtaccgca ttcttttccag cattgtgctt tttccctggg cttatttgaa  3840
aattttactg ttttatacaa gctcgtttag tacatttttc tatgttttac cacaagttac   3900
aatttgaaaa gaaaactatt tttttaaat attccattgt taactgaatg ttactgtttc    3960
cactccagca actacatgtc ctcccttcaa ctgcctgcct tttggggaaa gaccacctt    4020 tgtgtgtttg ttttttctct ctcttttctt cccttctctt ttctatctct ctttatttt   4080 ctttctttt ctttgttttt gagttttcta taggaaataa atagctttct atatatgagt   4140
tgctggggac cttcacattc tcttttagaa agctgtggca tgcagtctca ttgcaggact   4200 cctggaaat tgtctggttc ttggtattta ctgtatgtaa gcaacaactt gaaaggtggc    4260
aatatggtgt cgatttggac tatgaatcaa aagaccttt tcaggttctt tcactattgt   4320
ctgggggact cagaacaaga ttgttctctg tatttattgt ttgtccattt aggtaacatc   4380
tgtcttacct tcctcacaga ctttgtacag accaaagcaa caatatttta ttgccatgta   4440
tagcagaaaa tgaaacatgc aacaaaagca ctttgaaaaa tatataagga attgttgagc   4500
ctgtctgaat ttgggccccc tttctgacta atgcagtttt gcacaaggta gaagttagtg   4560
accctgagac catcttacca ccctggacct ggtccaaata cagacttaca cagtggacca   4620
ttctttcctg agctagccaa caagagcagg agtagtatct ggaaactttc ccctttgttt   4680
aggggtaggc tttgatgacc aggaaaaaaa aaaaggtatt tctgca               4726
```

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 5
ttggccagag tgcaaatgg                                                 19

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 6
tcggctgttt cttgatttt gtaa                                            24

<210> SEQ ID NO 7
<211> LENGTH: 21
<212> TYPE: DNA
<213> ORGANISM: Artificial Sequence -continued

```
<220> FEATURE:
<223> OTHER INFORMATION: Description of Artificial Sequence: Synthetic
      Primer

<400> SEQUENCE: 7
gtgaaccaca actccgtatt c                                              21

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
cagctgggcc gcccttgt                                                  18

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
cagctgggga gggctgtgg                                                 19

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
ttaaaaaaaa tgagtcagaa tggagatcac                                     30

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11
cagctgggga gggctgtg                                                  18

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 12
taacaacagt aacgtcacac ggactacagg                                     30

<210> SEQ ID NO 13
<211> LENGTH: 18
<212> TYPE: DNA
<213> ORGANISM: Artificial Sequence
<220> FEATURE:
```

<223> OTHER INFORMATION: Description of Artificial Sequence: Synthetic
      Primer

<400> SEQUENCE: 13 cagctggga gggctgtg                                                         18

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14
taacaacagt ggcgtcacac gg                                                   22

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15
ccgtgtgacg ccactgttgt ta                                                   22

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 16
agaggaccag ctttcgcttt ctga                                                 24

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 17
ttgaggtctt tcgggtttcg aggt                                                 24

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 18
cggagtcaac ggatttggtc gtat                                                 24

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic -continued

```
      Primer

<400> SEQUENCE: 19
agccttctcc atggtggtga agac                                           24

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 20
agaagctgtg catctacacc gaca                                           24

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 21
tgggtcacac ttgatcactc tgga                                           24
```

SENP1 AS A MARKER OF CANCER DEVELOPMENT AND TARGET FOR CANCER THERAPY

CROSS-REFERENCE TO RELATED APPLICATIONS

This application claims priority to U.S. Provisional Application No. 60/604,862 filed Aug. 27, 2004, which is incorporated herein by reference in its entirety.

STATEMENT REGARDING FEDERALLY SPONSORED RESEARCH OR DEVELOPMENT

This invention was made with government support under Grant No.CA80089 awarded by the National Institutes of Health and under Grant No. W81XWH-04-0877 awarded by the Department of the Army. The United States Government has certain rights in the invention.

TECHNICAL FIELD

The present invention relates to the field of cancer biology. More specifically, it relates to the use of SENP1 as a marker for cancer diagnosis, specifically prostate cancer. Still further, it relates to the use of inhibitors of SENP1 to inhibit cell proliferation of a neoplasm or tumor cell and to treat a hyperproliferative disease.

BACKGROUND OF THE INVENTION

A. The SUMO Family of Ubiquitin-Like Proteins

Sentrin-1 (also called SUMO-1) is a protein that can covalently modify specific proteins in a manner analogous to ubiquitination (Okura et al., 1996; Kamitani et al., 1997a; Kamitani et al., 1997b; Matunis et al., 1996; Mahajan et al., 1997; Boddy et al., 1996; Hershko et al., 1998). In mammalian cells, there are three known sentrin family proteins that are expressed in all tissues and appear to have overlapping function (Kamitani et al., 1997a; Kamitani et al., 1997b; Kamitani et al., 1998a; Kamitani et al., 1998b).

In contrast to ubiquitination, sumoylation does not target protein for degradation. Sumoylation, in some cases, actually competes with ubiquitination on the same lysine residues, thus functions almost like an anti-ubiquitin (Desterro et al., 1998). Sumoylation can also alter a protein's cellular localization. For example, sumoylated RanGAP1 is localized in the nuclear envelope, whereas unmodified RanGAP1 is localized in the cytosol (Okura et al., 1996; Matunis et al., 1996). Finally, sumoylation of many transcriptional factors serves to alter their transcriptional activity (Girdwood et al., 2003; Gostissa et al., 1999; Buschmann et al., 2000; Hay et al., 1999; Kirsh et al., 2002; Lehembre et al., 2001; Kishi et al., 2003; Ross et al., 2002; Tojo et al., 2002; Muller et al., 2000).

Sumoylation is a dynamic process that is mediated by activating, conjugating, and ligating enzymes and readily reversed by a family of SUMO-specific proteases (Yeh et al., 2000; Li et al., 2000). In the mammalian system, four SUMO-specific proteases have been reported (Yeh et al., 2000; Gong et al., 2000, Best et al., 2002; Hang et al., 2002; Kim et al., 2000; Nishida et al., 2001; Nishida et al., 2000). SENP1 is a nuclear protease that appears to deconjugate a large number of sumoylated proteins (Gong et al., 2000). SENP2 is a nuclear envelope associated protease that appears to have similar activity as SENP1 when over-expressed (Gong et al., 2000, Hang et al., 2002, Zhang et al., 2002). There is a spliced isoform of mouse SENP2, called SuPr1, which could alter the distribution of nuclear POD-associated proteins, such as CBP and Daxx and converted Sp3 to a strong activator with diffuse nuclear localization (Ross et al., 2002; Best et al., 2002). Two additional SUMO-specific proteases (SENP3/SMT3IP1 and SENP6/SUSP1) have also been reported (Yeh et al., 2000; Kim et al., 2000). SENP3/SMT3IP1 is a nucleolar protein, whereas SENP6/SUSP1 is located in the cytosol (Kim et al., 2000). Although the ability of SENPs to reverse sumoylation is well established, the specificity of each SENP and the difference in the regulatory pathway mediated by each protease remains to be defined.

C. Sumoylation of Androgen Receptor and its Coregulators

Steroid receptors such as the androgen receptor (AR) are ligand-regulated transcription factors belonging to the nuclear receptor superfamily (McKenna et al., 2002). They convey the effects of steroid hormones on the regulation of cell growth, differentiation, and homeostasis (McKenna et al., 2002). To regulate transcription, the receptors bind to specific hormone response elements of target genes and exhibit crosstalk with other transcription factors through protein-protein interactions. A plethora of coregulatory proteins recognized by different functional domains of the receptors, the N-terminal transactivation region, the central DNA-binding domain, and the C-terminal ligand-binding domain, mediate transactivation and transrepression of nuclear receptors. Some nuclear receptors are also known to be ubiquitinated, which targets them for degradation (Lin et la., 2002; Nawaz et la., 1999). Ubc9, the conjugating enzyme for SUMO, has recently been shown to interact with at least two steroid receptors, AR and glucocorticoid receptor (Poukka et al., 1999; Tian et al., 2002). However, coexpressed Ubc9 enhanced AR-dependent transcription in a fashion that appeared to be independent of its ability to catalyze sumoylation (Poukka et al., 1999). AR is sumoylated in vivo at lysine residues 386 and 520 (Poukka et al., 2000). Mutation of these residues increases the transactivation ability of AR, suggesting that sumoylation is involved in the regulation of AR activity (Poukka et al., 2000).

Recently it has been found that four AR coregulators (e.g., p160 family of coactivators, including SRC-1, GRIP1/SRC-2, ACTR/AIB1/RAC3/pCIP, CBP, p300, and pCAF (McKenna et al., 2002)) are sumoylated. SRC-1 has five sumoylation sites and two major sites were localized in NR box situated in the nuclear receptor interacting region 1 (Chauchereau et al., 2003). It was observed that sumoylation can increase interaction of SRC-1 with the progesterone receptor. For the coactivator GRIP1, two residues located in the nuclear receptor interacting region were found to be sumoylated (Kotaja et al., 2002). Substitution of these two sumoylation sites could attenuate the activity of GRIP1 on AR-dependent transcription. HDAC1 and HDAC4 were also found to be sumoylated (David et al., 2002; Colombo et al., 2002; Tussie-Luna et al., 2002). Mutation of two sumoylation sites of HDAC1 profoundly reduced HDAC1-mediated transcriptional repression (David et al., 2002). HDAC4 sumoylation mutant showed a slightly impaired ability to repress transcription as well as reduced histone deacetylase activity (Kirsh et al., 2002).

Despite the lack of a precise understanding of the mechanisms by which androgens act on so many physiological relevant systems, it is readily understood why the AR is an important target in multiple areas of drug discovery and patient therapy. In the oncology area, for example, inhibitors (antagonists or partial antagonists) of androgen receptor function are useful for the treatment of androgen dependent prostate cancer while agonists or partial agonists of the AR are applicable to the treatment of breast cancer and/or prostate cancer. For metabolic and endocrine diseases disorders, agonists or partial agonists of the androgen receptor function are useful for the treatment of age-related diseases and conditions of cachexia in several disease states including, but not limited to, Acquired Immune Disease Syndrome (AIDS). Functional AR has also been identified in various bone cells and, as such, androgen administration has beneficial effects on skeletal development and maintenance in men and women.

E. Pathogenesis of Prostate Cancer

Tumor formation in prostate tissue is accountable for 30% of cancer-related deaths in men. In most case, the disease progresses from a benign hyperplasia to a prostate cancer precursor state referred to as prostatic intraepithelial neoplasia or PIN. PIN formation is replaced with rapidly proliferating prostate cancer cells that readily metastasize to other areas of the body. This atrophy of the prostate gland is attributed to changes at a molecular level. The most reported alteration is the enhanced expression and transcriptional activity of AR. In normal prostate tissue, endogenous androgens bind the AR and prompt translocation of the receptor to the nucleus. The activated AR associates with specific androgen response elements, recruits numerous transcriptional regulators (or AR coregulators), induces transcription of AR-response genes, and thereby promotes prostate growth. Studies in transgenic mice indicate that continuous activation of supra-physiological levels of ARs produces histological signs of prostate cancer as well as visible lesions (Stanbrough et al., 2001). The correlation between enhanced AR-dependent transcriptional activity and prostate carcinogenesis is well accepted; in fact, the expression of the AR-regulated prostate specific antigen (PSA) gene is used as a biological marker for diagnosis of prostate cancer (Culig et al., 2003; DeMarzo et al., 2003). Inhibition of AR activation with androgen ablation is the primary therapy for advanced and metastatic prostate cancer (Scherr et al., 2003). Androgen deprivation initially does induce tumor regression but eventually the tumor becomes unresponsive and averts to an androgen-independent or hormone refractory state.

Similar to androgen-dependent prostate cancer, AR-dependent transcription must be attenuated to arrest tumor proliferation in hormone refractory prostate cancer. However, cellular targets remain to be identified that can regulate AR-dependent transcription irrespective of the mechanism for AR activation (androgen-dependent and/or androgen-independent).

BRIEF SUMMARY OF THE INVENTION

Sentrin/SUMO-specific protease (SENP1) is upregulated by androgen and IL-6 increase SENP1 expression in hyperproliferative cells, for example, prostate cells. Over-expression of SENP1 leads to a marked amplification of androgen-receptor dependent transcription, which plays a role in cancer development. Thus, the present invention is drawn to identifying and manufacturing inhibitors of SENP1 that can be used to reduce or inhibit proliferation of hyperproliferative cells. Still further, it is envisioned that SENP1 may be used as a marker for diagnosis or monitoring cancer development.

An embodiment of the present invention is a method of inhibiting proliferation of a hyperproliferative cell comprising administering to the cell an effective amount of an SENP1 inhibitor, wherein said amount decreases SENP1 expression or activity thereby inhibiting cell proliferation. In certain embodiments, the inhibitor decreases the levels of androgen receptor (AR) transcription, and/or, decreases the levels of cyclin D1 expression, and/or decreases levels of c-jun transcription.

The cell is a tumor cell. More specifically, the tumor cell is a prostate tumor cell, for example, a prostatic intraepithelial neoplasia cell, a primary tumor cell, or a metastatic tumor cell.

In certain embodiments, the inhibitor is a nucleic acid molecule. More particularly, the nucleic acid molecule is an antisense molecule. Yet further, the antisense molecule may be an siRNA molecule, for example, the siRNA molecule may be an siRNA molecule that is encoded by the nucleic acid sequence of SEQ. ID. NO. 7.

Still further, the nucleic acid sequence may be comprised in an expression vector, which can be further defined as a viral or plasmid vector. Exemplary viral vectors include, but are not limited to an adenoviral vector, an adeno-associated viral vector, a retroviral vector, a lentiviral vector, a herpes viral vector, polyoma viral vector or hepatitis B viral vector. Alternatively, the expression vector may be comprised in a non-viral delivery system, for example, the non-viral delivery system comprises one or more lipids.

In further embodiments, the SENP1 inhibitor is prepared by the process of designing or selecting a candidate substance suspected of having the ability of decreasing SENP1 activity or SENP1 expression.

Yet further, the cell is in a subject suffering from a hyperproliferative disease, more particularly, the subject is a human patient.

In certain embodiments, the hyperproliferative disease is a cancer, for example, but not limited to melanoma, non-small cell lung cancer, small-cell lung cancer, lung cancer, leukemia, hepatocarcinoma, retinoblastoma, astrocytoma, glioblastoma, gum cancer, tongue cancer, neuroblastoma, head cancer, neck cancer, breast cancer, pancreatic cancer, prostate cancer, renal cancer, bone cancer, testicular cancer, ovarian cancer, mesothelioma, cervical cancer, gastrointestinal cancer, lymphoma, brain cancer, colon cancer, sarcoma or bladder cancer. More particularly, the cancer is prostate cancer.

In further embodiments, the hyperproliferative disease is rheumatoid arthritis, inflammatory bowel disease, osteoarthritis, leiomyomas, adenomas, lipomas, hemangiomas, fibromas, vascular occlusion, restenosis, atherosclerosis, preneoplastic lesions, carcinoma in situ, oral hairy leukoplakia, or psoriasis.

Still further, the present invention comprises an isolated nucleic acid sequence that encodes an SENP1 siRNA molecule. Using the nucleic acid sequence of SENP1 and the publicly available siRNA techniques of obtaining siRNA molecules, one of skill in the would be able to obtain such nucleic acid sequences encoding SENP1 siRNA molecules. An exemplary nucleic acid sequence that encodes an SENP1 siRNA molecule may include the sequence of SEQ. ID. NO. 7. The nucleic sequence may be comprised in an expression vector, for example, a viral or plasmid vector. The viral vector is an adenoviral vector, an adeno-associated viral vector, a retroviral vector, a lentiviral vector, a herpes viral vector, polyoma viral vector or hepatitis B viral vector. In other embodiments, the isolated nucleic acid sequence that encodes an SENP1 siRNA molecule may be comprised in a non-viral delivery system, for example, the non-viral delivery system comprises one or more lipids.

A further embodiment of the present invention is a method of diagnosing a hyperproliferative disease comprising obtaining a biological sample from a subject and assessing the expression or activity of SENP1 in the biological sample from a subject suspected of suffering from the hyperproliferative disease. The hyperproliferative disease may be further defined as cancer, for example, melanoma, non-small cell lung cancer, small-cell lung cancer, lung cancer, leukemia, hepatocarcinoma, retinoblastoma, astrocytoma, glioblastoma, gum cancer, tongue cancer, neuroblastoma, head cancer, neck cancer, breast cancer, pancreatic cancer, prostate cancer, renal cancer, bone cancer, testicular cancer, ovarian cancer, mesothelioma, cervical cancer, gastrointestinal cancer, lymphoma, brain cancer, colon cancer, sarcoma or bladder cancer. In further embodiments, the hyperproliferative disease may be rheumatoid arthritis, inflammatory bowel disease, osteoarthritis, leiomyomas, adenomas, lipomas, hemangiomas, fibromas, vascular occlusion, restenosis, atherosclerosis, pre-neoplastic lesions, carcinoma in situ, oral hairy leukoplakia, or psoriasis.

The biological sample can be obtained from a fluid sample (e.g., blood, serum or other bodily fluids, e.g., urine, etc.) a tissue biospy and/or aspiration of tissue or cells during a surgical procedure. In certain embodiments, the biological sample is a tissue sample, which may comprise a cell, for example, a tumor cell. The tumor cell is a prostate tumor cell or a prostatic intraepithelial neoplasia.

Another embodiment of the present invention is a method of manufacturing an SENP1 inhibitor comprising: providing a candidate substance suspected of decreasing SENP1 expression or activity; selecting the SENP1 inhibitor by assessing the ability of the candidate substance to decrease SENP1 expression or activity; and manufacturing the selected SENP1 inhibitor. It is envisioned that the candidate substance may be a protein, a nucleic acid molecule, an organo-pharmaceutical, or a combination thereof.

In further embodiments, the providing step is further defined as providing in a cell or a cell-free system an SENP1 polypeptide and the SENP1 polypeptide is contacted with the candidate substance. In certain instances, the candidate substance is a protein in which the protein is an antibody that binds immunologically to SENP1.

Yet further, the providing step is further defined as providing a nucleic acid molecule that encodes the SENP1 polypeptide. In certain instances, the candidate substance is a nucleic acid molecule. More particularly, the nucleic acid molecule is an antisense molecule and/or an siRNA molecule. The siRNA molecule is encoded by a nucleic acid sequence further defined as SEQ. ID. NO. 7.

Another embodiment is a kit for diagnosing a hyperproliferative disease comprising a compound that assesses the activity or expression of SENP1. The compound selectively binds a SENP1 polypeptide molecule or a SENP1 nucleic acid molecule. For example, the compound is an antibody that binds immunologically to a SENP1 polypeptide molecule or the compound is a nucleic acid sequence that hybridizes under stringent conditions to a SENP1 nucleic acid molecule. In certain embodiments, the hyperproliferative disease is further defined as a cancer, more particularly, the cancer is prostate cancer.

Still further, another embodiment of the present invention is a pharmaceutical composition comprising an inhibitor which is made by any of the methods described herein and is admixed with a pharmaceutical carrier.

Still further, another embodiment is a pharmaceutical composition comprising an inhibitor of the present invention admixed with a pharmaceutical carrier. The inhibitor can be a protein, a nucleic acid molecule, an organo-pharmaceutical, or a combination thereof. More specifically, the inhibitor is a nucleic acid molecule. More particularly, the nucleic acid molecule is an antisense molecule and/or an siRNA molecule. In certain embodiments, the inhibitor that is admixed with a pharmaceutical carrier comprises an siRNA molecule that is encoded by a nucleic acid sequence further defined as SEQ. ID. NO. 7.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIG. 1A shows an increased expression of SENP1 in high-grade prostate epithelial neoplasia (black arrow) compared with normal prostate epithelium (white arrow head) (40×). FIG. 1B shows an increased expression of SENP1 in prostate cancer (black arrow head) compared with normal prostate epithelium (white arrow head) (40×). FIG. 1C shows expression of SENP1 in prostate cancer (black arrow head) at high magnification (400×). Inset: negative control with sense SENP1 probe in normal prostate epithelium (white arrow head). FIG. 1D shows immunohistochemical staining of AR in normal prostate glands (white arrow head) and prostate cancer (black arrow head). These samples are representative of 25 tissue samples analyzed in a similar manner. FIG. 1E shows SENP1 expression in different cancer cell lines was measured by semi-quantitative RT-PCR.

FIG. 2A shows LNCaP cells that were treated with the synthetic androgen R1881 (20 nM) for either 24 or 48 hr. FIG. 2B shows LNCaP and PC-3 cells that were incubated with increasing concentrations of R1881 for 24 hr. FIG. 2C shows LNCaP cells that were treated with 20 nM R1881 in the presence or absence of the AR antagonist bicalutamide (5 μM). FIG. 2D shows LNCaP cells that were incubated with 25 ng/mL of IL-6, IL-4, or TNF-α for either 24 or 48 hr. FIG. 2E shows LNCaP or PC-3 cells that were treated with IL-6 (25 ng/mL) for 24 hr. IL-6-mediated upregulation of SENP1 occurred in LNCaP, but not PC-3 cells. FIG. 2F shows that the AR blocker bicalutamide (5 μM) lowers the enhanced SENP1 expression induced with chronic IL-6 exposure.

FIG. 3A shows that the SENP1 upregulation was synergized with co-administration of R1881 and IL-6. FIG. 3B shows the fold-increase in PSA (ng/mL) for each treatment (R1881 and 11-6 or a combination) as compared to control.

FIG. 5A shows PC-3 cells the effect of SENP1 on P-G4-cJun and G4-c-Jun dependent transcription. FIG. 5B shows the dependt effect of SENP1 on c-Jun dependent transcription. FIG. 5C shows Western blot analysis of the effect of wild-type SENP1 and mutant SENP1 on G4-c-Jun expression. FIG. 5D shows the effect of SENP1 on c-Jun promoter activity. FIG. 5E shows the effect of siRNA on c-Jun expression.

FIG. 6A shoes that overexpression of E1A pressed c-Jun-dependent transcription, while E1AΔ2-36, a p300 binding-defective mutant, did not. FIG. 6B shows that enhancement of G4-c-Jun transcription by SENP1 was impaired by co-expressing SENP1 and E1A. FIG. 6C shows that SENP1 is dependent on its catalytic activity.

FIG. 7A shows that deletion of the CRD1 domain increased the transactivation of p300. FIG. 7B shows that a p300 mutant transactivated G4-c-June more than the wild-type.

FIG. 8A shows that SENP1 desumoylates p300. FIG. 8B shows Gal4-DBD reporter system. FIG. 8C shows that deletion of the CRD1 domain increased p300 transactivation, whereas it impaired the effect of SENP1 on p300 transactivation. FIG. 8D shows that expression of SENP1, but not SENP1 mutant, completely reversed mCRD1 repression.

FIG. 9A and FIG. 9B show the effect of SENP1 on cyclin D1 expression. FIG. 9C shows the effect of SENP1 on cyclin D1 cell proliferation.

FIG. 10A shows enhancement of AR-dependent transcription by SENP1, but no by mutant SENP1. FIG. 10B shows dose response of SENP1 action. FIG. 10C shows SENP1 could not activated antagonist-bound AR. FIG. 10D shoes that SENP1, but not SENP2 or SENP3, markedly activates AR transactivation. FIGS. 10E and 10F show Western blots of cell extracts from FIG. 10B (FIG. 10E) and FIG. 10D (FIG. 10F). FIG. 10G shows that SENP1 enhances probasin promoter activity.

FIG. 1A shows that SENP1 induces endogenous AR-dependent transcription in LNCaP cells. FIG. 11B shows that SENP1 increases PSA expression in LNCaP cells. FIG. 11C shows that silencing endogenous SENP1 decreases PSA expression. FIG. 11D shows that endogenous SENP1 knocked down by RNAi.

FIG. 12A shows SENP1 physically interacts with HDAC1 in vivo. FIG. 12B shows that SENP1 deconjugates SUMP-1 from HDAC1 in vivo. FIGS. 12C and 12D show that SENP1 overcomes HDAC1's repressive activity. FIG. 12E shows that SENP1 reduces the deacetylase activity of HDAC1.

FIG. 13A shows that mutation of K444 and K476 relieves repression of HDAC1 on AR transactivation. FIG. 13B shows that endogenous HDAC1 is knocked down by RNAi. FIG. 13C shows that HDAC1 siRNA increases PSA expression. FIG. 13D shows that enhancement of AR-dependent transcription by SENP1 requires HDAC1.

FIG. 15A shows that PC-3 cells were transfected with non-specific siRNA or SENP1-siRNA. At 60 hr after re-plating the transfected cells, cyclin D1 protein was determined by western blot. FIGS. 15B and 15C show that LNCaP cells were stably transfected with empty vector, SENP1, or SENP1 mutant. Cyclin D1 protein (FIG. 15B) and mRNA level (FIG. 15C) were determined in these cell clones. FIG. 15D shows that vector-, SENP1-, or SENP1mut-LNCaP cells were treated with cycloheximide (20 cm). cyclin D1 protein level was determined at different time after treatment.

FIG. 16A shows a schematic diagram of cyclin D1 promoter used in these experiments. FIG. 16B and FIG. 16C show that PC-3 cells were co-transfected with CD1 (−1745/+134) and different dosage of SENP1 or SENP1 mutant plasmid. At 36 hr after transfection, luciferase activity (FIG. 16B) and SENP1 expression level (FIG. 16C) were determined. All luciferase activity was normalized to individually determined β-gal activity. FIG. 16D shows that luciferase activity was determined in PC-3 cells co-transfected with different CD1 promoters and, empty vector, SENP1, or SENP1 mutant plasmids. All luciferase activity was normalized to individually determined β-gal activity. FIG. 16E shows that luciferase activity was determined in PC-3 cells co-transfected with CD1 (−66/+134) wild-type and mutant promoters and empty vector, SENP1, or SENP1 mutant plasmids. All luciferase activity was normalized to individually determined β-gal activity.

FIG. 17A shows that PC-3 cells were co-transfected with CD1 (−1745/+134) and empty vector, SENP1, or SENP1 mutant plasmid. At 24 hr after transfection, cells were treated different dosage TSA as indicated for 12 hrs and then luciferase activity were determined. All luciferase activity was normalized to individually determined β-gal activity. FIG. 17B shows an empty vector, SENP1 or SENP1 mutant plasmids were transfected into PC-3 cells with CD1 (−1745/+134) in the presence of either HDAC-1 specific RNAi or non-specific RNAi control. After 48 hr of transfection, the Luciferase activity was measured. All luciferase activity was normalized to individually determined β-gal activity. FIG. 17C shows that PC-3 cells were co-transfected with CD1 (−1745/+134) plus SENP1, or SENP1 mutant, E1a, and E1AΔ2-36 as indicated, and luciferase activity was measured at 36 hr after transfection. All luciferase activity was normalized to individually determined β-gal activity.

FIG. 18D and FIG. 18E show that SENP1-LNCaP cells were transfected with non-specific siRNA or cyclin D1 siRNA (CCND1-siRNA). At day 4 after transfection, cyclin D1 expression and cell number were measured in these cells.

DETAILED DESCRIPTION OF THE INVENTION

I. Definitions

Figure 1:
FIG. 1A-FIG. 1E show upregulation of SENP1 selectively in prostate cancer and PIN, but not normal prostate tissues.
Figure 1:
Figure 1:
Figure 1:
Figure 1:
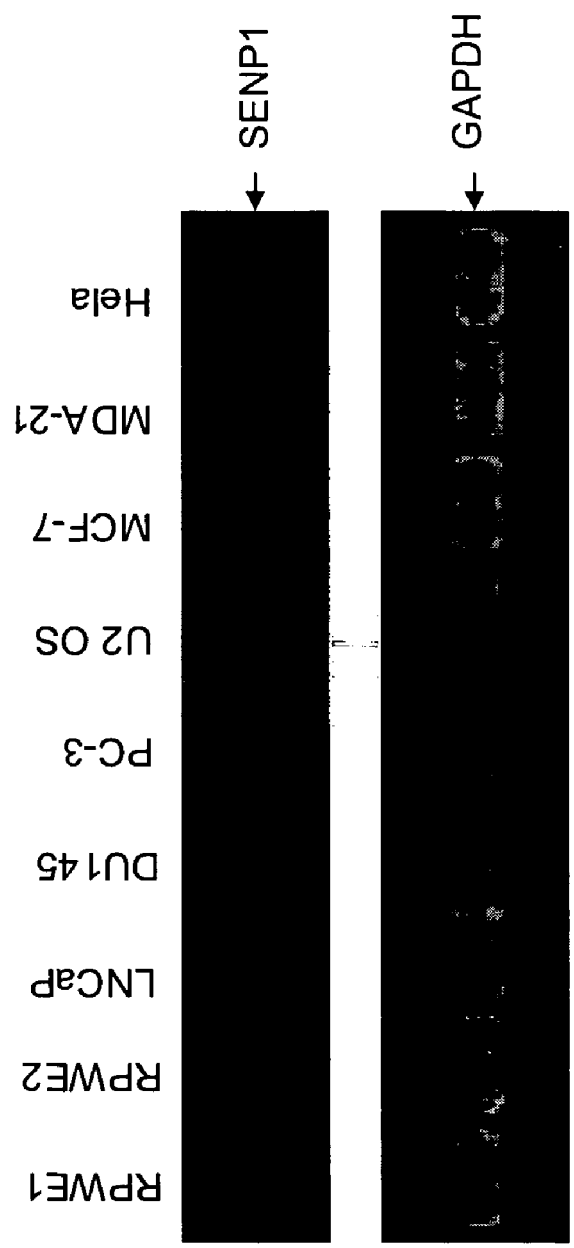

Unless defined otherwise, technical and scientific terms used herein have the same meaning as commonly understood by one of ordinary skill in the art to which this invention belongs. For purposes of the present invention, the following terms are defined below.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having", "including", "containing" and "comprising" are interchangeable and one of skill in the art is cognizant that these terms are open ended terms.

The term "androgen" as used herein refers to an agent that is typically a hormone (e.g., androsterone, testosterone) that stimulates activity of the male sex organs, encourages development of the male sex characteristics, etc. Androgens that are used in the present invention can be natural or native androgens, synthetic androgens or derivatives of androgens.

The term "androgen responsive" refers to a neoplasm that utilizes an androgen or a derivative thereof to develop, proliferative and/or metastasize. Yet further, as used herein, the terms "androgen responsive" and "androgen-dependent" are interchangeable.

The term "effective amount" as used herein is defined as an amount of the agent that will decrease, reduce, inhibit or otherwise abrogate the growth of a neoplasm, induce apoptosis, inhibit angiogenesis of a neoplasm, inhibit metastasis, or induce cytotoxicity in a neoplasm. Thus, an effective amount is an amount sufficient to detectably and repeatedly ameliorate, reduce, minimize or limit the extent of the disease or its symptoms.

The term "androgen receptor" or "AR" as used herein is a receptor that binds androgens. Androgen receptors are a member of the steroid nuclear-hormone-receptor (NHR) superfamily. These intracellular receptors are ligand-dependent transcription factors that regulate the transcription of a variety of genes. The AR is widely distributed among reproductive and non-reproductive tissues, including the prostate and seminal vesicles, male and female genitalia, skin, testis, ovary, cartilage, sebaceous glands, hair follicles, sweat glands, cardiac muscle, skeletal and smooth muscle, gastrointestinal vesicular cells, thyroid follicular cells, adrenal cortex, liver, pineal, and numerous brain cortical and subcortical regions, including spinal motor neurons (Negro-Vilar 1999; Sawaya et al., 1997; Roselli et al., 1998), and affect gene expression through the estrogen receptor.

The term "non-androgen responsive" refers to a neoplasm that does not utilize an androgen or a derivative thereof to develop, proliferative and/or metastasize. Yet further, as used herein, the terms "non-androgen responsive" and "androgen-independent" are interchangeable.

The term "cancer" as used herein is defined as a hyperproliferation of cells whose unique trait—loss of normal controls—results in unregulated growth, lack of differentiation, local tissue invasion, and metastasis. Examples include but are not limited to, melanoma, non-small cell lung, small-cell lung, lung, hepatocarcinoma, leukemia, retinoblastoma, astrocytoma, glioblastoma, gum, tongue, neuroblastoma, head, neck, breast, pancreatic, prostate, renal, bone, testicular, ovarian, mesothelioma, cervical, gastrointestinal, lymphoma, brain, colon, sarcoma or bladder.

The terms "cell," "cell line," and "cell culture" as used herein may be used interchangeably. All of these terms also include their progeny, which are any and all subsequent generations. It is understood that all progeny may not be identical due to deliberate or inadvertent mutations.

As used herein, the term "expression construct" or "transgene" is defined as any type of genetic construct containing a nucleic acid coding for gene products in which part or all of the nucleic acid encoding sequence is capable of being transcribed can be inserted into the vector. The transcript is translated into a protein, but it need not be. For example, the expression construct may comprise nucleic acid sequences encoding antisense molecules or siRNA molecules. In certain embodiments, expression includes both transcription of a gene and translation of mRNA into a gene product. In other embodiments, expression only includes transcription of the nucleic acid encoding genes of interest. In the present invention, the term "therapeutic construct" may also be used to refer to the expression construct or transgene. One skilled in the art realizes that the present invention utilizes the expression construct or transgene as a therapy to treat hyperproliferative diseases or disorders, such as cancer, thus the expression construct or transgene is a therapeutic construct or a prophylactic construct.

As used herein, the term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes or siRNA. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well and are described infra. In the present invention, the term "therapeutic vector" may also be used to refer to the expression vector. One skilled in the art realizes that the present invention utilizes the expression vector as a therapy to treat hyperproliferative diseases or disorders, such as cancer.

As used herein, the term "gene" is defined as a functional protein, polypeptide, or peptide-encoding unit. As will be understood by those in the art, this functional term includes genomic sequences, cDNA sequences, and smaller engineered gene segments that express, or is adapted to express, proteins, polypeptides, domains, peptides, fusion proteins, and mutants.

The term "hyperproliferative disease" is defined as a disease that results from a hyperproliferation of cells. Exemplary hyperproliferative diseases include, but are not limited to cancer or autoimmune diseases. Other hyperproliferative diseases may include vascular occulsion, restenosis, atherosclerosis, or inflammatory bowel disease.

The term "inhibitor" as used herein refers to a molecule or compound that acts to suppress the expression or function of another compound. More specifically, the "inhibitor" decreases the biological activity of a gene, an oligonucleotide, protein, enzyme, inhibitor, signal transducer, receptor, transcription activator, co-factor, and the like. Such inhibition may be contingent upon occurrence of a specific event, such as activation of a signal transduction pathway and/or may be manifest only in particular cell types. In specific embodiments, inhibitor decreases the ability of a cell to proliferate, for example a hyperproliferative cell or a neoplasm cell, etc.

The term "prostate" as used herein refers to the structure that surrounds the upper part of the urethra in a male or female.

The term "neoplasm" as used herein refers to an abnormal formation of tissue, for example, a tumor. One of skill in the art realizes that a neoplasm encompasses benign tumors and/or malignant tumors. Yet further, as used herein the terms "neoplasm" and "tumor" are interchangeable.

As used herein, the term "polynucleotide" is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means. Furthermore, one skilled in the art is cognizant that polynucleotides include mutations of the polynucleotides, include but are not limited to, mutation of the nucleotides, or nucleosides by methods well known in the art.

As used herein, the term "polypeptide" is defined as a chain of amino acid residues, usually having a defined sequence. As used herein the term polypeptide is interchangeable with the terms "peptides" and "proteins".

The term "treating" and "treatment" as used herein refers to administering to a subject an effective amount of an inhibitor of SENP1 so that the subject has an improvement in the disease. The improvement is any improvement or remediation of the symptoms. The improvement is an observable or measurable improvement. Thus, one of skill in the art realizes that a treatment may improve the disease condition, but may not be a complete cure for the disease.

As used herein, the term "healthy control" or "negative control" or "non-diseased" or "normal sample" refers to a biological sample obtained from a subject known not to be suffering from a hyperproliferative disorder or a sample obtained previously from the subject prior to the onset or suspicion of the a hyperproliferative disorder or a genetically-induced hyperproliferative disorder.

As used herein, the term "diseased control" or "positive control" or "test sample" refers to a biological sample obtained from a subject known to be suffering from a hyperproliferative disorder or a genetically-induced hyperproliferative disorder.

As used herein, the term "biological sample" refers to a sample that is obtained from a subject. More particular, the biological sample can be obtained from a blood sample, other body fluids, such as serum, urine, etc, a tissue biospy and/or aspiration of tissue or cells during a surgical procedure. Thus, the tissue may be part or separated from an organism. In certain embodiments, a tissue may comprise, but is not limited to, adipocytes, alveolar, ameloblasts, axon, basal cells, blood (e.g., lymphocytes), blood vessel, bone, bone marrow, brain, breast, cartilage, cervix, colon, cornea, embryonic, endometrium, endothelial, epithelial, esophagus, facia, fibroblast, follicular, ganglion cells, glial cells, goblet cells, kidney, liver, lung, lymph node, muscle, neuron, ovaries, pancreas, peripheral blood, prostate, skin, skin, small intestine, spleen, stem cells, stomach, testes, anthers, and ascite tissue.

As used herein, the term "diagnosis" refers to methods by which the skilled artisan can estimate and/or determine whether or not a subject is suffering from a given disease or condition. The skilled artisan often makes a diagnosis on the basis of one or more diagnostic markers, the presence, absence, or amount of which may be indicative of the presence, severity, or absence of the condition. In addition to markers, other tests, such as patient's history, sex, age, and race, may also be used in making the diagnosis.

II. Invention

It is well known that enhanced AR-dependent transcription promotes the manifestation of cancer, more particularly, prostate cancer. The present invention is the first to provide a link between the levels of SENP1 and the transcriptional activity of the AR. Yet further, it is envisioned that androgen-dependent and androgen-independent pathways increase SENP1 levels to further exacerbate elevated AR-dependent transcription.

The inventors have suggested that the enhanced expression of SENP1 is dependent on the presence of an AR. Thus the present invention relates to diagnosing hyperproliferating cells, more particularly, hyperproliferating cells that naturally express an AR, by measuring SENP1 levels. Yet further, an SENP1 inhibitor may be administered to a subject suffering from a hyperproliferative disease and/or an SENP1 inhibitor may be administered to a cell, more particularly, a tumor cell or a neoplasm, to inhibit cell proliferation.

It can be concluded that SENP1 expression is increased in most cases of a hyperproliferataive disease, for example, prostate cancer and precursor PIN areas. Androgen and IL-6 increase SENP1 expression, leading to enhancement of AR-dependent transcription. In addition, SENP1 increases c-Jun dependent transcription and cyclin-D1 expression. This combined AR-target gene activation and increase in cellular proliferative activity favors progression of tissue to development of a neoplasm. Thus, SENP1 is a novel link in the pathogenesis of cancer, which could serve as a potential target for cancer therapy, for example, inhibitors of SENP1.

III. SENP1 Inhibitors

In certain embodiments, inhibitors of SENP1 are administered to a subject to reduce or inhibit the activity and/or expression of SENP1. It is envisioned that SENP1 plays a role in AR transcription, cyclin D1 expression and c-Jun transcription.

The inhibitors of the present invention include, but are not limited to polynucleotides (RNA or DNA), polypeptides, antibodies, small molecules or other compositions that are capable of inhibiting either the activity and/or the expression of SENP1. Still further, other inhibitors of SENP1, include, but are not limited to compositions discussed in U.S. Pat. No. 6,596,527, which is incorporated herein by reference in its entirety.

In this patent, the terms "SENP1 gene product" refer to proteins and polypeptides having amino acid sequences that are substantially identical to the native SENP1 amino acid sequences (or RNA, if applicable) or that are biologically active, in that they are capable of performing functional activities similar to an endogenous SENP1 and/or cross-reacting with anti-SENP1 antibody raised against SENP1.

The terms "SENP1 gene product" also include related-compounds of the respective molecules that exhibit at least some biological activity in common with their native counterparts. Such related-compounds include, but are not limited to, truncated polypeptides and polypeptides having fewer amino acids than the native polypeptide. The SENP1 polypeptide sequences include, but are not limited to SEQ.ID.NO.1 (GenBank accession Q9POU3), and SEQ.ID.NO. 2 (GenBank accession No. AAH23129), more fully described in U.S. Pat. No. 6,596,527, which is incorporated herein by reference in its entirety.

The term "SENP1 gene" "SENP1 polynucleotide" or "SENP1 nucleic acid" refers to at least one molecule or strand of DNA (e.g., genomic DNA, cDNA) or RNA sequence (antisense RNA, siRNA) a derivative or mimic thereof, comprising at least one nucleotide base, such as, for example, a naturally occurring purine or pyrimidine base found in DNA (e.g., adenine "A," guanine "G," thymine "T," and cytosine "C") or RNA (e.g., A, G, uracil "U," and C). The term "nucleic acid" encompasses the terms "oligonucleotide" and "polynucleotide." These definitions generally refer to at least one single-stranded molecule, but in specific embodiments will also encompass at least one additional strand that is partially, substantially or fully complementary to the at least one single-stranded molecule. Thus, a nucleic acid may encompass at least one double-stranded molecule or at least one triple-stranded molecule that comprises one or more complementary strand(s) or "complement(s)" of a particular sequence comprising a strand of the molecule. An "isolated nucleic acid" as contemplated in the present invention may comprise transcribed nucleic acid(s), regulatory sequences, coding sequences, or the like, isolated substantially away from other such sequences, such as other naturally occurring nucleic acid molecules, regulatory sequences, polypeptide or peptide encoding sequences, etc.

More particularly, an "SENP1 gene or SENP1 polynucleotide" may also comprise any combination of associated control sequences. The SENP1 polynucleotide sequences include, but are not limited to SEQ.ID.NO. 3 (GenBank accession # AF149770) and SEQ.ID.NO. 4 (GenBank accession No. BC023129), more fully described in U.S. Pat. No. 6,596,527, which is incorporated herein by reference in its entirety. Thus, nucleic acid compositions encoding SENP1 are herein provided and are also available to a skilled artisan at accessible databases, including the National Center for Biotechnology Information's GenBank database and/or commercially available databases, such as from Celera Genomics, Inc. (Rockville, Md.). Also included are splice variants that encode different forms of the protein, if applicable. The nucleic acid sequences may be naturally occurring or synthetic.

Still further, the "SENP1 nucleic acid sequence," "SENP1 polynucleotide," and "SENP1 gene product" refer to nucleic acids provided herein, homologs therof, and sequences having substantial similarity and function, respectively. The term "substantially identical", when used to define either a SENP1 amino acid sequence or SENP1 polynucleotide sequence, means that a particular subject sequence, for example, a mutant sequence, varies from the sequence of natural SENP1, respectively, by one or more substitutions, deletions, or additions, the net effect of which is to retain at least some of the biological activity found in the native SENP1 protein, respectively. Alternatively, DNA analog sequences are "substantially identical" to specific DNA sequences disclosed herein if: (a) the DNA analog sequence is derived from coding regions of the natural SENP1 gene, respectively; or (b) the DNA analog sequence is capable of hybridization to DNA sequences of SENP1 under moderately stringent conditions and SENP1, respectively having biological activity similar to the native proteins; or (c) DNA sequences which are degenerative as a result of the genetic code to the DNA analog sequences defined in (a) or (b). Substantially identical analog proteins will be greater than about 80% similar to the corresponding sequence of the native protein. Sequences having lesser degrees of similarity but comparable biological activity are considered to be equivalents. In determining polynucleotide sequences, all subject polynucleotide sequences capable of encoding substantially similar amino acid sequences are considered to be substantially similar to a reference polynucleotide sequence, regardless of differences in codon sequence.

As used herein, "hybridization", "hybridizes" or "capable of hybridizing" is understood to mean the forming of a double or triple stranded molecule or a molecule with partial double or triple stranded nature. The term "hybridization", "hybridize(s)" or "capable of hybridizing" encompasses the terms "stringent condition(s)" or "high stringency" and the terms "low stringency" or "low stringency condition(s)" or "moderately stringent conditions".

As used herein "stringent condition(s)" or "high stringency" are those conditions that allow hybridization between or within one or more nucleic acid strand(s) containing complementary sequence(s), but precludes hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like.

Stringent conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride or other solvent(s) in a hybridization mixture.

It is also understood that these ranges, compositions and conditions for hybridization are mentioned by way of non-limiting examples only, and that the desired stringency for a particular hybridization reaction is often determined empirically by comparison to one or more positive or negative controls. Depending on the application envisioned it is preferred to employ varying conditions of hybridization to achieve varying degrees of selectivity of a nucleic acid towards a target sequence. In a non-limiting example, identification or isolation of a related target nucleic acid that does not hybridize to a nucleic acid under stringent conditions may be achieved by hybridization at low temperature and/or high ionic strength. For example, a medium or moderate stringency condition could be provided by about 0.1 to 0.25 M NaCl at temperatures of about 37° C. to about 55° C. Under these conditions, hybridization may occur even though the sequences of probe and target strand are not perfectly complementary, but are mismatched at one or more positions. In another example, a low stringency condition could be provided by about 0.15 M to about 0.9 M salt, at temperatures ranging from about 20° C. to about 55° C. Of course, it is within the skill of one in the art to further modify the low or high stringency conditions to suite a particular application. For example, in other embodiments, hybridization may be achieved under conditions of, 50 mM Tris-HCl (pH 8.3), 75 mM KCl, 3 mM MgCl2, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM MgCl$_2$, at temperatures ranging from approximately 40° C. to about 72° C.

Naturally, the present invention also encompasses nucleic acid sequences that are complementary, or essentially complementary, to the sequences set forth herein, for example, in SEQ ID NO:3 or SEQ ID NO:4. Nucleic acid sequences that are "complementary" are those that are capable of base-pairing according to the standard Watson-Crick complementarity rules. As used herein, the terms "complementary sequences" and "essentially complementary sequences" means nucleic acid sequences that are substantially complementary to, as may be assessed by the same nucleotide comparison set forth above, or are able to hybridize to a nucleic acid segment of one or more sequences set forth herein. Such sequences may encode an entire SENP1 molecule or functional or non-functional fragments thereof.

A. Expression Vectors

The present invention may involve using expression constructs as the pharmaceutical composition and/or diagnostic compositions. In certain embodiments, it is contemplated that the expression construct comprises polynucleotide sequences encoding polypeptides which can act as inhibitors of SENP1 and/or SENP1-related compounds or related-compounds, for example the expression construct may comprise a nucleic acid sequence encoding an antisense molecule or an siRNA molecule (e.g., SEQ. ID. NO. 7). One of skill of the would be able to determine depending upon the desired usage of the expression construct whether the polynucleotide sequences should encode a polypeptide that functions as an inhibitor of SENP1 (therapeutic protocols) or a SENP1-related compound (diagnostic protocols).

In certain embodiments, the present invention involves the manipulation of genetic material to produce expression constructs that encode inhibitors SENP1 and/or SENP1-related compounds. Thus, the SENP1 inhibitor and/or related-compound is contained in an expression vector. Such methods involve the generation of expression constructs containing, for example, a heterologous nucleic acid sequence encoding an inhibitor of interest and a means for its expression, replicating the vector in an appropriate cell, obtaining viral particles produced therefrom, and infecting cells with the recombinant virus particles.

As used in the present invention, the term "expression vector" refers to any type of genetic construct comprising a nucleic acid coding for SENP1 inhibitor and/or related compounds. In some cases, DNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra. It is contemplated in the present invention, that virtually any type of vector may be employed in any known or later discovered method to deliver nucleic acids encoding an inhibitor of SENP1 or related molecules. Where incorporation into an expression vector is desired, the nucleic acid encoding an SENP1 inhibitor or related molecule may also comprise a natural intron or an intron derived from another gene. Such vectors may be viral or non-viral vectors as described herein, and as known to those skilled in the art. An expression vector comprising a nucleic acid encoding an SENP1 inhibitor or related molecule may comprise a virus or engineered construct derived from a viral genome.

In particular embodiments of the invention, a plasmid vector is contemplated for use to transform a host cell. In general, plasmid vectors containing replicon and control sequences that are derived from species compatible with the host cell are used in connection with these hosts. The vector ordinarily carries a replication site, as well as marking sequences that are capable of providing phenotypic selection in transformed cells. Plasmid vectors are well known and are commercially available. Such vectors include, but are not limited to, the commercially available pSupervector (OligoEngine, Seattle, Wash.), pSuppressor Neo vector (IMGENEX Corporation) and pSilencer™ siRNA expression vectors (Ambion, Austin Tex.). Other vectors that may be employed in the present invention include, but are not limited to, the following eukaryotic vectors: pWLNEO, pSV2CAT, pOG44, PXT1, pSG (Stratagene) pSVK3, pBSK, pBR322, pUC vectors, vectors that contain markers that can be selected in mammalian cells, such as pCDNA3.1, episomally replicating vectors, such as the pREP series of vectors, pBPV, pMSG, pSVL (Pharmacia), adenovirus vector (AAV; pCWRSV, Chatterjee et al. (1992)); retroviral vectors, such as the pBABE vector series, a retroviral vector derived from MoMuLV (pG1Na, Zhou et al., (1994)); and pTZ18U (BioRad, Hercules, Calif.).

In one embodiment, a gene encoding an SENP1 inhibitor or structural/functional domain thereof or an SENP1-related compound is introduced in vivo in a viral vector. The ability of certain viruses to enter cells via receptor-mediated endocytosis and to integrate into the host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). Such vectors include an attenuated or defective DNA virus, such as but not limited to herpes simplex virus (HSV), papilloma virus, Epstein Barr virus (EBV), adenovirus, adeno-associated virus (AAV), lentivirus and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, any tissue can be specifically targeted. Examples of particular vectors include, but are not limited to, a defective herpes virus 1 (HSV1) vector (Kaplitt et al., 1991) an attenuated adenovirus vector, (Stratford-Perricaudet et al., 1992), and a defective adeno-associated virus vector (Samulski et al., 1987 and Samulski et al., 1989). Such vectors may be used to (i) transform cell lines in vitro for the purpose of expressing the SENP1 molecules or inhibitors thereof, such as antisense or siRNA molecules of the present invention or (ii) to transform cells in vitro or in vivo to provide therapeutic molecules for gene therapy. Thus, the present invention contemplates viral vectors such as, but not limited to, an adenoviral vector, an adeno-associated viral vector, a retroviral vector, a lentiviral vector, a herpes viral vector, polyoma viral vector or hepatitis B viral vector.

Preferably, for in vitro administration, an appropriate immunosuppressive treatment is employed in conjunction with the viral vector, e.g., adenovirus vector, to avoid immunodeactivation of the viral vector and transfected cells. For example, immunosuppressive cytokines, such as interleukin-12 (IL-12), interferon-γ (IFN-γ), or anti-CD4 antibody, can be administered to block humoral or cellular immune responses to the viral vectors (Wilson, Nature Medicine (1995). In addition, it is advantageous to employ a viral vector that is engineered to express a minimal number of antigens.

In another embodiment the gene can be introduced in a retroviral vector, e.g., as described in U.S. Pat. No. 5,399,346; Mann et al., 1983; U.S. Pat. No. 4,650,764; U.S. Pat. No. 4,980,289; Markowitz et al., 1988; U.S. Pat. No. 5,124,263; International Patent Publication No. WO 95/07358; and Kuo et al., 1993, each of which is incorporated herein by reference in its entirety. Targeted gene delivery is described in International Patent Publication WO 95/28494.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker. The use of cationic lipids may promote encapsulation of negatively charged nucleic acids, and also promote fusion with negatively charged cell membranes. The use of lipofection to introduce exogenous genes into the specific organs in vivo has certain practical advantages. Molecular targeting of liposomes to specific cells represents one area of benefit. Lipids may be chemically coupled to other molecules for the purpose of targeting. Targeted peptides, e.g., hormones or neurotransmitters, and proteins such as antibodies, or non-peptide molecules could be coupled to liposomes chemically.

It is also possible to introduce the vector in vivo as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter (Wu and Wu, 1988).

As used herein, the terms "cell," "cell line," and "cell culture" may be used interchangeably. All of these terms also include their progeny, which is any and all subsequent generations formed by cell division. It is understood that all progeny may not be identical due to deliberate or inadvertent mutations. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, SENP1 molecule or antisense or siRNA or a construct thereof. Therefore, recombinant cells are distinguishable from naturally occurring cells that do not contain a recombinantly introduced nucleic acid.

In certain embodiments, it is contemplated that nucleic acid or proteinaceous sequences may be co-expressed with other selected nucleic acid or proteinaceous sequences in the same host cell. Co-expression may be achieved by co-transfecting the host cell with two or more distinct recombinant vectors. Alternatively, a single recombinant vector may be constructed to include multiple distinct coding regions for nucleic acids, which could then be expressed in host cells transfected with the single vector.

A gene therapy vector as described above can employ a transcription control sequence operably associated with the sequence for the SENP1 inhibitor or related compound inserted in the vector. Such an expression vector is particularly useful to regulate expression of a therapeutic SENP1 inhibitor.

B. Transcription Factors and Nuclear Binding Sites

Transcription factors are regulatory proteins that binds to a specific DNA sequence (e.g., promoters and enhancers) and regulate transcription of an encoding DNA region. Typically, a transcription factor comprises a binding domain that binds to DNA (a DNA binding domain) and a regulatory domain that controls transcription. Where a regulatory domain activates transcription, that regulatory domain is designated an activation domain. Where that regulatory domain inhibits transcription, that regulatory domain is designated a repression domain.

Activation domains, and more recently repression domains, have been demonstrated to function as independent, modular components of transcription factors. Activation domains are not typified by a single consensus sequence but instead fall into several discrete classes: for example, acidic domains in GAL4 (Ma et al., 1987), GCN4 (Hope et al., 1987), VP16 (Sadowski et al., 1988), and GATA-1 (Martin, et al. 1990); glutamine-rich stretches in Sp1 (Courey et al., 1988) and Oct-2/OTF2 (Muller-Immergluck et al., 1990; Gerster et al., 1990); proline-rich sequences in CTF/NF-1 (Mermod et al., 1989); and serine/threonine-rich regions in Pit-1/GH-F-1 (Theill et al., 1989) all function to activate transcription. The activation domains of fos and jun are rich in both acidic and proline residues (Abate et al., 1991; Bohmann et al., 1989); for other activators, like the CCAAT/enhancer-binding protein C/EBP (Friedman et al., 1990), no evident sequence motif has emerged. More specifically, the activation domain can be classified as an androgen response element (ARE). ARE's include, but are not limited to DR-1 androgen response elements, C3, PSA-AREs or probasin-AREs, or promoters containing glucocorticoid response elements, progesterone response elements, mineralocorticoid response elements or estradiol response elements (US20040068762, which is incorporated herein by reference).

Thus, in the present invention, it is contemplated that transcription factors can be used to inhibit the expression of SENP1.

C. Antisense and Ribozymes

An antisense molecule that binds to a translational or transcriptional start site, or splice junctions, are ideal inhibitors. Antisense, ribozyme, and double-stranded RNA molecules target a particular sequence to achieve a reduction or elimination of a particular polypeptide, such as SENP1. Thus, it is contemplated that antisense, ribozyme, and double-stranded RNA, and RNA interference molecules are constructed and used to inhibit SENP1.

1. Antisense Molecules

Antisense methodology takes advantage of the fact that nucleic acids tend to pair with complementary sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNAs, are employed to inhibit gene transcription or translation or both within a host cell, either in vitro or in vivo, such as within a host animal, including a human subject.

Antisense constructs are designed to bind to the promoter and other control regions, exons, introns or even exon-intron boundaries of a gene. It is contemplated that the most effective antisense constructs may include regions complementary to intron/exon splice junctions. Thus, antisense constructs with complementarity to regions within 50-200 bases of an intron-exon splice junction are used. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

It is advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

2. RNA Interference

It is also contemplated in the present invention that double-stranded RNA is used as an interference molecule, e.g., RNA interference (RNAi). RNA interference is used to "knock down" or inhibit a particular gene of interest by simply injecting, bathing or feeding to the organism of interest the double-stranded RNA molecule. This technique selectively "knock downs" gene function without requiring transfection or recombinant techniques (Giet, 2001; Hammond, 2001; Stein P, et al., 2002; Svoboda P, et al., 2001; Svoboda P, et al., 2000).

Another type of RNAi is often referred to as small interfering RNA (siRNA), which may also be utilized to inhibit SENP1. A siRNA may comprises a double stranded structure or a single stranded structure, the sequence of which is "substantially identical" to at least a portion of the target gene (See WO 04/046320, which is incorporated herein by reference in its entirety). "Identity," as known in the art, is the relationship between two or more polynucleotide (or polypeptide) sequences, as determined by comparing the sequences. In the art, identity also means the degree of sequence relatedness between polynucleotide sequences, as determined by the match of the order of nucleotides between such sequences. Identity can be readily calculated. See, for example: Computational Molecular Biology, Lesk, A. M., ed. Oxford University Press, New York, 1988; Biocomputing: Informatics and Genome Projects, Smith, D. W., ea., Academic Press, New York, 1993, and the methods disclosed in WO 99/32619, WO 01/68836, WO 00/44914, and WO 01/36646, specifically incorporated herein by reference. While a number of methods exist for measuring identity between two nucleotide sequences, the term is well known in the art. Methods for determining identity are typically designed to produce the greatest degree of matching of nucleotide sequence and are also typically embodied in computer programs. Such programs are readily available to those in the relevant art. For example, the GCG program package (Devereux et al.), BLASTP, BLASTN, and FASTA (Atschul et al.) and CLUSTAL (Higgins et al., 1992; Thompson, et al., 1994).

Thus, siRNA contains a nucleotide sequence that is essentially identical to at least a portion of the target gene, SENP1. More particularly, the siRNA molecule contains a nucleotide sequence that is essentially identical to at least a portion of SEQ. ID. NO. 3 and/or SEQ. ID. NO. 4. Preferably, the siRNA contains a nucleotide sequence that is completely identical to at least a portion of the target gene. Of course, when comparing an RNA sequence to a DNA sequence, an "identical" RNA sequence will contain ribonucleotides where the DNA sequence contains deoxyribonucleotides, and further that the RNA sequence will typically contain a uracil at positions where the DNA sequence contains thymidine. In particular embodiments, the siRNA molecule comprises SEQ. ID. NO. 7.

One of skill in the art will appreciate that two polynucleotides of different lengths may be compared over the entire length of the longer fragment. Alternatively, small regions may be compared. Normally sequences of the same length are compared for a final estimation of their utility in the practice of the present invention. It is preferred that there be 100% sequence identity between the dsRNA for use as siRNA and at least 15 contiguous nucleotides of the target gene (e.g., SENP1), although a dsRNA having 70%, 75%, 80%, 85%, 90%, or 95% or greater may also be used in the present invention. A siRNA that is essentially identical to a least a portion of the target gene may also be a dsRNA wherein one of the two complementary strands (or, in the case of a self-complementary RNA, one of the two self-complementary portions) is either identical to the sequence of that portion or the target gene or contains one or more insertions, deletions or single point mutations relative to the nucleotide sequence of that portion of the target gene. siRNA technology thus has the property of being able to tolerate sequence variations that might be expected to result from genetic mutation, strain polymorphism, or evolutionary divergence.

There are several methods for preparing siRNA, such as chemical synthesis, in vitro transcription, siRNA expression vectors, and PCR expression cassettes. Irrespective of which method one uses, the first step in designing an siRNA molecule is to choose the siRNA target site, which can be any site in the target gene. In certain embodiments, one of skill in the art may manually select the target selecting region of the gene, which may be an ORF (open reading frame) as the target selecting region and may preferably be 50-100 nucleotides downstream of the "ATG" start codon. However, there are several readily available programs available to assist with the design of siRNA molecules, for example siRNA Target Designer by Promega, siRNA Target Finder by GenScript Corp., siRNA Retriever Program by Imgenex Corp., EMBOSS siRNA algorithm, siRNA program by Qiagen, Ambion siRNA predictor, Ambion siRNA predictor, Whitehead siRNA prediction, and Sfold. Thus, it is envisioned that any of the above programs may be utilized to produce siRNA molecules that can be used in the present invention.

3. Ribozymes

Ribozymes are RNA-protein complexes that cleave nucleic acids in a site-specific fashion. Ribozymes have specific catalytic domains that possess endonuclease activity (Kim and Cech, 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence specific cleavage/ligation reactions involving nucleic acids (Joyce, 1989; Cech et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression is particularly suited to therapeutic applications (Scanlon et al., 1991; Sarver et al., 1990; Sioud et al., 1992). Most of this work involved the modification of a target mRNA, based on a specific mutant codon that is cleaved by a specific ribozyme. In light of the information included herein and the knowledge of one of ordinary skill in the art, the preparation and use of additional ribozymes that are specifically targeted to a given gene will now be straightforward.

Other suitable ribozymes include sequences from RNase P with RNA cleavage activity (Yuan et al., 1992; Yuan and Altman, 1994), hairpin ribozyme structures (Berzal-Herranz et al., 1992; Chowrira et al., 1993) and hepatitis 6 virus based ribozymes (Perrotta and Been, 1992). The general design and optimization of ribozyme directed RNA cleavage activity has been discussed in detail (Haseloff and Gerlach, 1988; Symons, 1992; Chowrira, et al., 1994; and Thompson, et al., 1995).

The other variable on ribozyme design is the selection of a cleavage site on a given target RNA. Ribozymes are targeted to a given sequence by virtue of annealing to a site by complimentary base pair interactions. Two stretches of homology are required for this targeting. These stretches of homologous sequences flank the catalytic ribozyme structure defined above. Each stretch of homologous sequence can vary in length from 7 to 15 nucleotides. The only requirement for defining the homologous sequences is that, on the target RNA, they are separated by a specific sequence which is the cleavage site. For hammerhead ribozymes, the cleavage site is a dinucleotide sequence on the target RNA, uracil (U) followed by either an adenine, cytosine or uracil (A, C or U; Perriman, et al., 1992; Thompson, et al., 1995). The frequency of this dinucleotide occurring in any given RNA is statistically 3 out of 16.

Designing and testing ribozymes for efficient cleavage of a target RNA is a process well known to those skilled in the art. Examples of scientific methods for designing and testing ribozymes are described by Chowrira et al. (1994) and Lieber and Strauss (1995), each incorporated by reference. The identification of operative and preferred sequences for use in Chk2 targeted ribozymes is simply a matter of preparing and testing a given sequence, and is a routinely practiced screening method known to those of skill in the art.

D. Protein Variants

Amino acid sequence variants of the SENP1 can be used as inhibitors of SENP1 activity. These variants can be substitutional, insertional or deletion variants. These variants may be purified according to known methods, such as precipitation (e.g., ammonium sulfate), HPLC, ion exchange chromatography, affinity chromatography (including immunoaffinity chromatography) or various size separations (sedimentation, gel electrophoresis, gel filtration).

Substitutional variants or replacement variants typically contain the exchange of one amino acid for another at one or more sites within the protein. Substitutions can be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

It is thus contemplated by the inventors that various changes may be made in the DNA sequences of genes without appreciable loss of their biological utility or activity, as discussed below. The activity being activation of AR transcription and/or cyclin D1 expression and/or c-Jun transcription, etc.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine −0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtains a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

1. Fusion Proteins

A specialized kind of insertional variant is the fusion protein. This molecule generally has all or a substantial portion of the native molecule, linked at the N- or C-terminus, to all or a portion of a second polypeptide. For example, a fusion protein of the present invention can includes the addition of a protein transduction domains, for example, but not limited to Antennepedia transduction domain (ANTP), HSV1 (VP22)

and HIV-1 (Tat). Fusion proteins containing protein transduction domains (PTDs) can traverse biological membranes efficiently, thus delivering the protein of interest into the cell.

Yet further, inclusion of a cleavage site at or near the fusion junction will facilitate removal of the extraneous polypeptide after purification. Other useful fusions include linking of functional domains, such as active sites from enzymes, glycosylation domains, other cellular targeting signals or transmembrane regions.

2. Domain Switching

An interesting series of variants can be created by substituting homologous regions of various proteins. This is known, in certain contexts, as "domain switching."

Domain switching involves the generation of chimeric molecules using different but, in this case, related polypeptides. By comparing various SENP1 proteins, one can make predictions as to the functionally significant regions of these molecules. It is possible, then, to switch related domains of these molecules in an effort to determine the criticality of these regions to function of the protein. These molecules may have additional value in that these "chimeras" can be distinguished from natural molecules, while possibly providing the same function.

3. Synthetic Peptides

The present invention also describes smaller SENP1-related peptides for use in various embodiments of the present invention. Because of their relatively small size, the peptides of the invention can also be synthesized in solution or on a solid support in accordance with conventional techniques. Various automatic synthesizers are commercially available and can be used in accordance with known protocols. See, for example, Stewart and Young (1984); Tam et al. (1983); Merrifield (1986); and Barany and Merrifield (1979), each incorporated herein by reference. Short peptide sequences, or libraries of overlapping peptides, usually from about 6 up to about 35 to 50 amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression.

IV. Methods of Manufacturing Inhibitors

The present invention comprises methods for manufacturing inhibitors that affect the activity and/or expression of SENP1. These methods may comprise random screening of large libraries of candidate substances; alternatively, the methods may be used to focus on particular classes of compounds selected with an eye towards structural attributes that are believed to make them more likely to modulate the function or activity or expression of SENP1. Yet further, the present invention encompasses inhibitors identified in U.S. Pat. No. 6,596,527, which is incorporated herein by reference in its entirety.

By function, it is meant that one may assay for mRNA expression, protein expression, protein activity, binding activity, or ability to associate and/or dissociate from other members of the complex and otherwise determine functions contingent on the SENP1 proteins or nucleic acid molecules.

A. Inhibitors

The present invention further comprises methods for identifying, making, generating, providing, manufacturing or obtaining inhibitors of SENP1 activity or expression. SENP1 nucleic acid or polypeptide may be used as a target in identifying compounds that inhibit, decrease or down-regulate its expression or activity in cancer cells, such as lung cancer cells. In other embodiments, compounds screened for would decrease AR dependent transcription, c-Jun dependent transcription, and/or cyclin D1 transcription in a cancer cell. These assays may comprise random screening of large libraries of candidate substances; alternatively, the assays may be used to focus on particular classes of compounds selected with an eye towards structural attributes that are believed to make them more likely to inhibit the function of delta SENP1 molecules. By function, it is meant that one may assay for inhibition of activity of SENP1 in cancer cells, or inhibition of expression of SENP1, for example. Such assays may include for example luciferase reportor system in which luceiferase activity is measured or in vitro assays that measure protease activity.

To identify, make, generate, provide, manufacture or obtain a SENP1 inhibitor, one generally will determine the activity of the SENP1 molecule in the presence, absence, or both of the candidate substance, wherein an inhibitor is defined as any substance that down-regulates, reduces, inhibits or decreases SENP1 expression or activity. For example, a method may generally comprise:

(a) providing a candidate substance suspected of decreasing SENP1 expression or activity;

(b) assessing the ability of the candidate substance to decrease SENP1 expression or activity;

(c) selecting an SENP1 inhibitor; and (d) manufacturing the inhibitor.

In further embodiments, a SENP1 polypeptide or nucleic acid may be provided in a cell or a cell free system and the SENP1 polypeptide or nucleic acid may be contacted with the candidate substance. Next, an inhibitor is selected by assessing the effect of the candidate substance on SENP1 activity or SENP1 expression. Upon identification of the inhibitor, the method may further provide the step of manufacturing of the inhibitor using well known techniques in the art, such as synthesizing the compound or deriving the compound from a natural source.

As used herein, the term "candidate substance" refers to any molecule that may potentially inhibit SENP1 activity, expression or function. Candidate compounds may include fragments or parts of naturally-occurring compounds or may be found as active combinations of known compounds which are otherwise inactive. The candidate substance can be a nucleic acid (e.g., antisense molecule, siRNA molecule), a polypeptide (e.g., antibodies), a small molecule, etc. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds.

One basic approach to search for a candidate substance is screening of compound libraries. One may simply acquire, from various commercial sources, small molecule libraries that are believed to meet the basic criteria for useful drugs in an effort to "brute force" the identification of useful compounds. Screening of such libraries, including combinatorially generated libraries, is a rapid and efficient way to screen a large number of related (and unrelated) compounds for activity. Combinatorial approaches also lend themselves to rapid evolution of potential drugs by the creation of second, third and fourth generation compounds modeled of active, but otherwise undesirable compounds. It will be understood that an undesirable compound includes compounds that are typically toxic, but have been modified to reduce the toxicity or compounds that typically have little effect with minimal toxicity and are used in combination with another compound to produce the desired effect.

In specific embodiments, a small molecule library that is created by chemical genetics may be screened to identify a candidate substance that may be a modulator of the present invention (Clemons et al., 2001; Blackwell et al., 2001). Chemical genetics is the technology that uses small molecules to modulate the functions of proteins rapidly and conditionally. The basic approach requires identification of compounds that regulate pathways and bind to proteins with high specificity. Small molecules are prepared using diversity-oriented synthesis, and the split-pool strategy to allow spatial segregation on individual polymer beads. Each bead contains compounds to generate a stock solution that can be used for many biological assays.

The most useful pharmacological compounds may be compounds that are structurally related to compounds which interact naturally with compounds that modulate SENP1 transcription or activity. Creating and examining the action of such molecules is known as "rational drug design," and include making predictions relating to the structure of target molecules. Thus, it is understood that the candidate substance identified by the present invention may be a small molecule activator or any other compound (e.g., polypeptide or polynucleotide) that may be designed through rational drug design starting from known inhibitors of SENP1.

The goal of rational drug design is to produce or manufacture structural analogs of biologically active target compounds. By creating such analogs, it is possible to fashion drugs which are more active or stable than the natural molecules, which have different susceptibility to alteration or which may affect the function of various other molecules. In one approach, one would generate a three-dimensional structure for a molecule similar to SENP1, and then design a molecule for its ability to interact with an SENP1-related molecule. This could be accomplished by X-ray crystallography, computer modeling or by a combination of both approaches. The same approach may be applied to identifying interacting molecules of SENP1.

It also is possible to use antibodies to ascertain the structure of a target compound or activator. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

It will, of course, be understood that all the screening methods of the present invention are useful in themselves notwithstanding the fact that effective candidates may not be found. The invention provides methods for screening for such candidates, not solely methods of finding them.

B. In Vitro Assays

A quick, inexpensive and easy assay to run is a binding assay. Binding of a molecule to a target (e.g., SENP1) may, in and of itself, be inhibitory, due to steric, allosteric or charge-charge interactions. This can be performed in solution or on a solid phase and can be utilized as a first round screen to rapidly eliminate certain compounds before moving into more sophisticated screening assays. In one embodiment of this kind, the screening of compounds that bind to SENP1 molecules or fragments thereof are provided.

A target SENP1 protein may be either free in solution, fixed to a support, expressed in or on the surface of a cell. Either the SENP1 protein or the compound may be labeled, thereby indicating if binding has occurred. In another embodiment, the assay may measure the activation of SENP1 to a natural or artificial substrate or binding partner. Competitive binding assays can be performed in which one of the agents is labeled. Usually, the target SENP1 protein will be the labeled species, decreasing the chance that the labeling will interfere with the binding moiety's function. One may measure the amount of free label versus bound label to determine binding or activation of binding. These approaches may be utilized on SENP1 molecules.

A technique for high throughput screening of compounds is described in WO 84/03564. Large numbers of small peptide test compounds are synthesized on a solid substrate, such as plastic pins or some other surface. The peptide test compounds are reacted with, for example, SENP1 protein and washed. Bound polypeptide is detected by various methods.

C. In Cyto Assays

Various cell lines that express telomere associated proteins can be utilized for screening of candidate substances. For example, cells containing SENP1 proteins with an engineered indicator can be used to study various functional attributes of candidate compounds. In such assays, the compound would be formulated appropriately, given its biochemical nature, and contacted with a target cell. This same approach may utilized to study various functional attributes of candidate compounds that effect SENP1.

Depending on the assay, culture may be required. As discussed above, the cell may then be examined by virtue of a number of different physiologic assays (e.g., growth, size, or survival). Alternatively, molecular analysis may be performed in which the function of SENP1 and SENP1 related pathways may be explored. This involves assays such as those for protein production, enzyme function, substrate utilization, mRNA expression (including differential display of whole cell or polyA RNA) and others.

D. In Vivo Assays

The present invention particularly contemplates the use of various animal models. Transgenic animals can be made by any known procedure, including microinjection methods, and embryonic stem cells methods. The procedures for manipulation of the rodent embryo and for microinjection of DNA are described in detail in Hogan et al., Manipulating the Mouse Embryo (Cold Spring Harbor Laboratory, Cold Spring Harbor, N.Y., 1986), and U.S. Pat. No. 6,201,165, the teachings of which are generally known and are incorporated herein.

Treatment of animals with test compounds (e.g., inhibitors of SENP1) involve the administration of the compound, in an appropriate form, to the animal. Administration is by any route that could be utilized for clinical or non-clinical purposes, including but not limited to oral, nasal, buccal, or even topical. Alternatively, administration may be by intratracheal instillation, bronchial instillation, intradermal, subcutaneous, intramuscular, intraperitoneal or intravenous injection. Specifically contemplated are systemic intravenous injection, regional administration via blood or lymph supply.

E. Production of Inhibitors

In an extension of any of the previously described screening assays, the present invention also provide for methods of producing or manufacturing inhibitors of SENP1. The methods comprising any of the preceding screening steps followed by an additional step of "producing or manufacturing the candidate substance identified as an inhibitor of" the screened activity. Manufacturing can entail any well known and standard technique used by those of skill in the art, such as synthesizing the compound and/or deriving the compound from a natural source.

V. Methods of Treatment Using the SENP1 Inhibitors

In certain aspects of the present invention, SENP1 inhibitors or related-compounds thereof are administered to cells to inhibit cell proliferation. In further embodiments, the present invention encompasses the SENP1 inhibitors of U.S. Pat. No. 6,596,527, which is incorporated herein by reference in its entirety, to treat diseases in which excess SENP1 expression or activity is deleterious or harmful.

With the administration of an SENP1 inhibitor, cell proliferation is abrogated, slowed, reduced or inhibited due to the decrease in SENP1 transcription and/or activity which results in a decrease in AR transcription, as well as a decrease in c-Jun transcription and cyclin D1 expression. Such cells in which the SENP1 inhibitors may be administered may include any cell that naturally expresses an androgen receptor or are considered androgen receptor positive cells. The AR is widely distributed among reproductive and non-reproductive tissues, including the prostate and seminal vesicles, male and female genitalia, skin, testis, ovary, cartilage, sebaceous glands, hair follicles, sweat glands, cardiac muscle, skeletal and smooth muscle, gastrointestinal vesicular cells, thyroid follicular cells, adrenal cortex, liver, pineal, and numerous brain cortical and subcortical regions, including spinal motor neurons.

In certain embodiments of the present invention, the cells are prostate cells. Prostate cells include cancer cell, non-cancerous cells or benign hyperplastic cells (e.g., prostatic intrapithelial neoplasia cells, prostatic primary tumor cells and prostatic metastatic tumor cells). Other cells as contemplated in the present invention may be a cancer cell such as, but not limited to, a breast cancer cell, lung cancer cell, head and neck cancer cell, bladder cancer cell, bone cancer cell, bone marrow cancer cell, brain cancer cell, colon cancer cell, esophageal cancer cell, gastrointestinal cancer cell, gum cancer cell, kidney cancer cell, liver cancer cell, nasopharynx cancer cell, ovarian cancer cell, skin cancer cell, stomach cancer cell, testis cancer cell, tongue cancer cell, or uterine cancer cell.

An effective amount of an SENP1 inhibitor that may be administered to a cell includes a dose of about 0.1 µM to about 100 µM. More specifically, doses of an SENP1 inhibitor to be administered are from about 0.1 µM to about 10 µM; about 1 µM to about 5 µM; about 5 µM to about 10 µM; about 10 µM to about 15 µM; about 15 µM to about 20 µM; about 20 µM to about 30 µM; about 30 µM to about 40 µM; about 40 µM to about 50 µM; about 50 µM to about 60 µM; about 60 µM to about 70 µM; about 70 µM to about 80 µM; about 80 µM to about 90 µM; and about 90 µM to about 100 µM. Of course, all of these amounts are exemplary, and any amount in-between these points is also expected to be of use in the invention.

It is envisioned that the SENP1 inhibitor or related-compound thereof will inhibit the proliferation of a cell or growth of a neoplasm by measurably slowing, stopping, or reversing the growth rate of the cell or neoplasm or neoplastic cells in vitro or in vivo. Desirably, the growth rate is slowed by 20%, 30%, 50%, or 70% or more, as determined using a suitable assay for determination of cell growth rates.

Still further, the present invention provides methods for the treatment of a hyperproliferative disease by administering an SENP1 inhibitor (e.g., siRNA and/or a small molecule). The SENP1 inhibitor or related-compound thereof can be administered parenterally or alimentary. Parenteral administrations include, but are not limited to intravenously, intradermally, intramuscularly, intraarterially, intrathecally, subcutaneous, or intraperitoneally U.S. Pat. Nos. 6,613,308, 5,466,468, 5,543,158; 5,641,515; and 5,399,363 (each specifically incorporated herein by reference in its entirety). Alimentary administrations include, but are not limited to orally, buccally, rectally, or sublingually.

In certain embodiments, a hyperproliferative disease is further defined as cancer. In still further embodiments, the cancer is melanoma, non-small cell lung, small-cell lung, lung, leukemia, hepatocarcinoma, retinoblastoma, astrocytoma, glioblastoma, gum, tongue, neuroblastoma, head, neck, breast, pancreatic, prostate, renal, bone, testicular, ovarian, mesothelioma, cervical, gastrointestinal, lymphoma, brain, colon, sarcoma or bladder. More particularly, the cancer is prostate cancer.

In other embodiments, the hyperproliferative disease is rheumatoid arthritis, inflammatory bowel disease, osteoarthritis, leiomyomas, adenomas, lipomas, hemangiomas, fibromas, vascular occlusion, restenosis, atherosclerosis, pre-neoplastic lesions (such as adenomatous hyperplasia and prostatic intraepithelial neoplasia), carcinoma in situ, oral hairy leukoplakia, or psoriasis. Other hyperproliferative disease include, colon polyps, Crohn's disease, ulcerative colitis, breast lesions and the like.

Treatment methods will involve treating an individual with an effective amount of a composition containing an SENP1 inhibitor or related-compound thereof. An effective amount is described, generally, as that amount sufficient to detectably and repeatedly to ameliorate, reduce, minimize or limit the extent of a disease or its symptoms. More specifically, it is envisioned that the treatment with the inhibitor of SENP1 or related-compounds thereof will kill cells, inhibit cell growth, inhibit cell proliferation, inhibit metastasis, decrease tumor size and otherwise reverse or reduce the malignant phenotype of tumor cells.

In further aspects, an effective amount of an SENP1 inhibitor or related-compound thereof may be administered to a subject suffering from prostate cancer, more specifically, recurrent prostate cancer. The effectiveness of SENP1 inhibitor therapy according to the present invention can be determined in the treatment of prostate cancer by diagnostic methods that are known and used in the art, for example, but not limited to, analysis of prostate specific antigen (PSA), a prostate biopsy, a rectal exam, or analysis of PSA and rectal exam.

Other embodiments include methods for inhibiting development of prostate cancer in a subject at risk, inhibiting prostate cancer metastasis in a subject with primary prostate cancer, and/or inhibiting prostate cancer progression in subjects having Stage 1 or Stage 2 prostate cancer.

The effective amount or "therapeutically effective amounts" of the inhibitor of SENP1 or related-compounds thereof to be used are those amounts effective to produce beneficial results, particularly with respect to cancer treatment, in the recipient animal or patient. Such amounts may be initially determined by reviewing the published literature, by conducting in vitro tests or by conducting metabolic studies in healthy experimental animals. Before use in a clinical setting, it may be beneficial to conduct confirmatory studies in an animal model, preferably a widely accepted animal model of the particular disease to be treated. Preferred animal models for use in certain embodiments are rodent models, which are preferred because they are economical to use and, particularly, because the results gained are widely accepted as predictive of clinical value.

As is well known in the art, a specific dose level of active compounds such as an SENP1 inhibitor or related-compounds thereof for any particular patient depends upon a variety of factors including the activity of the specific compound employed, the age, body weight, general health, sex, diet, time of administration, route of administration, rate of excretion, drug combination, and the severity of the particular disease undergoing therapy. The person responsible for administration will determine the appropriate dose for the individual subject. Moreover, for human administration, preparations should meet sterility, pyrogenicity, general safety and purity standards as required by FDA Office of Biologics standards.

A therapeutically effective amount of an SENP1 inhibitor or related-compounds thereof as a treatment varies depending upon the host treated and the particular mode of administration. In one embodiment of the invention the dose range of the SENP1 inhibitor or related-compounds thereof will be about 0.5 mg/kg body weight to about 500 mg/kg body weight. The term "body weight" is applicable when an animal is being treated. When isolated cells are being treated, "body weight" as used herein should read to mean "total cell body weight". The term "total body weight" may be used to apply to both isolated cell and animal treatment. All concentrations and treatment levels are expressed as "body weight" or simply "kg" in this application are also considered to cover the analogous "total cell body weight" and "total body weight" concentrations. However, those of skill will recognize the utility of a variety of dosage range, for example, 1 mg/kg body weight to 450 mg/kg body weight, 2 mg/kg body weight to 400 mg/kg body weight, 3 mg/kg body weight to 350 mg/kg body weight, 4 mg/kg body weight to 300 mg/kg body weight, 5 mg/kg body weight to 250 mg/kg body weight, 6 mg/kg body weight to 200 mg/kg body weight, 7 mg/kg body weight to 150 mg/kg body weight, 8 mg/kg body weight to 100 mg/kg body weight, or 9 mg/kg body weight to 50 mg/kg body weight. Further, those of skill will recognize that a variety of different dosage levels will be of use, for example, 1 mg/kg, 2 mg/kg, 3 mg/kg, 4 mg/kg, 5 mg/kg, 7.5 mg/kg, 10 mg/kg, 12.5 mg/kg, 15 mg/kg, 17.5 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 120 mg/kg, 140 mg/kg, 150 mg/kg, 160 mg/kg, 180 mg/kg, 200 mg/kg, 225 mg/kg, 250 mg/kg, 275 mg/kg, 300 mg/kg, 325 mg/kg, 350 mg/kg, 375 mg/kg, 400 mg/kg, 450 mg/kg, 500 mg/kg, 550 mg/kg, 600 mg/kg, 700 mg/kg, 750 mg/kg, 800 mg/kg, 900 mg/kg, 1000 mg/kg, 1250 mg/kg, 1500 mg/kg, 1750 mg/kg, 2000 mg/kg, 2500 mg/kg, and/or 3000 mg/kg. Of course, all of these dosages are exemplary, and any dosage in-between these points is also expected to be of use in the invention. Any of the above dosage ranges or dosage levels may be employed for an SENP1 inhibitor or related-compounds thereof.

Administration of the therapeutic SENP1 inhibitor composition of the present invention to a patient or subject will follow general protocols for the administration of chemotherapeutics, taking into account the toxicity, if any, of the SENP1 inhibitor. It is expected that the treatment cycles would be repeated as necessary. It also is contemplated that various standard therapies, as well as surgical intervention, may be applied in combination with the described therapy.

The treatments may include various "unit doses." Unit dose is defined as containing a predetermined quantity of the therapeutic composition (an SENP1 inhibitor or its related-compounds thereof) calculated to produce the desired responses in association with its administration, i.e., the appropriate route and treatment regimen. The quantity to be administered, and the particular route and formulation, are within the skill of those in the clinical arts. Also of import is the subject to be treated, in particular, the state of the subject and the protection desired. A unit dose need not be administered as a single injection but may comprise continuous infusion over a set period of time.

According to the present invention, one may treat the cancer by directly injection a tumor with the SENP1 inhibitor or related-compound composition. Alternatively, the tumor may be infused or perfused with the composition using any suitable delivery vehicle. Local or regional administration, with respect to the tumor, also is contemplated. More preferably, systemic administration or oral administration may be performed. Continuous administration also may be applied where appropriate, for example, where a tumor is excised and the tumor bed is treated to eliminate residual, microscopic disease. Delivery via syringe or catherization is preferred. Such continuous perfusion may take place for a period from about 1-2 hours, to about 2-6 hours, to about 6-12 hours, to about 12-24 hours, to about 1-2 days, to about 1-2 wk or longer following the initiation of treatment. Generally, the dose of the therapeutic composition via continuous perfusion will be equivalent to that given by a single or multiple injections, adjusted over a period of time during which the perfusion occurs. For tumors of >4 cm, the volume to be administered will be about 4-10 ml (preferably 10 ml), while for tumors of <4 cm, a volume of about 1-3 ml will be used (preferably 3 ml). Multiple injections delivered as single dose comprise about 0.1 to about 0.5 ml volumes.

In certain embodiments, the tumor being treated may not, at least initially, be resectable. Treatments with therapeutic SENP1 inhibitor compositions may increase the resectability of the tumor due to shrinkage at the margins or by elimination of certain particularly invasive portions. Following treatments, resection may be possible. Additional treatments subsequent to resection will serve to eliminate microscopic residual disease at the tumor site.

VI. Combined Cancer Therapy with SENP1 Inhibitors and/or Other Anticancer Agents In the context of the present invention, it is contemplated that the SENP1 inhibitor or related-compounds thereof may be used in combination with an additional therapeutic agent to more effectively treat cancer. Anticancer agents may include but are not limited to, radiotherapy, chemotherapy, gene therapy, hormonal therapy or immunotherapy that targets cancer/tumor cells.

When an additional therapeutic agent is administered, as long as the dose of the additional therapeutic agent does not exceed previously quoted toxicity levels, the effective amounts of the additional therapeutic agent may simply be defined as that amount effective to inhibit and/or reduce the cancer growth when administered to an animal in combination with the SENP1 inhibitor or related-compounds thereof. This may be easily determined by monitoring the animal or patient and measuring those physical and biochemical parameters of health and disease that are indicative of the success of a given treatment. Such methods are routine in animal testing and clinical practice.

To kill cells, induce cell-cycle arrest, inhibit cell growth, inhibit metastasis, inhibit angiogenesis or otherwise reverse or reduce the malignant phenotype of cancer cells, using the methods and compositions of the present invention, one would generally contact a cell with SENP1 inhibitor or related-compounds thereof in combination with an additional therapeutic agent. These compositions would be provided in a combined amount effective to inhibit cell growth and/or induce apoptosis in the cell. This process may involve contacting the cells with SENP1 inhibitor or related-compounds thereof in combination with an additional therapeutic agent or factor(s) at the same time. This may be achieved by contacting the cell with a single composition or pharmacological formulation that includes both agents, or by contacting the cell with two distinct compositions or formulations, at the same time, wherein one composition includes the SENP1 inhibitor or derivatives thereof and the other includes the additional agent.

Alternatively, treatment with SENP1 inhibitor or related-compounds thereof may precede or follow the additional agent treatment by intervals ranging from minutes to weeks. In embodiments where the additional agent is applied separately to the cell, one would generally ensure that a significant period of time did not expire between the time of each delivery, such that the agent would still be able to exert an advantageously combined effect on the cell. In such instances, it is contemplated that one would contact the cell with both modalities within about 12-24 hr of each other and, more preferably, within about 6-12 hr of each other, with a delay time of only about 12 hr being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either SENP1 inhibitor or related-compounds thereof in combination with an additional therapeutic agent such as an anti-cancer agent will be desired. Various combinations may be employed, where SENP1 inhibitor or related-compounds thereof is "A" and the additional therapeutic agent is "B", as exemplified below:

A/B/A B/A/B B/B/A A/A/B B/A/A A/B/B B/B/B/A B/B/A/B
A/A/B/B A/B/A/B A/B/B/A B/B/A/A B/A/B/A B/A/A/B B/B/B/A
A/A/A/B B/A/A/A A/B/A/A A/A/B/A A/B/B/B B/A/B/B B/B/A/B

A. Chemotherapeutic Agents

In some embodiments of the present invention chemotherapy may be administered, as is typical, in regular cycles. A cycle may involve one dose, after which several days or the weeks without treatment ensues for normal tissues to recover from the drug's side effects. Doses may be given several days in a row, or every other day for several days, followed by a period of rest. If more than one drug is used, the treatment plan will specify how often and exactly when each drug should be given. The number of cycles a person receives may be determined before treatment starts (based on the type and stage of cancer) or may be flexible, in order to take into account how quickly the tumor is shrinking. Certain serious side effects may also require doctors to adjust chemotherapy plans to allow the patient time to recover.

Chemotherapeutic agents that may be used in combination with SENP1 inhibitor or an related-compound thereof in the treatment of cancer, include, but are not limited to cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, gemcitabien, navelbine, farnesyl-protein tansferase inhibitors, transplatinum, 5-fluorouracil and methotrexate, or any related-compound or derivative variant of the foregoing.

B. Radiotherapeutic Agents

Radiotherapeutic agents may also be use in combination with the compounds of the present invention in treating a cancer. Such factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

C. Immunotherapeutic Agents

Immunotherapeutics may also be employed in the present invention in combination with SENP1 inhibitor or related-compounds thereof in treating cancer. Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

D. Inhibitors of Cellular Proliferation

The tumor suppressor oncogenes function to inhibit excessive cellular proliferation. The inactivation of these genes destroys their inhibitory activity, resulting in unregulated proliferation. The tumor suppressors p53, p16 and C-CAM are described below.

High levels of mutant p53 have been found in many cells transformed by chemical carcinogenesis, ultraviolet radiation, and several viruses. The p53 gene is a frequent target of mutational inactivation in a wide variety of human tumors and is already documented to be the most frequently mutated gene in common human cancers. It is mutated in over 50% of human NSCLC (Hollstein et al., 1991) and in a wide spectrum of other tumors.

The p53 gene encodes a 393-amino acid phosphoprotein that can form complexes with host proteins such as large-T antigen and E1B. The protein is found in normal tissues and cells, but at concentrations which are minute by comparison with transformed cells or tumor tissue Wild-type p53 is recognized as an important growth regulator in many cell types. Missense mutations are common for the p53 gene and are essential for the transforming ability of the oncogene. A single genetic change prompted by point mutations can create carcinogenic p53. Unlike other oncogenes, however, p53 point mutations are known to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles (Winberg, 1991).

Another inhibitor of cellular proliferation is p16. The major transitions of the eukaryotic cell cycle are triggered by cyclin-dependent kinases, or CDK's. One CDK, cyclin-dependent kinase 4 (CDK4), regulates progression through the G1. The activity of this enzyme may be to phosphorylate Rb at late G1. The activity of CDK4 is controlled by an activating subunit, D-type cyclin, and by an inhibitory subunit, the p16INK4 has been biochemically characterized as a protein that specifically binds to and inhibits CDK4, and thus may regulate Rb phosphorylation (Serrano et al., 1993; Serrano et al., 1995). Since the p16INK4 protein is a CDK4 inhibitor (Serrano, 1993), deletion of this gene may increase the activity of CDK4, resulting in hyperphosphorylation of the Rb protein. p16 also is known to regulate the function of CDK6.

p16INK4 belongs to a newly described class of CDK-inhibitory proteins that also includes p16B, p19, p21WAF1, and p27KIP1. The p16INK4 gene maps to 9p21, a chromosome region frequently deleted in many tumor types. Homozygous deletions and mutations of the p16INK4 gene are frequent in human tumor cell lines. This evidence suggests that the p16INK4 gene is a tumor suppressor gene. This interpretation has been challenged, however, by the observation that the frequency of the p16INK4 gene alterations is much lower in primary uncultured tumors than in cultured cell lines (Caldas et al., 1994; Cheng et al., 1994; Hussussian et al., 1994; Kamb et al., 1994; Okamoto et al., 1994; Arap et al., 1995). Restoration of wild-type p16INK4 function by transfection with a plasmid expression vector reduced colony formation by some human cancer cell lines (Okamoto et al., 1994; Arap et al., 1995).

Other genes that may be employed according to the present invention include Rb, mda-7, APC, DCC, NF-1, NF-2, WT-1, MEN-I, MEN-II, zac1, p73, VHL, MMAC1/PTEN, DBCCR-1, FCC, rsk-3, p27, p27/p16 fusions, p21/p27 fusions, anti-thrombotic genes (e.g., COX-1, TFPI), PGS, Dp, E2F, ras, myc, neu, raf, erb, fms, trk, ret, gsp, hst, abl, E1A, p300, genes involved in angiogenesis (e.g., VEGF, FGF, thrombospondin, BAI-1, GDAIF, or their receptors) and MCC.

E. Regulators of Programmed Cell Death

Apoptosis, or programmed cell death, is an essential process in cancer therapy (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists.

Members of the Bcl-2 that function to promote cell death such as, Bax, Bak, Bik, Bim, Bid, Bad and Harakiri, are contemplated for use in combination with an SENP1 inhibitor or an related-compound thereof in treating cancer.

F. Surgery

It is further contemplated that a surgical procedure may be employed in the present invention. Approximately 60% of persons with cancer will undergo surgery of some type, which includes preventative, diagnostic or staging, curative and palliative surgery. Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

G. Hormonal Therapy

Hormonal therapy may also be used in conjunction with the SENP1 inhibitor or related-compound thereof as in the present invention, or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

H. Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine related-compounds; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increased intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

VII. Methods of Diagnosing a Hyperproliferative Disease

In a particular aspect, the present invention provides methods for diagnosing a hyperproliferative disease and/or a neoplasm by utilizing SENP1 as a marker for the hyperproliferative disease and/or neoplasm. The levels of SENP1 can also be used to determine or predict the susceptibility of a subject for developing a hyperproliferative disease. For example, the levels of SENP1 are measured in a biological sample and an increase in the levels of SENP1 compared to a normal or control subject indicates the presence of a neoplasm or hyperproliferative disease. An increase in the levels of SENP1 can refer to an increase in the expression of SENP1 or an increase in the activity of SENP1 or an increase in the protein levels of SENP1. Thus, an increase in the levels of SENP1 as indicated by the present invention can further defined, for example, by at least a 1 fold-difference, 2 fold-difference, 3 fold-difference, 4 fold-difference, 5 fold-difference, 6 fold-difference, 7 fold-difference, 8 fold-difference, 9 fold-difference 10 fold-difference, 15 fold-difference, 30 fold-difference, 50 fold-difference, 100 fold-difference in the expression of SENP1, activity of SENP1 and/or protein levels of SENP1 in the test biological sample compared to the normal or control or healthy sample. Of course, all of these fold-differences are exemplary, and any fold-difference in-between these points is also expected to be of use in the invention.

SENP1 gene products are usually found in most normal cells at extremely low levels. SENP1 gene products are overexpressed or the expression is enhanced in hyperproliferating cells or cancerous cells or tissues. It will thus be apparent that, when highly sensitive assays for SENP1 gene products are desired, it will sometimes be advantageous to incorporate signal or target amplification technologies into the assay format. See, for example, Plenat et al., 1997, Ann. Pathol. 17:17 (fluoresceinyl-tyramide signal amplification); Zehbe et al., 1997, J. Pathol. 150:1553 (catalyzed reporter deposition): other references listed herein (e.g., for bDNA signal amplification, for PCR and other target amplification formats); and other techniques known in the art.

As noted above, it is often unnecessary to quantitate the SENP1 mRNA or protein in the assays disclosed herein, because the detection of an SENP1 gene product (under assay conditions in which the product is not detectable in control or the product is low or background levels) is in itself sufficient for a diagnosis. As another example, when the levels of product found in a test (e.g., tumor) and control (e.g., healthy cell) samples are directly compared, quantitation may be superfluous.

When desired, however, quantities of SENP1 gene product measured in the assays described herein may be described in a variety of ways, depending on the method of measurement and convenience. Thus, normal, diagnostic, prognostic, high or low quantities of SENP1 protein/mRNA may be expressed as standard units of weight per quantity of biological sample (e.g., picograms per gram tissue), as a number of molecules per quantity of biological sample (e.g., transcripts/cell, moles/cell), as units of activity per cell or per other unit quantity, or by similar methods. The quantity of SENP1 gene product can also be expressed in relation to the quantity of another molecule; examples include: number of SENP1 transcripts in sample/number of GAPDH or 28S rRNA transcripts in sample: nanograms of SENP1/nanograms of total protein; and the like.

When measuring SENP1 gene products in two (or more) different samples, it will sometimes be useful to have a common basis of comparison for the two samples. For example, when comparing a sample of normal tissue and a sample of cancerous tissue, equal amounts of tissue (by weight, volume, number of cells, etc.) can be compared. Alternatively, equivalents of a marker molecule (e.g., GAPDH, 28S rRNA) may be used. For example, the amount of SENP1 protein in a healthy tissue sample containing 10 picograms of GAPDH or 28S rRNA can be compared to a sample of diseased tissue containing the same amount of GAPDH or 28S rRNA. If the level of SENP1 gene product is greater than at least 1 fold-difference, 2 fold-difference, 3, fold-difference, 4 fold-difference, 5 fold-difference, 6 fold-difference, 7 fold-difference, 8 fold-difference, 9 fold-difference 10 fold-difference, 15 fold-difference, 30 fold-difference, 50 fold-difference, 100 fold-difference than level of SENP1 gene product in the normal or control or healthy sample, then the sample is considered to be diseased, such is a cancerous sample.

It will also be recognized by those of skill that virtually any of the assays described herein can be designed to be quantitative. Typically, a known quantity or source of an SENP1 gene product (e.g., produced using the methods and compositions of the invention) is used to calibrate the assay.

In certain embodiments, assay formats are chosen that detect the presence, absence, or abundance of an SENP1 gene product in each cell in a sample (or in a representative sampling). Examples of such formats include those that detect a signal by histology (e.g., immunohistochemistry with signal-enhancing or target-enhancing amplification steps) or fluorescence-activated cell analysis or cell sorting (FACS). These formats are particularly advantageous when dealing with a highly heterogeneous cell population (e.g., containing multiple cells types in which only one or a few types have elevated SENP1 levels, or a population of similar cells expressing SENP1 at different levels).

In the present invention, a hyperproliferative disease is further defined as cancer. In still further embodiments, the cancer is melanoma, non-small cell lung, small-cell lung, lung, leukemia, hepatocarcinoma, retinoblastoma, astrocytoma, glioblastoma, gum, tongue, neuroblastoma, head, neck, breast, pancreatic, prostate, renal, bone, testicular, ovarian, mesothelioma, cervical, gastrointestinal, lymphoma, brain, colon, sarcoma or bladder. More particularly, the cancer is prostate cancer.

In other embodiments, the hyperproliferative disease is rheumatoid arthritis, inflammatory bowel disease, osteoarthritis, leiomyomas, adenomas, lipomas, hemangiomas, fibromas, vascular occlusion, restenosis, atherosclerosis, preneoplastic lesions (such as adenomatous hyperplasia and prostatic intraepithelial neoplasia), carcinoma in situ, oral hairy leukoplakia, or psoriasis.

The biological sample can be obtained from a fluid sample (e.g., blood, serum or other bodily fluids, e.g., urine, etc.) a tissue biopsy and/or aspiration of tissue or cells during a surgical procedure. In certain embodiments, a tissue may comprise, but is not limited to, adipocytes, alveolar, ameloblasts, axon, basal cells, blood (e.g., lymphocytes), blood vessel, bone, bone marrow, brain, breast, cartilage, cervix, colon, cornea, embryonic, endometrium, endothelial, epithelial, esophagus, facia, fibroblast, follicular, ganglion cells, glial cells, goblet cells, kidney, liver, lung, lymph node, muscle, neuron, ovaries, pancreas, peripheral blood, prostate, skin, skin, small intestine, spleen, stem cells, stomach, testes, anthers, and ascite tissue.

A. Nucleic Acid Assays

One embodiment of the instant invention comprises a method for detecting variation in the expression of SENP1. This may comprise determining the level of SENP1 expressed, or determining specific alterations in the expressed product. It is understood by the present invention that SENP1 levels are increased which in turn increase androgen receptor or AR transcription.

In one embodiment, this invention provides for methods of detecting and or quantifying expression of SENP1 mRNAs (including splicing or sequence variants and alternative alleles). In an alternative embodiment, the invention provides methods for detecting and analyzing normal or abnormal SENP1 genes (or fragments thereof). The form of such qualitative or quantitative assays may include, but is not limited to, amplification-based assays with or without signal amplification, hybridization based assays, and combination amplification-hybridization assays. It will be appreciated by those of skill that the distinction between hybridization and amplification is for convenience only: as illustrated in the examples below, many assay formats involve elements of both hybridization and amplification, so that the categorization is somewhat arbitrary in some cases.

Depending on the format, the specific nucleic acid of interest is identified in the sample directly using amplification or with a second, known nucleic acid following amplification. Next, the identified product is detected. In certain applications, the detection may be performed by visual means (e.g., ethidium bromide staining of a gel). Alternatively, the detection may involve indirect identification of the product via chemiluminescence, radioactive scintigraphy of radiolabel or fluorescent label or even via a system using electrical or thermal impulse signals (Affymax Technology; Bellus, 1994).

Following detection, one may compare the results seen in a given patient with a statistically significant reference group of normal patients and patients that have been diagnosed with a hyperproliferative disease, such as prostate cancer.

It is contemplated that other mutations in the SENP1 gene may be identified in accordance with the present invention by detecting a nucleotide change in particular nucleic acids (U.S. Pat. No. 4,988,617, incorporated herein by reference). A variety of different assays are contemplated in this regard, including but not limited to, fluorescent in situ hybridization (FISH; U.S. Pat. No. 5,633,365 and U.S. Pat. No. 5,665,549, each incorporated herein by reference), direct DNA sequencing, PFGE analysis, Southern or Northern blotting, single-stranded conformation analysis (SSCA), RNAse protection assay, RT-PCR, allele-specific oligonucleotide (ASO, e.g., U.S. Pat. No. 5,639,611), dot blot analysis, denaturing gradient gel electrophoresis (e.g., U.S. Pat. No. 5,190,856 incorporated herein by reference), RFLP (e.g., U.S. Pat. No. 5,324,631 incorporated herein by reference) and PCR™-SSCP.

1. Preparation of Nucleic Acids

Firstly, a biological sample is obtained from a subject. The biological sample may be tissue or fluid. In certain embodiments, the biological sample includes cells from the prostate and/or any other tissue known to express androgen receptors. In some embodiments, nucleic acid assays are performed with a sample of nucleic acid isolated from the cell, tissue, organism, or cell line to be tested.

Nucleic acids used are isolated from cells contained in the biological sample, according to standard methodologies (Sambrook et al., 1989). The nucleic acid may be genomic DNA or fractionated or whole cell RNA. In this context, "isolated" refers to any separation of the species or target to be detected from any other substance in the mixture, but does not necessarily indicate a significant degree of purification of the target. One of skill will appreciate that, where alterations in the copy number of the SENP1 gene are to be detected, genomic DNA is the target to be detected. Where RNA is used, it may be desired to convert the RNA to a complementary DNA (cDNA). In one embodiment, the RNA is whole cell RNA; in another, it is poly-A RNA. Normally, the nucleic acid is amplified. Methods for isolating nucleic acids are well known to those of skill in the art and are described, for example, Tijssen, P. ed. of LABORATORY TECHNIQUES IN BIOCHEMISTRY AND MOLECULAR BIOLOGY: HYBRIDIZATION WITH NUCLEIC ACID PROBES, PART I. THEORY AND NUCLEIC ACID PREPARATION, Elsevier, N.Y. (1993) Chapt 3, which is incorporated herein by reference. In one embodiment, the total nucleic acid is isolated from a given sample using an acid guanidinium-phenol-chloroform extraction method and poly(A) (-) mRNA is isolated by oligo-dT column chromatography or by using $(dT)_n$ magnetic beads (see. e.g., Sambrook et al., and Ausubel et al., supra.

2. Amplification Based Assays

In one embodiment, the assays of the present invention are amplification-based assays for detection of an SENP1 gene or gene product. In an amplification based assay, all or part of an SENP1 gene or transcript (e.g., mRNA or cDNA; hereinafter also referred to as "target") is amplified, and the amplification product is then detected directly or indirectly. When there is no underlying gene or gene product to act as a template, no amplification product is produced (e.g., of the expected size), or amplification is non-specific and typically there is no single amplification product. In contrast, when the underlying gene or gene product is present, the target sequence is amplified, providing an indication of the presence and/or quantity of the underlying gene or mRNA. Target amplification-based assays are well known to those of skill in the art.

The present invention involves the use of a wide variety of primers and probes for detecting SENP1 genes and gene products. Such primers and probes are sufficiently complementary to the SENP1 gene or gene product to hybridize to the target nucleic acid. Primers are typically at least 6 bases in length, usually between about 10 and about 100 bases, typically between about 12 and about 50 bases, and often between about 14 and about 25 bases in length. One of skill, having reviewed the present disclosure, will be able, using routine methods, to select primers to amplify all, or any portion, of the SENP1 gene or gene product, or to distinguish between variant gene products, SENP1 alleles, and the like. The Example Section lists illustrative primers useful for PCR amplification of the SENP1, or specific SENP1 gene products or regions. As is known in the art, single oligomers (e.g., U.S. Pat. No. 5,545,522), nested sets of oligomers, or even a degenerate pool of oligomers may be employed for amplification.

The invention provides a variety of methods for amplifying and detecting an SENP1 gene or gene product, including the polymerase chain reaction (including all variants, e.g., reverse-transcriptase-PCR; the Sunrise Amplification System (Oncor, Inc, Gaithersburg Md.); and numerous others known in the art). In one illustrative embodiment, PCR amplification is carried out in a 50 μl solution containing the nucleic acid sample (e.g., cDNA obtained through reverse transcription of SENP1 RNA), 100 μM in each dNTP (dATP, dCTP, dGTP and dTTP; Pharmacia LKB Biotechnology, NJ), the SENP1-specific PCR primer(s), 1 unit/Taq polymerase (Perkin Elmer. Norwalk Conn.). 1×PCR buffer (50 mM KCl, 10 mM Tris, pH 8.3 at room temperature, 1.5 mM $MgCl_2$, 0.01% gelatin) with the amplification run for about 30 cycles at 94° for 45 sec, 550 for 45 sec and 72° for 90 sec. However, as will be appreciated, numerous variations may be made to optimize the PCR amplification for any particular reaction.

Other suitable target amplification methods include the ligase chain reaction (LCR: e.g., Wu and Wallace 1989; Landegren et al., 1988; Barany, 1991 and Barringer et al., 1990); strand displacement amplification (SDA; e.g., Walker et al., 1992); transcription amplification (e.g., Kwoh et al., 1989); self-sustained sequence replication (3SR; e.g., Fahy et al., 1992; Guatelli et al., 1990); the nucleic acid sequence based amplification (NASBA, Cangene, Mississauga, Ontario; e.g., Compton, 1991); the transcription-based amplification system (TAS); and the self-sustained sequence replication system (SSR). Each of the aforementioned publications is incorporated herein by reference. One useful variant of PCR is PCR ELISA (e.g., Boehringer Mannheim Cat. No. 1 636 111) in which digoxigenin-dUTP is incorporated into the PCR product. The PCR reaction mixture is denatured and hybridized with a biotin-labeled oligonucleotide designed to anneal to an internal sequence of the PCR product. The hybridization products are immobilized on streptavidin coated plates and detected using anti-digoxigenin antibodies. Examples of techniques sufficient to direct persons of skill through in vitro amplification methods are found in PCR TECHNOLOGY: PRINCIPLES AND APPLICATIONS FOR DNA AMPLIFICATION, H. Erlich, Ed. Freeman Press, New York, N.Y. (1992); PCR PROTOCOLS: A GUIDE TO METHODS AND APPLICATIONS, eds. Innis, Gelfland, Snisky, and White, Academic Press, San Diego, Calif. (1990); Manila et al., 1991; Eckert and Kunkel, 1991; U.S. Pat. Nos. 4,683,195, 4,683,202, and 4,965,188; Barringer et al, 1990; Lomell et al., 1989, each of which is incorporated herein for all purposes.

Amplified products may be directly analyzed, e.g., by size as determined by gel electrophoresis; by hybridization to a target nucleic acid immobilized on a solid support such as a bead, membrane, slide, or chip, by sequencing, immunologically, e.g., by PCR-ELISA, by detection of a fluorescent, phosphorescent, or radioactive signal; or by any of a variety of other well-known means. For example, an illustrative example of a detection method uses PCR primers augmented with hairpin loops linked to fluorescein and a benzoic acid derivative that serves as a quencher, such that fluorescence is emitted only when the primers unfold to bind their targets and replication occurs.

Because SENP1 mRNA is typically expressed as an extremely rare transcript, present at very low levels even in SENP1 positive cells, it is often desirable to optimize or increase the signal resulting from the amplification step. One way to do this is to increase the number of cycles of amplification. For example, although 20-25 cycles are adequate for amplification of most mRNAs using the polymerase chain reaction under standard reaction conditions, detection of SENP1 mRNA in many samples can require as many as 30 to 35 cycles of amplification, depending on detection format and efficiency of amplification. It will be recognized that judicious choice of the amplification conditions including the number of amplification cycles can be used to design an assay that results in an amplification product only when there is a threshold amount of target in the test sample (i.e., so that only samples with a high level of SENP1 mRNA give a "positive" result). In addition, methods are known to increase signal produced by amplification of the target sequence. Methods for augmenting the ability to detect the amplified target include signal amplification system such as: branched DNA signal amplification (e.g., U.S. Pat. No. 5,124,246; Urdea, 1994); tyramide signal amplification (TSA) system (Du Pont); catalytic signal amplification (CSA; Dako): Q Beta Replicase systems (Tyagi et al., 1996); or the like.

One of skill in the art will appreciate that whatever amplification method is used, a variety of quantitative methods known in the art can be used if quantitation is desired. For example, when desired, two or more polynucleotides can be co-amplified in a single sample. This method can be used as a convenient method of quantitating the amount of SENP1 mRNA in a sample, because the reverse transcription and amplification reactions are carried out in the same reaction for a target and control polynucleotide. The co-amplification of the control polynucleotide (usually present at a known concentration or copy number) can be used for normalization to the cell number in the sample as compared to the amount of SENP1 in the sample. Suitable control polynucleotides for co-amplification reactions include DNA, RNA expressed from housekeeping genes, constitutively expressed genes, and in vitro synthesized RNAs or DNAs added to the reaction mixture. Endogenous control polynucleotides are those that are already present in the sample, while exogenous control polynucleotides are added to a sample, creating a "spiked" reaction. Illustrative control RNAs include beta-actin RNA, GAPDH RNA, snRNAs, SENP1, and endogenously expressed 28S rRNA (see Khan et al., 1992). Exogenous control polynucleotides include a synthetic AW106 cRNA, which may be synthesized as a sense strand from pAW106 by T7 polymerase. It will be appreciated that for the co-amplification method to be useful for quantitation, the control and target polynucleotides must typically both be amplified in a linear range. Detailed protocols for quantitative PCR may be found in PCR PROTOCOLS, A GUIDE TO METHODS AND APPLICATIONS. Innis et al., Academic Press, Inc. N.Y., (1990) and Ausubel et al., supra (Unit 15) and Diaco, R. (1995) Practical Considerations for the Design of Quantitative PCR Assays, in PCR STRATEGIES, pg. 84-108, Innis et al. eds, Academic Press, New York.

Depending on the sequence of the endogenous or exogenous standard, different primer sets may be used for the co-amplification reaction. In one method, called competitive amplification, quantitative PCR involves simultaneously co-amplifying a known quantity of a control sequence using the same primers used for amplification of the target nucleic acid (one pair of 2 primers). In an alternative embodiment, known as non-competitive competition, the control sequence and the target sequence (e.g., SENP1 cDNA) are amplified using different primers (i.e., 2 pairs of 2 primers). In another alternative embodiment, called semi-competitive amplification, three primers are used, one of which is SENP1-specific, one of which is control specific, and one of which is capable of annealing to both the target and control sequences. Semi-competitive amplification is described in U.S. Pat. No. 5,629,154, which is incorporated herein by reference.

In another embodiment, a reverse transcriptase PCR™ amplification procedure may be performed to quantify the amount of mRNA amplified. Methods of reverse transcribing RNA into cDNA are well known (see Sambrook et al., 1989). Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882,864.

3. Hybridization-Based Assays

A variety of methods for specific DNA and RNA measurement using nucleic acid hybridization techniques are known to those of skill in the art (see Sambrook et al., supra). Hybridization based assays refer to assays in which a probe nucleic acid is hybridized to a target nucleic acid. Usually the nucleic acid hybridization probes used in the invention are entirely or substantially identical to a contiguous sequence of the SENP1 gene or RNA sequence. Preferably, nucleic acid probes are at least about 10 bases, often at least about 20 bases, and sometimes at least about 200 bases or more in length. Methods of selecting nucleic acid probe sequences for use in nucleic acid hybridization are discussed in Sambrook et al., supra. In some formats, at least one of the target and probe is immobilized. The immobilized nucleic acid may be DNA, RNA, or another oligo- or poly-nucleotide, and may comprise natural or non-naturally occurring nucleotides, nucleotide analogs, or backbones. Such assays may be in any of several formats including: Southern, Northern, dot and slot blots, high-density polynucleotide or oligonucleotide arrays (e.g., GeneChips® Affymetrix), dip sticks, pins, chips, or beads. All of these techniques are well known in the art and are the basis of many commercially available diagnostic kits. Hybridization techniques are generally described in Hames et al., ed., NUCLEIC ACID HYBRIDIZATION, A PRACTICAL APPROACH IRL Press, (1985); Gall and Pardue 1969; and John et al., 1969.

A variety of nucleic acid hybridization formats are known to those skilled in the art. For example, one common format is direct hybridization, in which a target nucleic acid is hybridized to a labeled, complementary probe. Typically, labeled nucleic acids are used for hybridization, with the label providing the detectable signal. One method for evaluating the presence, absence, or quantity of SENP1 mRNA is carrying out a Northern transfer of RNA from a sample and hybridization of a labeled SENP1 specific nucleic acid probe. As was noted supra, SENP1 mRNA, when present at all, is present in very low quantities in most cells. Therefore, when Northern hybridization is used, it will often be desirable to use an amplltication step (or, alternatively, large amounts of starting RNA). A useful method for evaluating the presence, absence, or quantity of DNA encoding SENP1 proteins in a sample involves a Southern transfer of DNA from a sample and hybridization of a labeled SENP1 specific nucleic acid probe.

Other common hybridization formats include sandwich assays and competition or displacement assays. Sandwich assays are commercially useful hybridization assays for detecting or isolating nucleic acid sequences. Such assays utilize a "capture" nucleic acid covalently immobilized to a solid support and a labeled "signal" nucleic acid in solution. The biological or clinical sample will provide the target nucleic acid. The "capture" nucleic acid and "signal" nucleic acid probe hybridize with the target nucleic acid to form a "sandwich" hybridization complex. To be effective, the signal nucleic acid cannot hybridize with the capture nucleic acid.

4. Chip-Based and Slide-Based Assays

Yet further, it is contemplated that chip-based DNA technologies such as those described by Hacia et al. (1996) and Shoemaker et al. (1996) can be used for diagnosis. Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization. See also Pease et al., (1994); Fodor et al., (1991).

The present invention, thus provides probe-based hybridization assays for SENP1 gene products employing arrays of immobilized oligonucleotide or polynucleotides to which an SENP1 nucleic acid can hybridize (i.e., to some, but usually not all or even most, of the immobilized oligo- or polynucleotides). High density oligonucleotide arrays or polynucleotide arrays provide a means for efficiently detecting the presence and characteristics (e.g., sequence) of a target nucleic acid (e.g., SENP1 gene, mRNA, or cDNA). Techniques are known for producing arrays containing thousands of oligonucleotides complementary to defined sequences, at defined locations on a surface using photolithographic techniques for synthesis in situ (see, e.g., U.S. Pat. Nos. 5,578, 832; 5,556,752; and 5,510,270; Fodor et al., 1991; Pease et al., 1994; and Lockhart et al., 1996) or other methods for rapid synthesis and deposition of defined oligonucleotides (Blanchard et al., 1996). When these methods are used, oligonucleotides (e.g., 20-mers) of known sequence are synthesized directly on a surface such as a derivatized glass slide. Usually, the array produced is redundant, having several oligonucleotide probes on the chip specific for the SENP1 polynucleotide to be detected.

Combinations of oligonucleotide probes can be designed to detect alternatively spliced mRNAs, or to identify which of various SENP1 alleles is expressed in a particular sample.

In one illustrative embodiment, cDNA prepared by reverse transcription of total RNA from a test cell is amplified (e.g., using PCR). Typically the amplification product is labeled, e.g., by incorporation of a fluorescently labeled dNTP. The labeled cDNAs are then hybridized to a chip comprising oligonucleotide probes complementary to various subsequences of the SENP1 gene. The positions of hybridization are determined (e.g., in accordance with the general methods of Shalon et al., 1996, or Schena et al., 1996), and sequence (or other information) deduced from the hybridization pattern, by means well known in the art.

In one embodiment, two cDNA samples. each labeled with a different fluorescent group, are hybridized to the same chip. The ratio of the hybridization of each labeled sample to sites complementary to the SENP1 gene are then assayed. If both samples contain the same amount of SENP1 mRNA, the ratio of the two fluors will be 1:1 (it will be appreciated that the signal from the fluors may need to be adjusted to account for any difference in the molar sensitivity of the fluors). In contrast, if one sample is from a healthy (or control) tissue and the second sample is from a cancerous tissue the fluor used in the second sample will predominate.

5. In Situ Hybridization

An alternative means for detecting expression of a gene encoding an SENP1 protein is in situ hybridization. In situ hybridization assays are well known and are generally described in Angerer et al., 1987 and Ausubel et al., supra. In an in situ hybridization assay, cells or tissue specimens are fixed to a solid support, typically in a permeablilized state, typically on a glass slide. The cells are then contacted with a hybridization solution at a moderate temperature to permit annealing of labeled nucleic acid probes (e.g., $^{35}$S-labeled riboprobes, fluorescently labeled probes) completely or substantially complementary to SENP1. Free probe is removed by washing and/or nuclease digestion, and bound probe is visualized directly on the slide by autoradiography or an appropriate imaging techniques, as is known in the art.

B. Immunodiagnosis

Antibodies can be used in characterizing the SENP1 content through techniques such as ELISAs and Western blot analysis.

The steps of various other useful immunodetection methods have been described in the scientific literature, such as, e.g., Nakamura et al., (1987). Immunoassays, in their most simple and direct sense, are binding assays. Certain preferred immunoassays are the various types of radioimmunoassays (RIA) and immunobead capture assay. Immunohistochemical detection using tissue sections also is particularly useful. However, it will be readily appreciated that detection is not limited to such techniques, and Western blotting, dot blotting, FACS analyses, and the like also may be used in connection with the present invention.

The antibody compositions of the present invention will find great use in immunoblot or Western blot analysis. The antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. Immunologically-based detection methods for use in conjunction with Western blotting include enzymatically-, radiolabel-, or fluorescently-tagged secondary antibodies against the toxin moiety are considered to be of particular use in this regard. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

1. Western Blot Analysis

Western blot analysis is an established technique that is commonly employed for analyzing and identifying proteins. The proteins are first separated by electrophoresis in polyacrylamide gel, then transferred ("blotted") onto a nitrocellulose membrane or treated paper, where they bind in the same pattern as they formed in the gel. The antigen is overlaid first with antibody, then with anti-immunoglobulin or protein A labeled with a radioisotope, fluorescent dye, or enzyme. One of ordinary skill in the art would be familiar with this commonly used technique for quantifying protein in a sample.

2. ELISAs

Immunoassays, in their most simple and/or direct sense, are binding assays. Certain preferred immunoassays are the various types of enzyme linked immunosorbent assays (ELISAs) and/or radioimmunoassays (RIA) known in the art. Immunohistochemical detection using tissue sections is also particularly useful. However, it will be readily appreciated that detection is not limited to such techniques, and/or western blotting, dot blotting, FACS analyses, and/or the like may also be used.

In one exemplary ELISA, the anti-SENP-1 antibodies of the invention are immobilized onto a selected surface exhibiting protein affinity, such as a well in a polystyrene microtiter plate. Then, a test composition suspected of containing the SENP1 protein antigen, such as a clinical sample, is added to the wells. After binding and/or washing to remove non-specifically bound immune complexes, the bound SENP1 protein antigen may be detected. Detection is generally achieved by the addition of another antibody that is linked to a detectable label. This type of ELISA is a simple "sandwich ELISA". Detection may also be achieved by the addition of a second antibody, followed by the addition of a third antibody that has binding affinity for the second antibody, with the third antibody being linked to a detectable label.

In another exemplary ELISA, the samples suspected of containing the SENP1 protein antigen are immobilized onto the well surface and/or then contacted with the anti-SENP1 antibodies of the invention. After binding and/or washing to remove non-specifically bound immune complexes, the bound antiSENP1 antibodies are detected. Where the initial anti-SENP1 antibodies are linked to a detectable label, the immune complexes may be detected directly. Again, the immune complexes may be detected using a second antibody that has binding affinity for the first anti SENP1 antibody, with the second antibody being linked to a detectable label.

Another ELISA in which the SENP1 proteins, polypeptides and/or peptides are immobilized, involves the use of antibody competition in the detection. In this ELISA, labeled antibodies against SENP1 protein are added to the wells, allowed to bind, and/or detected by means of their label. The amount of SENP1 protein antigen in an unknown sample is then determined by mixing the sample with the labeled antibodies against wild type and/or mutant SENP1 before and/or during incubation with coated wells. The presence of SENP1 protein in the sample acts to reduce the amount of antibody against SENP1 protein available for binding to the well and thus reduces the ultimate signal. This is also appropriate for detecting antibodies against SENP1 protein in an unknown sample, where the unlabeled antibodies bind to the antigen-coated wells and also reduces the amount of antigen available to bind the labeled antibodies.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H2O2$, in the case of peroxidase as the enzyme label. Quantification is then achieved by measuring the degree of color generated, e.g., using a visible spectra spectrophotometer.

3. Immunohistochemistry

The antibodies of the present invention may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and/or is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in 70° C. isopentane; cutting the plastic capsule and/or removing the frozen cylinder of tissue; securing the tissue cylinder on a cryostat microtome chuck; and/or cutting 25-50 serial sections.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections.

4. Immunoelectron Microscopy

The antibodies of the present invention may also be used in conjunction with electron microscopy to identify intracellular tissue components. Briefly, and electron-dense label is conjugated directly or indirectly to the anti-SENP1 antibody. Examples of electron-dense labels according to the invention are ferritin and gold. The electron-dense label absorbs electrons and can be visualized by the electron microscope.

5. Protein Array Technology

Protein array technology allows high-throughput screening for gene expression and molecular interactions. Protein arrays appear as new and versatile tools in functional genomics, enabling the translation of gene expression patterns of normal and diseased tissues into protein product catalog. Protein function, such as enzyme activity, antibody specificity, and other ligand-receptor interactions and binding of nucleic acids or small molecules can be analyzed on a whole-genome level.

(1) Protein Biochip Assays

These arrays, which contain thousands of different proteins or antibodies spotted onto glass slides or immobilized in tiny wells, allow one to examine the biochemical activities and binding profiles of a large number of proteins at once. To examine protein interactions with such an array, a labeled protein is incubated with each of the target proteins immobilized on the slide, and then one determines which of the many proteins the labeled molecule binds.

The basic construction of protein chips has some similarities to DNA chips, such as the use of a glass or plastic surface dotted with an array of molecules. These molecules can be DNA or antibodies that are designed to capture proteins. Defined quantities of proteins are immobilized on each spot, while retaining some activity of the protein. With fluorescent markers or other methods of detection revealing the spots that have captured these proteins, protein microarrays are being used as powerful tools in high-throughput proteomics and drug discovery.

Glass slides are still widely used, since they are inexpensive and compatible with standard microarrayer and detection equipment. However, their limitations include multiple-based reactions, high evaporation rates, and possible cross-contamination.

Matrix slides offer a number of advantages, such as reduced evaporation and no possibility of cross-contamination, but they are expensive. Nanochips for proteomics have the same advantages, in addition to reduced cost and the capability of multiple-component reactions.

The earliest and best-known protein chip is the ProteinChip by Ciphergen Biosystems Inc. (Fremont, Calif.). The Protein-Chip is based on the surface-enhanced laser desorption and ionization (SELDI) process. Known proteins are analyzed using functional assays that are on the chip. For example, chip surfaces can contain enzymes, receptor proteins, or antibodies that enable researchers to conduct protein-protein interaction studies, ligand binding studies, or immunoassays. With state-of-the-art ion optic and laser optic technologies, the ProteinChip system detects proteins ranging from small peptides of less than 1000 Da up to proteins of 300 kDa and calculates the mass based on time-of-flight (TOF).

The ProteinChip biomarker system is the first protein biochip-based system that enables biomarker pattern recognition analysis to be done. This system allows researchers to address important clinical questions by investigating the proteome from a range of crude clinical samples (i.e., laser capture microdissected cells, biopsies, tissue, urine, and serum). The system also utilizes biomarker pattern software that automates pattern recognition-based statistical analysis methods to correlate protein expression patterns from clinical samples with disease phenotypes.

Some systems can perform biomarker discovery in days and validation of large sample sets within weeks. Its robotics system accessory automates sample processing, allowing hundreds of samples to be run per week and enabling a sufficient number of samples to be run, which provides high statistical confidence in comprehensive studies for marker discovery and validation.

(2) Microfluidic Chip-Based Immunoassays

Microfluidics is one of the most important innovations in biochip technology. Since microfluidic chips can be combined with mass spectrometric analysis, a microfluidic device has been devised in which an electrospray interface to a mass spectrometer is integrated with a capillary electrophoresis channel, an injector, and a protein digestion bed on a monolithic substrate (Wang et al., 2000). This chip thus provides a convenient platform for automated sample processing in proteomics applications.

These chips can also analyze expression levels of serum proteins with detection limits comparable to commercial enzyme-linked immunosorbent assays, with the advantage that the required volume sample is markedly lower compared with conventional technologies.

Biosite (San Diego) manufactures the Triage protein chip that simultaneously measures 100 different proteins by immunoassays. The Triage protein chip immunoassays are performed in a microfluidic plastic chip, and the results are achieved in 15 minutes with picomolar sensitivities. Microfluidic fluid flow is controlled in the protein chip by the surface architecture and surface hydrophobicity in the microcapillaries. The immunoassays utilize high-affinity antibodies and a near-infrared fluorescent label, which is read by a fluorometer.

(3) Tissue Microarray Technology

Tissue microarray technology provides a high-throughput approach for linking genes and gene products with normal and disease tissues at the cellular level in a parallel fashion. Compared with classical in situ technologies in molecular pathology that are very time-consuming, tissue microarrays provide increased throughput in two ways: up to 1000 tissue specimens can be analyzed in a single experiment, either at the DNA, RNA, or protein level; and tens of thousands of replicate tissue microarrays can be generated from a set of tissues. This process provides a template for analyzing many more biomarkers than has ever been possible previously in a clinical setting, even using archival, formalin-fixed specimens.

(4) Nanoscale Protein Analysis

Most current protocols including protein purification and automated identification schemes yield low recoveries that limit the overall process in terms of sensitivity and speed. Such low protein yields and proteins that can only be isolated from limited source material (e.g., biopsies) can be subjected to nanoscale protein analysis: a nanocapture of specific proteins and complexes, and optimization of all subsequent sample-handling steps, leading to a mass analysis of peptide fragments. This focused approach, also termed targeted proteomics, involves examining subsets of the proteome (e.g., those proteins that are specifically modified, bind to a particular DNA sequence, or exist as members of higher-order complexes or any combination thereof). This approach is used to identify genetic determinants of cancer that alter cellular physiology and respond to agonists.

A new detection technique called multiphoton detection, by Biotrace Inc. (Cincinnati), can quantify subzeptomole amounts of proteins and will be used for diagnostic proteomics, particularly for cytokines and other low-abundance proteins. Biotrace is also developing supersensitive protein biochips to detect concentrations of proteins as low as 5 fg/ml (0.2 attomole/ml), thereby permitting sensitivity that is 1000 times greater than current protein biochips.

VIII. Formulations and Routes for Administration of SENP1 Inhibitors or Related-Compounds Thereof Where clinical applications are contemplated, it will be necessary to prepare pharmaceutical compositions of SENP1 inhibitors or related-compounds thereof, or any additional therapeutic agent disclosed herein in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention in an effective amount may be dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifingal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

The composition(s) of the present invention may be delivered orally, nasally, intramuscularly, intraperitoneally, or intratumorally. In some embodiments, local or regional delivery of SENP1 inhibitors or related-compounds thereof, alone or in combination with an additional therapeutic agent, to a patient with cancer or pre-cancer conditions will be a very efficient method of delivery to counteract the clinical disease. Similarly, chemo- or radiotherapy may be directed to a particular, affected region of the subject's body. Regional chemotherapy typically involves targeting anticancer agents to the region of the body where the cancer cells or tumor are located. Other examples of delivery of the compounds of the present invention that may be employed include intra-arterial, intracavity, intravesical, intrathecal, intrapleural, and intraperitoneal routes.

Intra-arterial administration is achieved using a catheter that is inserted into an artery to an organ or to an extremity. Typically, a pump is attached to the catheter. Intracavity administration describes when chemotherapeutic drugs are introduced directly into a body cavity such as intravesical (into the bladder), peritoneal (abdominal) cavity, or pleural (chest) cavity. Agents can be given directly via catheter. Intravesical chemotherapy involves a urinary catheter to provide drugs to the bladder, and is thus useful for the treatment of bladder cancer. Intrapleural administration is accomplished using large and small chest catheters, while a Tenkhoff catheter (a catheter specially designed for removing or adding large amounts of fluid from or into the peritoneum) or a catheter with an implanted port is used for intraperitoneal chemotherapy. Abdomen cancer may be treated this way. Because most drugs do not penetrate the blood/brain barrier, intrathecal chemotherapy is used to reach cancer cells in the central nervous system. To do this, drugs are administered directly into the cerebrospinal fluid. This method is useful to treat leukemia or cancers that have spread to the spinal cord or brain.

Alternatively, systemic delivery of the chemotherapeutic drugs may be appropriate in certain circumstances, for example, where extensive metastasis has occurred. Intravenous therapy can be implemented in a number of ways, such as by peripheral access or through a vascular access device (VAD). A VAD is a device that includes a catheter, which is placed into a large vein in the arm, chest, or neck. It can be used to administer several drugs simultaneously, for long-term treatment, for continuous infusion, and for drugs that are vesicants, which may produce serious injury to skin or muscle. Various types of vascular access devices are available.

The active compositions of the present invention may include classic pharmaceutical preparations. Administration of these compositions according to the present invention will be via any common route so long as the target tissue is available via that route. This includes but is not limited to, oral, nasal, or buccal routes. Alternatively, administration may be by orthotopic, intradermal, subcutaneous, intramuscular, intraperitoneal or intravenous injection. Such compositions would normally be administered as pharmaceutically acceptable compositions, described supra. The drugs and agents also may be administered parenterally or intraperitoneally. The term "parenteral" is generally used to refer to drugs given intravenously, intramuscularly, or subcutaneously.

Solutions of the active compounds as free base or pharmacologically acceptable salts can be prepared in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The therapeutic compositions of the present invention may be administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH, exact concentration of the various components, and the pharmaceutical composition are adjusted according to the well known parameters. Suitable excipients for formulation with SENP1 inhibitors or related-compounds thereof include croscarmellose sodium, hydroxypropyl methylcellulose, iron oxides synthetic), magnesium stearate, microcrystalline cellulose, polyethylene glycol 400, polysorbate 80, povidone, silicon dioxide, titanium dioxide, and water (purified).

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

IX. Diagnostic or Therapeutic Kits

Any of the compositions described herein may be comprised in a kit. In a non-limiting example, it is envisioned that a compound that selectively binds to or identifies SENP1 may be comprised in a kit. Such compounds can be referred to as an "SENP1 marker", which may include, but are not limited to antibodies (monoclonal or polyclonal), SENP1 oligonucleotides, SENP1 polypeptides, small molecule or combinations thereof. It is envisioned that any of these SENP1 markers may be linked to a radioactive substance and/or a fluorescent marker for quick determination. The kits may also comprise, in suitable container means a lipid, and/or an additional agent, for example a radioactive or florescent marker.

The kits may comprise a suitably aliquoted SENP1 marker, lipid and/or additional agent compositions of the present invention, whether labeled or unlabeled, as may be used to prepare a standard curve for a detection assay. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the SENP1 marker, lipid, additional agent, and any other reagent containers in close confinement for commercial sale. Such containers may include injection or blow molded plastic containers into which the desired vials are retained.

Therapeutic kits of the present invention are kits comprising an inhibitor of SENP1 or an related-compound thereof. Such kits will generally contain, in suitable container means, a pharmaceutically acceptable formulation of SENP1 inhibitor or related-compound thereof. The kit may have a single container means, and/or it may have distinct container means for each compound.

When the components of the kit are provided in one and/or more liquid solutions, the liquid solution is an aqueous solution, with a sterile aqueous solution being particularly preferred. The SENP1 inhibitor compositions may also be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means.

The container means will generally include at least one vial, test tube, flask, bottle, syringe and/or other container means, into which the SENP1 inhibitor is suitably allocated. The kits may also comprise a second container means for containing a sterile, pharmaceutically acceptable buffer and/or other diluent.

The kits of the present invention will also typically include a means for containing the vials in close confinement for commercial sale, such as, e.g., injection and/or blow-molded plastic containers into which the desired vials are retained.

Irrespective of the number and/or type of containers, the kits of the invention may also comprise, and/or be packaged with, an instrument for assisting with the injection/administration and/or placement of the SENP1 inhibitor composition within the body of an animal. Such an instrument may be a syringe, pipette, forceps, and/or any such medically approved delivery vehicle.

X. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Cell Culture Maintenance and Treatment

LNCaP, PC-3, and DU145 cells were maintained in RPMI 1640 media containing 10% fetal bovine serum and 1% penicillin/streptomycin. The RWPE2 were maintained in Keratinocyte-Serum Free medium supplemented with 5 ng/ml human recombinant EGF and 0.05 mg/ml bovine pituitary extract. For hormone/cytokine treatment, the maintenance media was replaced with phenol red-free RPMI 1640 media containing 10% charcoal-stripped bovine serum and 1% penicillin/streptomycin.

Example 2

Plasmids and Antibodies

Flag-AR, ARE-luciferase, Gal4-luciferase, Gal4 DBD, and hemagglutinin (HA)-SUMO-1 plasmids were described previously in David et al., 2002, Kamitani et al., 1997, and Yu et al., 2001. PB (−426/+28)-Luciferase, FLAG-SENP1 mutatant (R630L, K631M), Flag-SENP2, His-SENP3, Flag-HDAC1, Flag-HDAC1 DM (K444, 476R), Gal4-DBD-HDAC1, Gal4-DBD-HDAC1 DM (K444, 476R), and Flag-AR DM (K386R, J520E) were prepared by standard cloning and PCR-based mutagenesis.

EGFP-SENP1 and EGFP-SENP1mutant (C603A) were prepared by standard cloning and PCR based mutagenesis. CD1 (−1745/+134), CD1 (−963/+134), CD1 (−66/+134), and, CD1 (−66/+134) mutant-driven luciferase plasmids were prepared by PCR cloning strategy (Albanese et al., 1995; Tetsu et al., 1999). Primers used were: CD1 (−1745/+134) (SEQ.ID.NO. 8: sense 5'CAGCTGGGCCGCCCT-TGT3' and SEQ.ID.NO. 9 antisense 5'CAGCTGGG-GAGGGCTG TGG3'), CD1 (−963/+134) (SEQ.ID.NO. 10 sense 5'TTAAAAAAAATGAGTCAGA ATGGAGAT-CAC3' and SEQ.ID.NO. 11 antisense 5'CAGCTGGG-GAGGGCTGTG3'), CD1 (−66/+134) (SEQ.ID.NO. 12 sense 5'TAACAACAGTAACGTCACACGGACTACAGG3' and SEQ.ID.NO. 13 antisense 5'CAGCTGGGGAG GGCT-GTG3'), and CD1 (−66/+134) mutant (SEQ.ID.NO. 14 sense 5'TAACAACAGTggCGTCACACGG3' and SEQ.ID.NO. 15 antisense 5'CCGTGTGACGccACTGTTGTTA').

An anti-AR antibody was raised against AR from a rabbit immunized with a bacterial recombinant AR N-terminal (amino acids 1 to 322) peptide.

Example 3

Immunohistochemistry and In Situ Hybridization

Immunohistochemical stain of AR was performed as previously described (14). For in situ hybridization, high specificity digoxigenin-labeled SENP1 RNA sense and antisense probes the were synthesized by incubation of SENP1 fragment 1519-1932 (cloned in pBluescript II vector) with T7 or T3 RNA polymerase and GTP, ATP, CTP, and digoxigenin-labelled-UTP (Roche, Indianapolis, Ind.). After wax removal and rehydration, 4-μm sections of formalin-fixed prostatic tissue were prehybridized for two hours and then hybridized overnight to the sense and anti-sense probe as described (Li et al., 2002). The hybridization signals were detected with alkaline phosphatase-conjugated anti-digoxigenin antibody. The positive hybridization signals were developed by chromogenic reactions with nitroblue tetrazolium chloride (NTB) and 5-bromo-4-chloro-3-indolyl-phosphate (BCIP).

Example 4

RNA Isolation, QRT-PCR and Semi-quantatitive RT-PCR

Cells (LNCaP and/or PC-3) were prepared for RNA isolation using the RNA-Bee Reagent (Tel-Test Inc, Friendswood, Tex.) according to manufacture's instructions with stock samples diluted to the appropriate concentrations with the DEPC-treated water.

The TaqMan Master Mix Reagents (Applied Biosystems, Branchburg, N.J.) were utilized for the quantitative real-time PCR (QRT-PCR) reaction. Primers for either SENP1 (500 μM; forward: SEQ. ID. NO. 5: 5'-TTGGCCAGAGTG-CAAATGG-3' and reverse: SEQ. ID. NO. 6 5'-TCGGCT-GTTTCTTGATTTTTGTAA-3') or the housekeeping 18S rRNA were utilized. SENP1 RNA levels were calculated using the TaqMan ABI PRISM 7900 Sequence Detector System (PE Applied Biosystems).

Total cellular RNA was extracted according to a protocol supplied with Qiagen RNeasy Kit. RT-PCR was performed on 20 ng of total RNA with specific primers and Qiagen onestep RT-PCR kit (Qiagen) according to the manufacturer's protocol. Primers used are: SENP1 (SEQ.ID.NO. 16 sense 5' AGAGGACCAGCTTTCGCTTTCTGA3 and SEQ.ID.NO. 17 antisense 5' TTGAGGTCTTTCGGGTTTC-GAGGT 3'), GAPDH (SEQ.ID.NO. 18 sense 5 CGGAGT-CAACGGATTTGGTCGTAT 3' and SEQ.ID.NO. 19 antisense 5' AGCCTTCTC CATGGTGGTGAAGAC 3'), and cyclin D1 (SEQ.ID.NO. 20 sense 5' AGAAGCTGTG CATC-TACACCGACA 3' and SEQ.ID.NO. 21 antisense 5 TGGGT-CACACTTGATCACT CTGGA 3').

After PCR, samples were run on 1.5% agarose gel. PCR products were visualized by ethidium bromide staining and photographed. Experiments were performed in triplicate and the expression of each gene was standardized with housekeeping gene GADPH as a reference.

Example 5

Production of an siRNA Molecule

For SENP1 siRNA system, a 21-nucleotide SENP1 siRNA (SEQ. ID. NO. 7 GTGAACCACAACTCCGTATTC) was synthesized. The same sequence in the inverted orientation was used as non-specific siRNA controls. The SENP1 and non-specific siRNA oligos were inserted into pSuppressor Neo vector (IMGENEX Corporation) according to the manufacturer's instruction.

For HDAC1 siRNA, a kit containing four pooled SMART-selected HDAC1, and cyclin D1 siRNA duplexes and non-specific siRNA duplexes were used.

Example 6

RNA Interference

PC-3 and LNCaP cells were grown in 24-well plates. Cells were transfected with the oligos (40 pmol/well) or siRNA plasmid (200 ng) for one (for PC-3) or three times within 12 hour intervals (for LNcaP) using lipfectamine 2000 (Invitrogen). PSA ELISA or Luciferase assays were used for analysis.

Example 7

PSA ELISA Assay

For assessment of PSA, the PSA ELISA assay kit was purchased from MP Biomedicals (Orangeburg, N.Y.) and performed according to manufacturer's instruction. Using a microtiter plate reader, the ng/mL concentration of the cell samples was calculated from the standard curve.

Example 8

Elevated SENP1 Levels in PIN and Prostate Cancer Relative to Normal Prostate Epithelia The inventors sought to determine SENP1 expression in prostate cancer tissues. In situ hybridization studies were conducted in tissue specimens obtained following prostectomy of 25 prostate cancer patients. All 25 samples have cancerous foci and 24 exhibit high-grade PIN. Using SENP1 anti-sense and sense (as control) probes, the inventors observed an increase of SENP1 expression in PIN and cancer cell relative to adjacent normal prostatic epithelia (FIGS. 1A, 1B, and 1C). Increase in the expression of SENP1 was readily observed in the precursor state of prostate cancer, PIN; 16 of the 24 samples with PIN (66.6%; represented with black arrow, FIG. 1A) expressed greater levels of SENP1 as compared to staining of normal epithelia (white arrow head, FIG. 1A). Similarly, among the 25 cases, 14 (56.0%) showed increased SENP1 expression in cancer cells. Elevated SENP1 expression occurred consistently in both PIN and cancer (88% of the cases). The SENP1 sense probe (FIG. 1C, insert) did not produce the profound staining observed with the SENP1 anti-sense probe; validating the specificity of the later probe. Therefore, SENP1 expression was dramatically enhanced in prostate cancer cells and precursor PIN areas.

To determine the relationship between SENP1 and AR expression, the inventors also evaluated AR expression levels in the above tissue samples by immunohistochemistry. The AR levels were not dramatically increased in these prostate cancer cells (FIG. 1D, black arrow head) as compared to normal prostate cells (FIG. 1D, white arrow head). The increased AR transcription activity by SENP1 was not exclusively due to increased levels of AR expression.

The mRNA expression of SENP1 was also surveyed in prostate cancer cell lines, RPWE2, LNCaP, DU-145, and PC-3 by RT-PCR. SENP1 was found to be over-expressed in all four prostate cancer cell lines, but not in normal prostate epithelial cell RPWE-1 (FIG. 1E). Furthermore, SENP1 message was also lower in other cancer cells, such as U2OS, MCF7, MDA-21, and Hela cells. These results suggested that SENP1 plays an important role in the pathobiology of the prostate gland. These results also suggested that SENP1 can be used as a diagnostic marker to determine and/or predict cancer in patients.

Example 9

Figure 2:
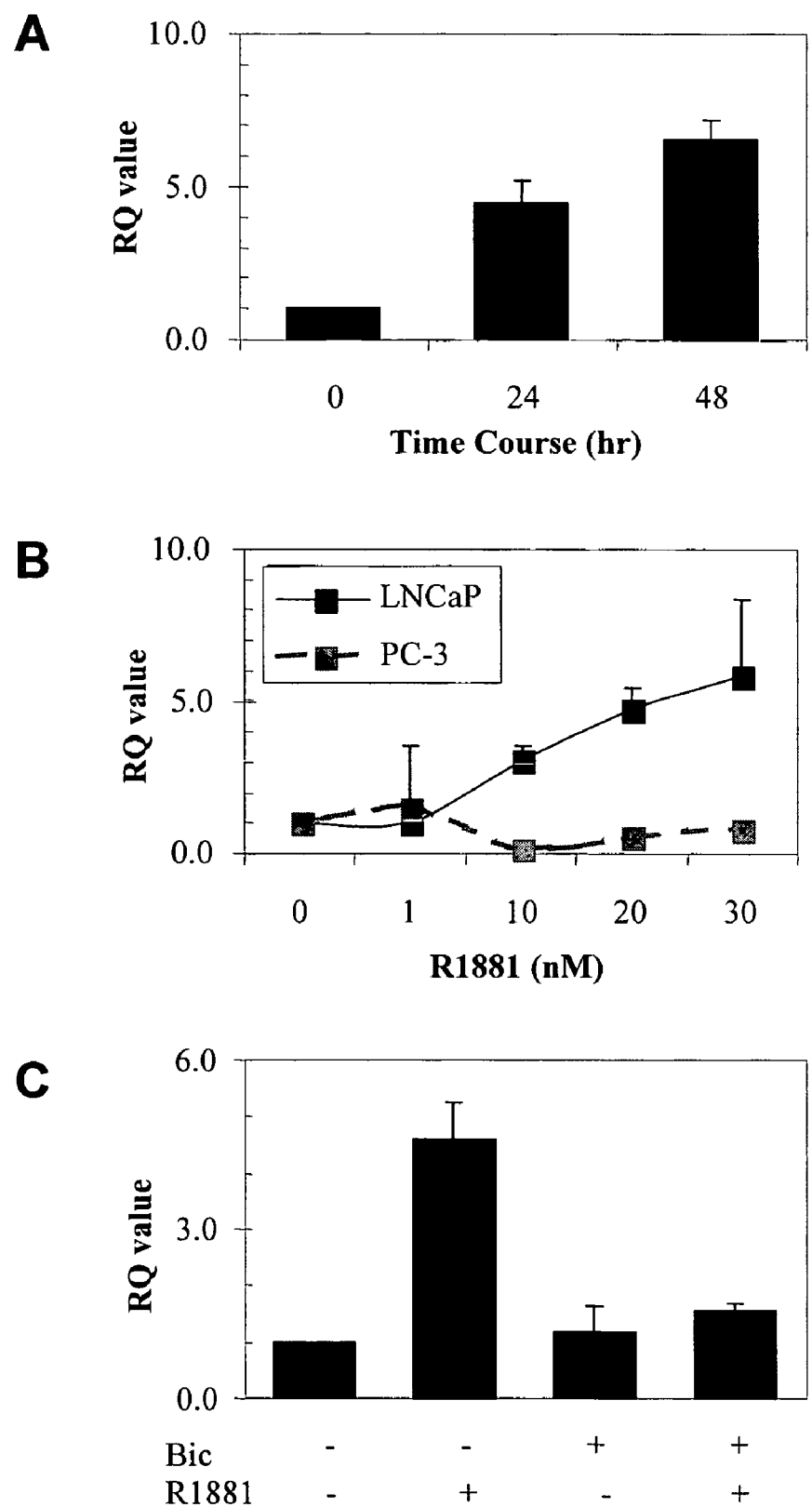
FIG. 2A-FIG. 2F show androgen-dependent and androgen-independent activation of AR increases SENP1 expression.
Figure 2:
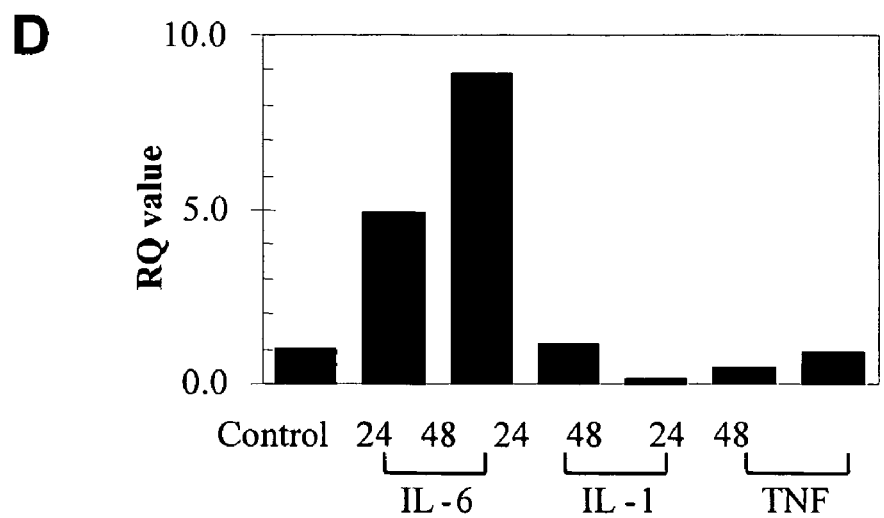
Figure 2:
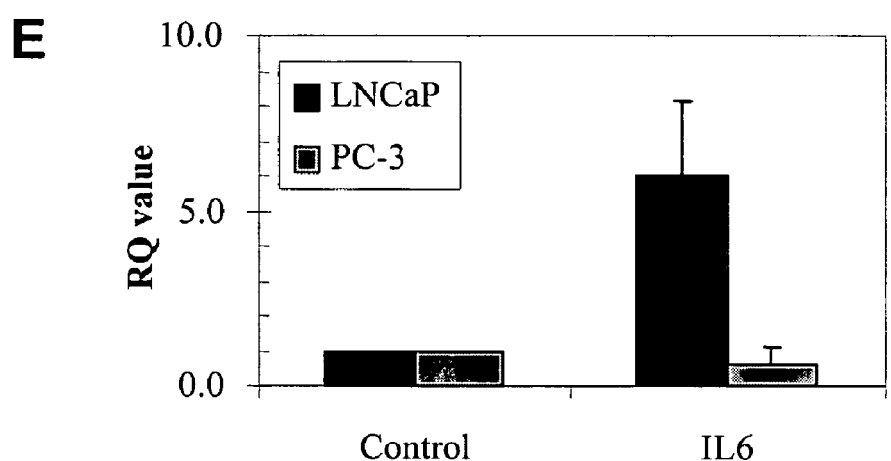
Figure 2:
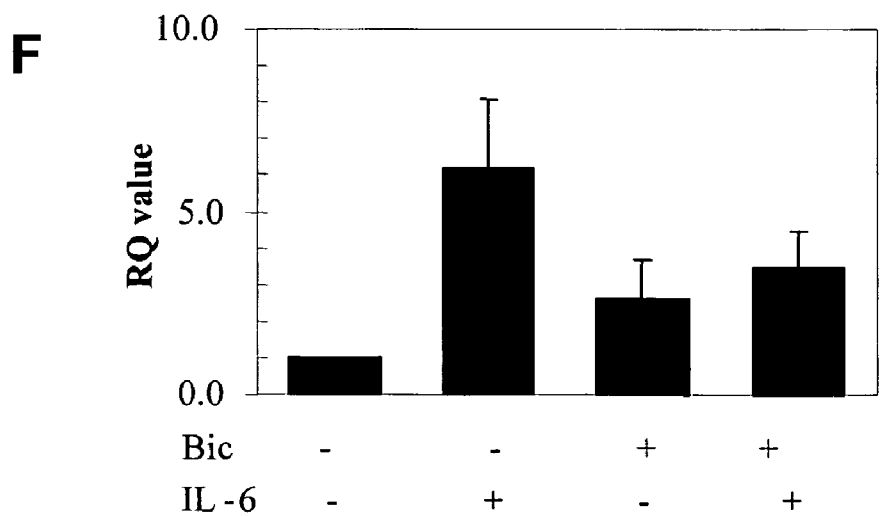

Androgen- and IL-6-Mediated Activation of the AR Promotes Elevation of SENP1 in LNCaP Cells The inventors hypothesized that activation of the AR by its native agonist androgen could upregulate SENP1 expression since the biological function of the AR is to directly modulate gene/protein expression. The human androgen-sensitive, LNCaP cells were exposed to the synthetic androgen, R1881 (20 nM), for 24 and 48 hr and SENP1 mRNA levels were evaluated using quantitative real-time PCR (QRT-PCR). SENP1 expression is enhanced by 5-fold and 7-fold with 24 and 48 hr R1881 treatments, respectively (FIG. 2A). QRT-PCR data indicated that SENP1 levels paralleled the R1881 concentration in LNCaP cells; increasing R1881 concentration elevates SENP1 levels (FIG. 2B). Hence, continuous exposure to androgen induced SENP1 expression. SENP1 expression was unaltered in the presence of AR antagonist bicalutamide (FIG. 2C) and in androgen deficient prostate cancer cells PC-3 (30 nM, FIG. 2B) indicating an AR dependent phenomenon.

Various cytokines are expressed in prostate cancer cells including IL-1, IL-6, and tumor necrosis factor-alpha (TNF-α, (Culig et al., 1998; Mizokami et al., 2000); elevated serum levels of IL-6 and TNF-α have been reported in patients with prostate cancer (Culig et al., 2003; Nakashima et al., 1998). Unlike IL-1 and TNF-α, IL-6 promotes activation of AR-dependent transcription via initiation of the MAPK and JAK/STAT pathways (Yang et al., 2003; Ueda et al., 2002; Lee et al., 2003). To determine if androgen-independent activation of the AR promotes SENP1 upregulation, LNCaP cells were treated with 25 ng/mL of IL-6, IL-1, or TNF-α for either 24 or 48 hr. SENP1 levels were enhanced in cells treated with IL-6, but not IL-1 or TNF (FIG. 2D). The contribution of the AR to IL-6-induced SENP1 enhancement was evaluated by conducting similar experiments in PC-3 cells. Unlike IL-6 treatment in LNCaP cells, SENP1 levels were unchanged in PC-3 cells pretreated with IL-6 for 24 hr (FIG. 2E). The AR antagonist bicalutamide lowered the upregulation of SENP1 mediated via chronic IL-6 treatment (FIG. 2F). Hence, induction of SENP1 was primarily via AR activation.

Example 10

Figure 3:
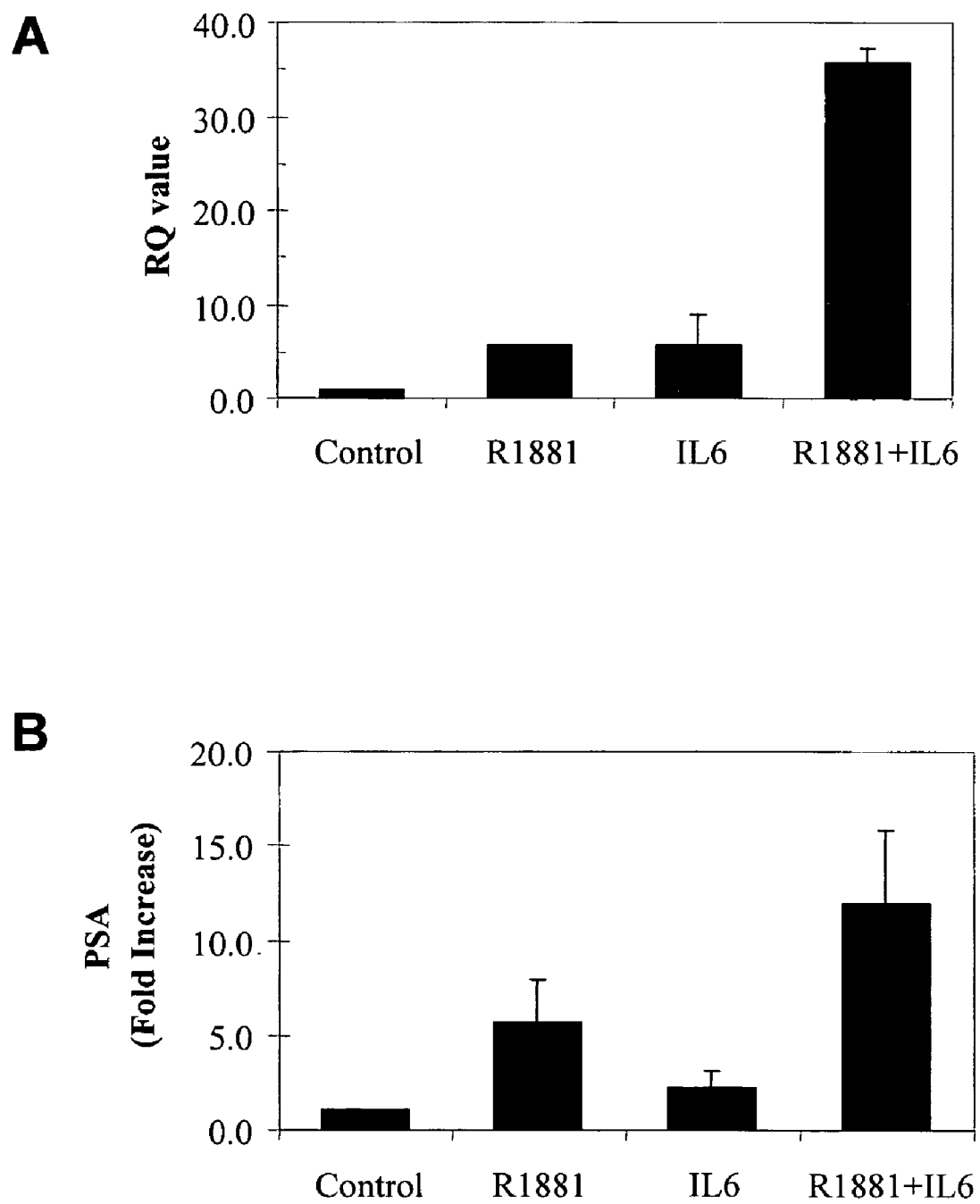
FIG. 3A-3B show combination of R1881 and IL-6 synergistically enhance SENP1 and PSA expression in LNCaP cells.
Figure 4:
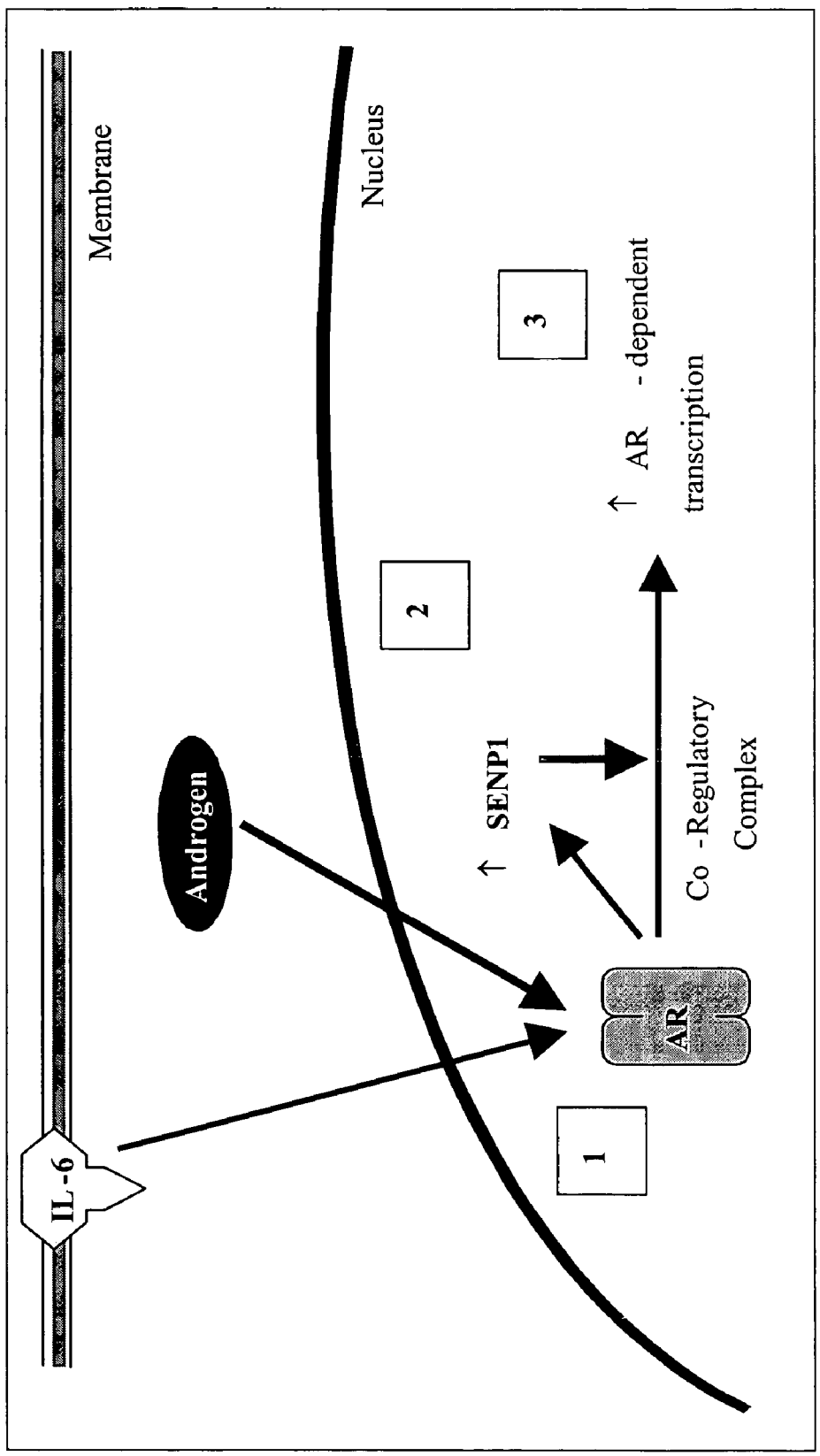
FIG. 4 shows a schematic illustration of SENP1-regulated prostate carcinogenesis. (1) Androgen-dependent, androgen-independent, or the combination of both pathways promotes activation of the AR. (2) Continuous exposure to androgen and IL-6 induces upregulation of SENP1. (3) The elevation of SENP1 in turn enhances AR transcriptional ability. The enhanced AR-dependent transcription promotes prostate carcinogenesis.

IL-6-Mediated SENP1 Enhancement is Potentiated with Concurrent Administration of Androgen The relapse of prostate cancer occurs due to the adaptation of the AR to low levels of androgen and activation via alternate pathways (Mohler et al., 2004). To evaluate whether the combination of androgen-dependent and androgen-independent pathways on AR activation could regulate SENP1 expression, SENP1 levels were assessed following treatment of LNCaP cells with R1881 (20 nM), IL-6 (25 ng/mL), or both R1881 and IL-6 for 24 hr. Treatment with either the androgen or IL-6 produced approximately a 5-fold increase in SENP1 levels (FIG. 3A). The combination of both R1881 and IL-6 led to a 35-fold induction of SENP1 expression (FIG. 3A).

To insure that the concentrations of R1881 and IL-6 were sufficient to activate AR-dependent transcription, the secretion of prostate serum antigen (PSA) was evaluated. Serum PSA levels are utilized as diagnostic tool for prostate cancer; PSA levels above 2.5 ng/mL indicate high AR activity (Canto et al., 2003). The addition of R1881 (20 nM) or IL-6 (25 ng/mL) for 24 hr significantly increased PSA protein levels as compared to control; 5.6 and 2.2 fold increase in PSA levels as compared to control, respectively (FIG. 3B). The combination of R1881 and IL-6 further potentiated the enhancement of PSA (FIG. 3B) with a 11-fold increase as compared to control. Therefore, the addition of R1881 and/or IL-6 enhanced the transcriptional activity of the AR as well as SENP1 expression.

Example 11

SENP1 is a Strong Activator of c-Jun

Figure 5:
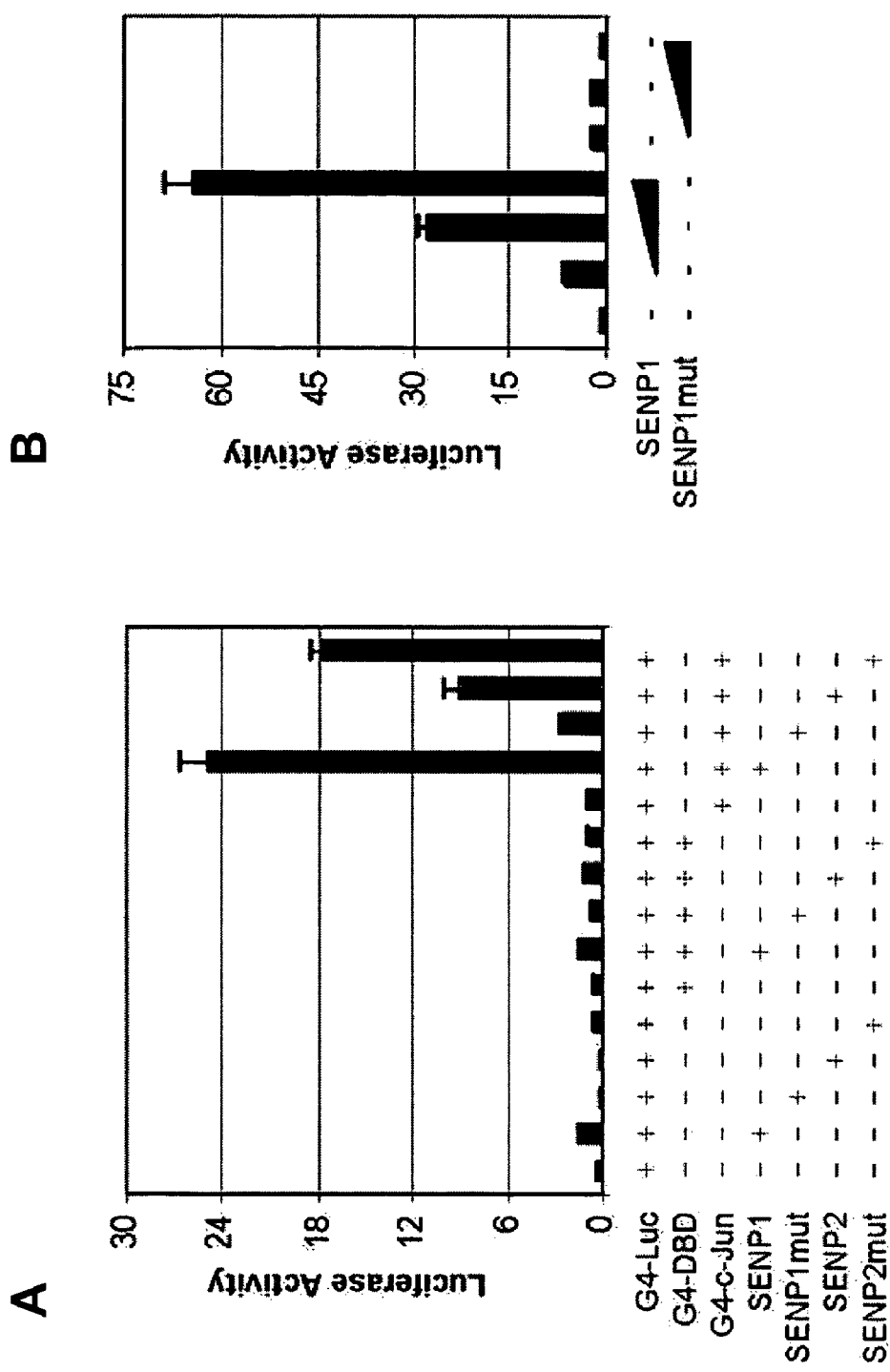
FIG. 5A-5E show that SENP1 is a strong activator of c-Jun.
Figure 5:
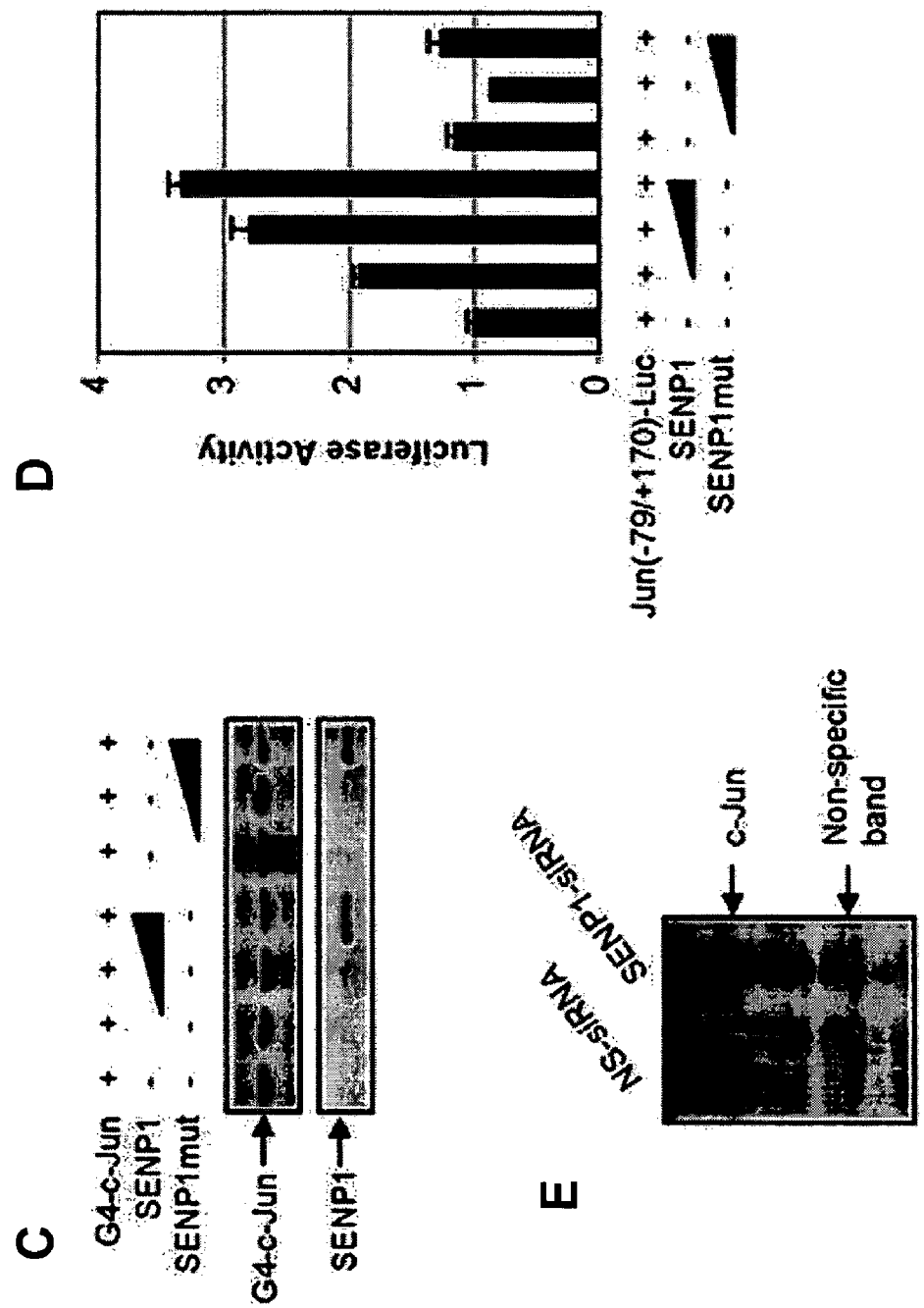

The transcription factor c-Jun is a substrate for SUMO modification (Muller et al., 2000) and has been implicated in several cellular processes including proliferation, cell survival, and cell transformation (Vogt 2001). SuPr-1, an alternatively spliced form of SENP2, could induce c-Jun-dependent transcription (Best et al., 2002). Since both SENP1 and SENP2 belong to the SUMO-specific protease family with broad substrate specificity (Yeh et al., 2000), the inventors speculated that SENP1 might also be an activator of c-Jun. To test this hypothesis, the inventors performed a luciferase reporter gene assay by using Gal4 fused to the transactivation domain (1-223) of c-Jun (G4-c-Jun) and the Gal4-Luciferase reporter plasmid. When expressed in PC-3 cells, SENP1 markedly induced G4-c-Jun-dependent transcription (FIG. 5A), but not G4-DBD. SENP1 exhibited stronger activation of c-Jun-dependent transcription than SENP2. Titration of SENP1 showed a dose-dependent effect of SENP1 on c-Jun-dependent transcription (FIG. 5B). The effects of SENP1 in different cell lines, such as 293, MCF-7, Hela, and U-2OS cells, were tested, and cell type specificity was not observed. These results suggested that SENP1 can function as a strong activator of c-Jun-dependent transcription.

A previous study indicated that desumoylation activity was not required for SuPr-1, a splice variant of SENP2, to induce c-Jun activity (Best et al., 2002). The inventors found that SENP2's catalytic mutant actually induced more c-Jun activity than wild-type SENP2 (FIG. 5A). In contrast to SENP2, SENP1's action on c-Jun was dependent on its catalytic activity, as the catalytic inactive mutation markedly reduced the effect of SENP1 on c-Jun-dependent transcription (FIG. 5A). The inventors validated this result by increasing the amount of SENP1 mutant transfected, which did not enhance c-Jun-dependent transcription (FIG. 5B). Western blotting showed that the wild-type and mutant SENP1 were expressed at similar levels and did not alter G4-c-Jun expression (FIG. 5C). These data suggested that SENP1's action on c-Jun-dependent transcription, unlike that of SENP2, was mediated through a desumoylation mechanism.

To determine whether SENP1 could affect transcription of an endogenous promoter, the inventors examined the effect of SENP1 on c-Jun promoter (−79/+170) which contains c-Jun binding sites in the −72 position (Han et al., 1992; Angel et al., 1988). As shown in FIG. 5D, SENP1 induced c-Jun promoter activity in a dose-dependent manner. The catalytic activity of SENP1 was also required for this effect. To further confirm the effect of SENP1 on c-Jun promoter, the inventors used siRNA to silence endogenous SENP1 and then examined whether the expression of endogenous c-Jun was affected. The transfection of SENP1-specific siRNA plasmid into PC-3 cells decreased endogenous SENP1 expression by 53% (real-time PCR analysis), while expression of SENP1-siRNA reduced endogenous c-Jun expression by 60% (FIG. 5E). Collectively, these data indicated that SENP1 strongly activated c-Jun-dependent transcription through its desumoylation activity.

Example 12 p300 is Essential for Induction of c-Jun Activity by SENP1

Figure 6:
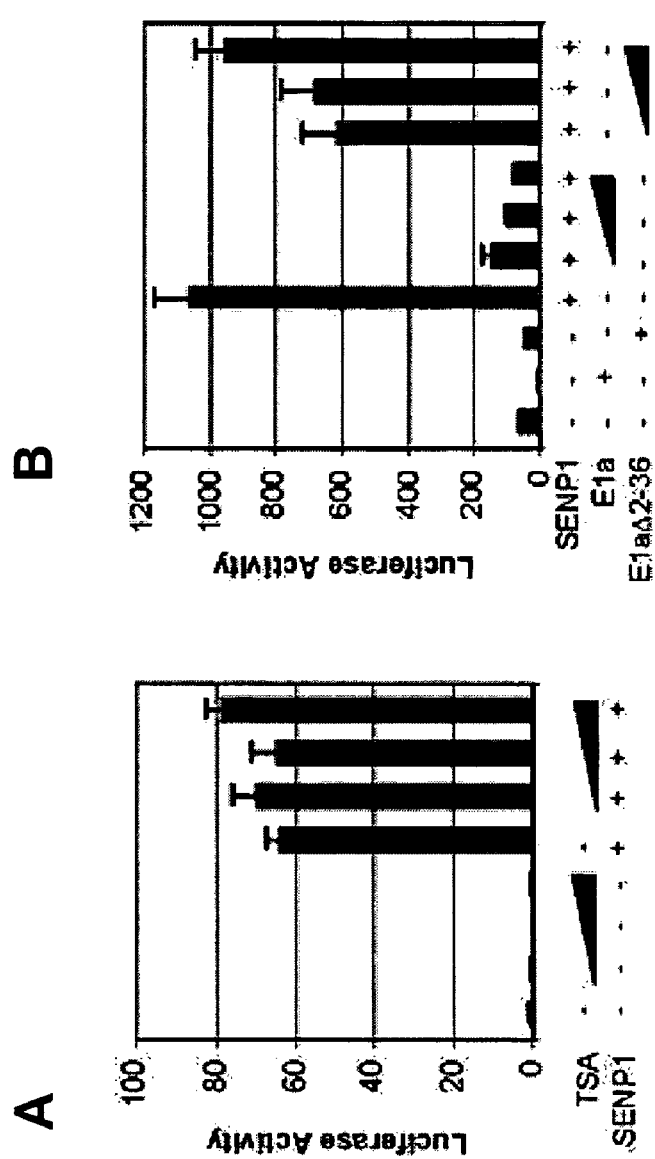
FIG. 6A-6C show that p300 is involved in the activation of c-Jun by SENP1.

Another important regulator of c-Jun activity is p300, which can interact with c-Jun and enhance c-Jun-dependent transcription, providing an additional mechanism for the regulation of c-Jun-dependent transcription (Lee et al., 1996). Importantly, p300 could be modified by SUMO, and sumoylation of p300 is essential for the cis-repression function of CRD1 on p300 transactivation (Girdwood et al., 2003). Since adenovirus E1A specifically interacts with p300 and inhibits p300 activity (94-97), it was tested whether E1A could inhibit SENP1 activity on G4-c-Jun. As shown in FIG. 6B, overexpression of E1A strongly repressed c-Jun-dependent transcription (lane 2 vs. 1), while E1AΔ2-36, a p300 binding-defective mutant (Lundblad et al., 1995), did not. This suggested that p300 was a crucial cofactor for G4-c-Jun transcriptional activity. When SENP1 was co-expressed with E1A, the enhancement of G4-c-Jun transcription by SENP1 was almost completely inhibited (FIG. 6B). The inventors further confirmed that the effect of E1A was dependent on its ability to bind to p300 by using E1AΔ2-36. The effect of E1A on SENP1 was severely impaired by mutation of the p300 binding region of E1A (FIG. 6B). These results suggested that SENP1 action on G4-c-Jun activity was mediated by p300.

It was further tested whether the effect of SENP1 on G4-c-Jun could be enhanced by overexpression of p300. As shown in FIG. 6C, p300 synergized with SENP1 in enhancing G4-c-Jun-mediated transcription. Overexpression of p300 alone could induce G4-c-Jun activity by 3.5-fold. In the presence of SENP1, however, the transactivation activity of p300 was enhanced 6.1-fold. The effect of SENP1 was dependent on its catalytic activity, because the p300 could not enhance transcription in the presence of the SENP1 catalytic mutant (FIG. 6C). These data indicated that SENP1's ability to enhance G4-c-Jun transcription was mediated through desumoylation of p300.

Example 13

SENP1 Action on c-Jun is Mediated Through the CRD1 Domain of p300

Transactivation of p300 is repressed by the CRD1 domain of the p300 protein and two sumoylated sites have been identified in the CRD1 domain (Girwood et al., 2003). The repressive function of CRD1 was mediated by SUMO modification at these two sumoylation sites (Girwood et al., 2003). To determine whether G4-c-Jun activity could be affected by the CRD1 domain of p300, a CRD1-deleted mutant of p300 was used to test transactivation of the G4-c-Jun reporter system. In comparison to wild-type p300, CRD1-deleted mutant of p300 increased more activity of G4-c-Jun. Deletion of the CRD1 domain increased the transactivation of p300 by 1.5 to 2.3-fold (FIG. 7A), indicating that the CRD1 domain repressed p300 transactivation on G4-c-Jun-dependent transcription.

Figure 7:
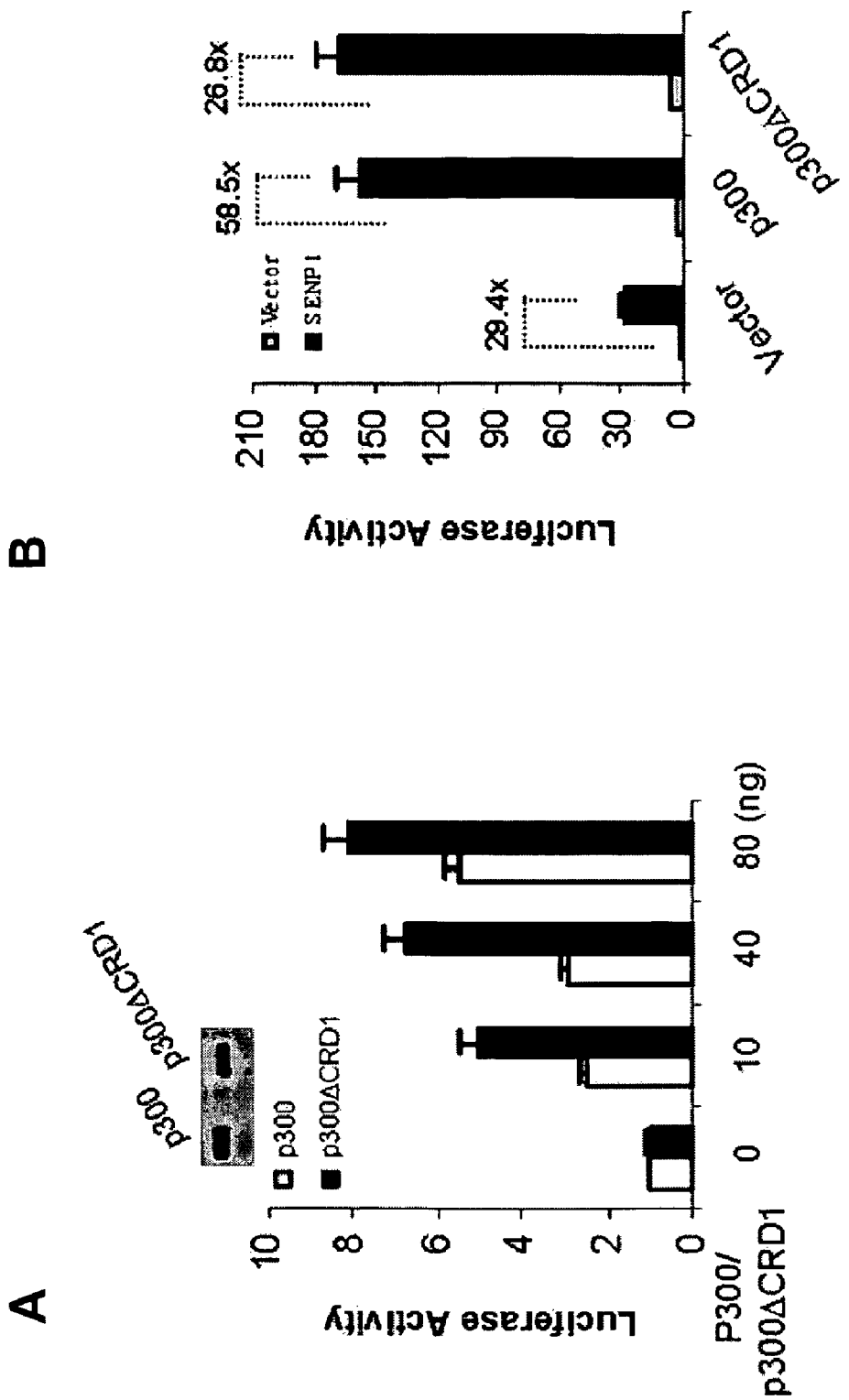
FIG. 7A-7B show that SENP1 action on c-Jun is mediated through the CRD1 domain of p300.

Next, it was examined whether the CRD1 domain was required for SENP1 action on c-Jun activity. G4-c-Jun reporter plasmids were co-transfected into PC-3 cells with wild-type p300 or the CRD1-deleted mutant. As shown in FIG. 7B, the p300 mutant transactivated G4-c-Jun more than the wild-type. SENP1 alone induced G4-c-Jun activity by 29.4-fold, whereas overexpression of wild-type p300 increased the activity of SENP1 on G4-c-Jun by as much as 58.5-fold. Moreover, deletion of CRD1 decreased SENP1 induction to 26.8-fold. These results suggested that the CRD1 domain of p300 mediates SENP1's action on G4-c-Jun.

Example 14

SENP1 Increases p300 Transactivation by Desumoylating the CRD1 Domain

Figure 8:
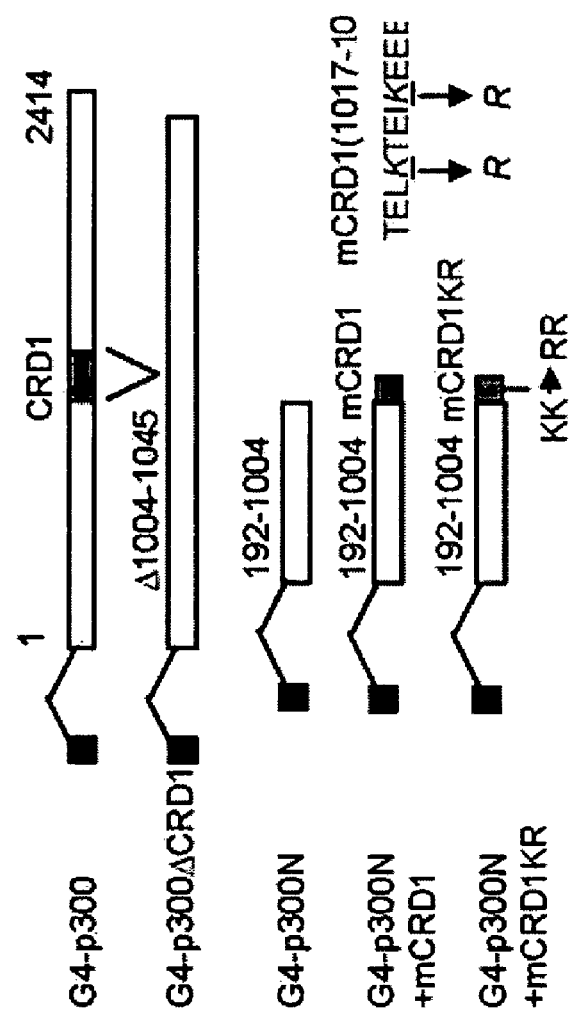
FIG. 8A-8D show that SENP1 increase p300 transactivation by desumoylating the CRD1 domain.
Figure 8:
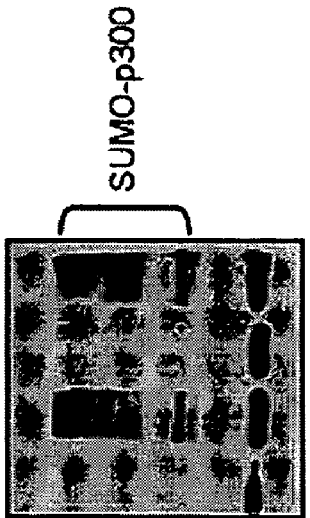
Figure 8:
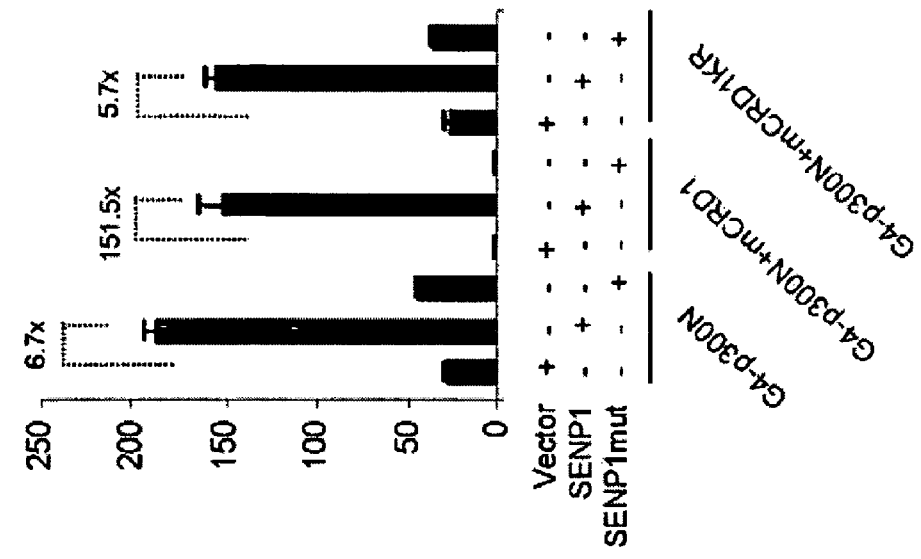
Figure 8:
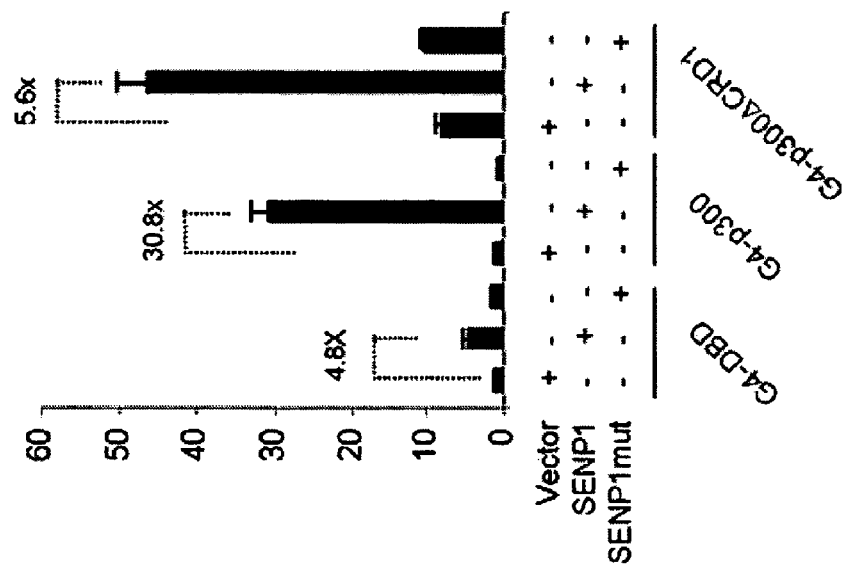

Next, the inventors determined whether the CRD1 domain is the target of SENP1's desumoylation activity. SENP1 was co-expressed with His-p300 (1-1045), a fragment containing the CRD1 domain, and HA-SUMO-1 in COS-7 cells. As shown in FIG. 8A, p300 (1-1045) was conjugated by SUMO-1 (lane 2). SENP1 removed all SUMO-conjugated bands (lane 3), but SENP1 mutant did not (lane 4). These results clearly show that SENP1 desumoylates p300.

To determine a direct effect of SENP1 on p300 activity, the inventors used the Gal4-DBD reporter system, in which p300 is tethered to DNA via a fusion to the Gal4 DNA-binding domain (FIG. 8B). When expressed in PC-3 cells, SENP1 induced the G4-p300 activity by 30.8-fold, but SENP1 mutant did not (FIG. 8C). Deletion of the CRD1 domain increased p300 transactivation by 8-fold, whereas it severely impaired the effect of SENP1 on p300 transactivation (FIG. 8C). These data suggested that the CRD1 domain was required for SENP1's action on p300 transactivation.

To further determine whether SENP1 action was mediated through desumoylating the CRD1 domain of p300, a Gal4-p300N+minimal CRD1 domain (mCRD1) fusion construct was used. The mCRD1 was required for CRD1-mediated repression and contains two sites for SUMO modification (Girwood et al., 2003) (FIG. 8B). The p300N+mCRD1 fusion protein exhibited only 4% of the activity of p300N (FIG. 8D). Expression of SENP1, but not SENP1 mutant, however, completely reversed mCRD1 repression up to the level of p300N (FIG. 8D). Substitution of both Lys of mCRD1 by Arg (FIG. 8B) completely relieved its repression and reduced the effect of SENP1 on p300 transactivation (FIG. 8D). These data suggested that SENP1's action on p300 transactivation was mediated through desumoylation of the CRD1 domain.

Example 15

SENP1 Induces Cyclin D1 Expression and Cell Proliferation

Figure 9:
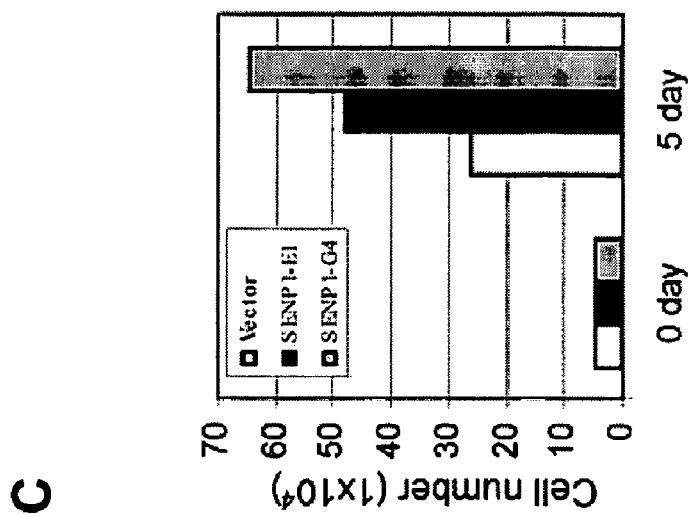
FIG. 9A-9C show that SENP1 induces cyclin D1 expression and cell proliferation.
Figure 9:
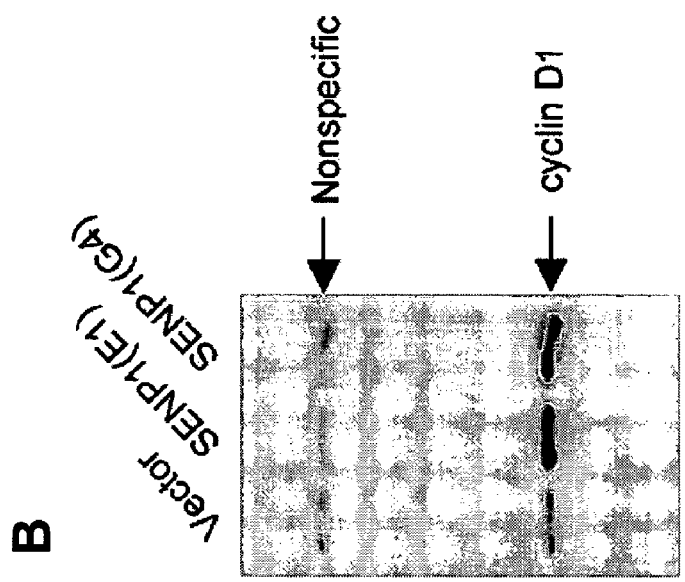
Figure 9:
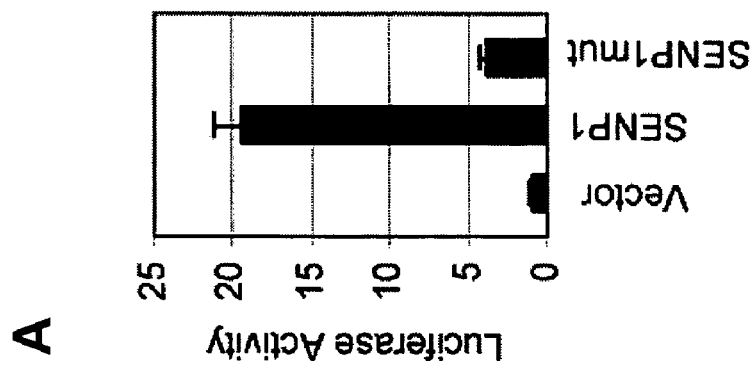

Since the yeast SUMO-specific protease Ulp1 is implicated in cell cycle regulation, the inventors speculated that SENP1 might also regulate the mammalian cell cycle by affecting the expression of cell cycle regulators. To test this hypothesis, the inventors performed a luciferase reporter gene assay using cyclin D1 promoter (−1745/+130)-driven luciferase plasmid. When expressed in PC-3 cells, SENP1 markedly induced cyclin D1 promoter-dependent transcription (FIG. 9A). SENP1's action on cyclin D1 promoter was dependent on its catalytic activity, as the catalytic inactive mutant markedly reduced the effect of SENP1 on cyclin D1 promoter-dependent transcription. The effects of SENP1 in different cell lines, such as LNCaP, 293, MCF-7, and Hela cells, were tested, and cell type specificity was not observed. These results suggested that SENP1 can function as a strong activator of cyclin D1 expression.

To further confirm that SENP1 induces endogenous cyclin D1 expression, the inventors generated GFP-tagged SENP1- and empty GFP vector-stable transfected LNCaP cell lines. After using G-418 selection and GFP sorting, the inventors obtained two SENP1 stable transfected clones (E1 and G4) and one vector stable transfected clone. The inventors examined the endogenous cyclin D1 expression in these clones. As shown in FIG. 9B, the expression of endogenous cyclin D1 in SENP1 over-expressing clones (E1 and G4) was increased ~3-fold in comparison to vector control clone.

The inventors examined the growth of SENP1 stably transfected clones and the vector control clone. 5 days after plating, the cell number of the two SENP1 clones is 1.8~2.5 folds more than that of the vector clone, indicating SENP1 overexpression increased cell proliferation (FIG. 6C).

Example 16

SENP1 Enhances AR-Dependent Transcription

Luciferase reporter gene assays were used to examine whether SENP1 could affect AR-dependent transcription. AR and ARE-luciferase reporter plasmids (ARE-Luc) were co-transfected into PC-3 cells with plasmids encoding either SENP1 or SENP1 catalytically inactive mutant. As shown in FIG. 9A, SENP1 dramatically enhanced AR transcriptional activity by 45-fold. This effect was dependent on the presence of AR ligand, R1881. SENP1's catalytic activity was required for this effect, as the catalytically inactive mutant of SENP1 (R630L, K631M) has a minor effect on AR-dependent transcription (FIG. 9A, bottom panel, lane 8 vs. 9). Titration of SENP1 showed a dose-dependent response of SENP1 action on AR-dependent transcription (FIG. 9B). Even at very low levels of cotransfected DNA, SENP1 induced AR transactivation. In contrast, increasing levels of the SENP1 mutant did not alter significantly AR-dependent transcription (FIG. 9B) further validating the need of SENP1's enzymatic activity in the transcriptional regulation of AR. As the antagonists of androgen can also bind to the AR, the inventors tested whether SENP1 could act on antagonist-bound AR. As shown in FIG. 9C, no effect of SENP1 on AR-dependent transcription was noted in the presence of bicalutamide. The enhancement of AR transcriptional activity by SENP1 was specific, as SENP2 and SENP3, the other member of SENPs family, only modestly enhanced AR-dependent transcription (FIG. 9D). Western analysis demonstrated that AR protein levels were not affected by exogenous expression of SENP1, SENP1 mutant (FIG. 9A, 9E), SENP2, or SENP3 (FIG. 9F). SENP1 and SENP1 mutant were expressed at similar levels (FIG. 9E) and SENP1 and SENP2 were also expressed similarly (FIG. 9F).

The promoter of rat probasin, another AR target gene-driven luciferase, was used to test the effect of SENP1 on AR transactivation. SENP1 could also increase AR-dependent transcription (FIG. 9G). Thus, the effect of SENP1 was generalized to at least two AR-dependent promoter systems.

Example 17

SiRNA Effects AR-Dependent Transcription

Figure 10:
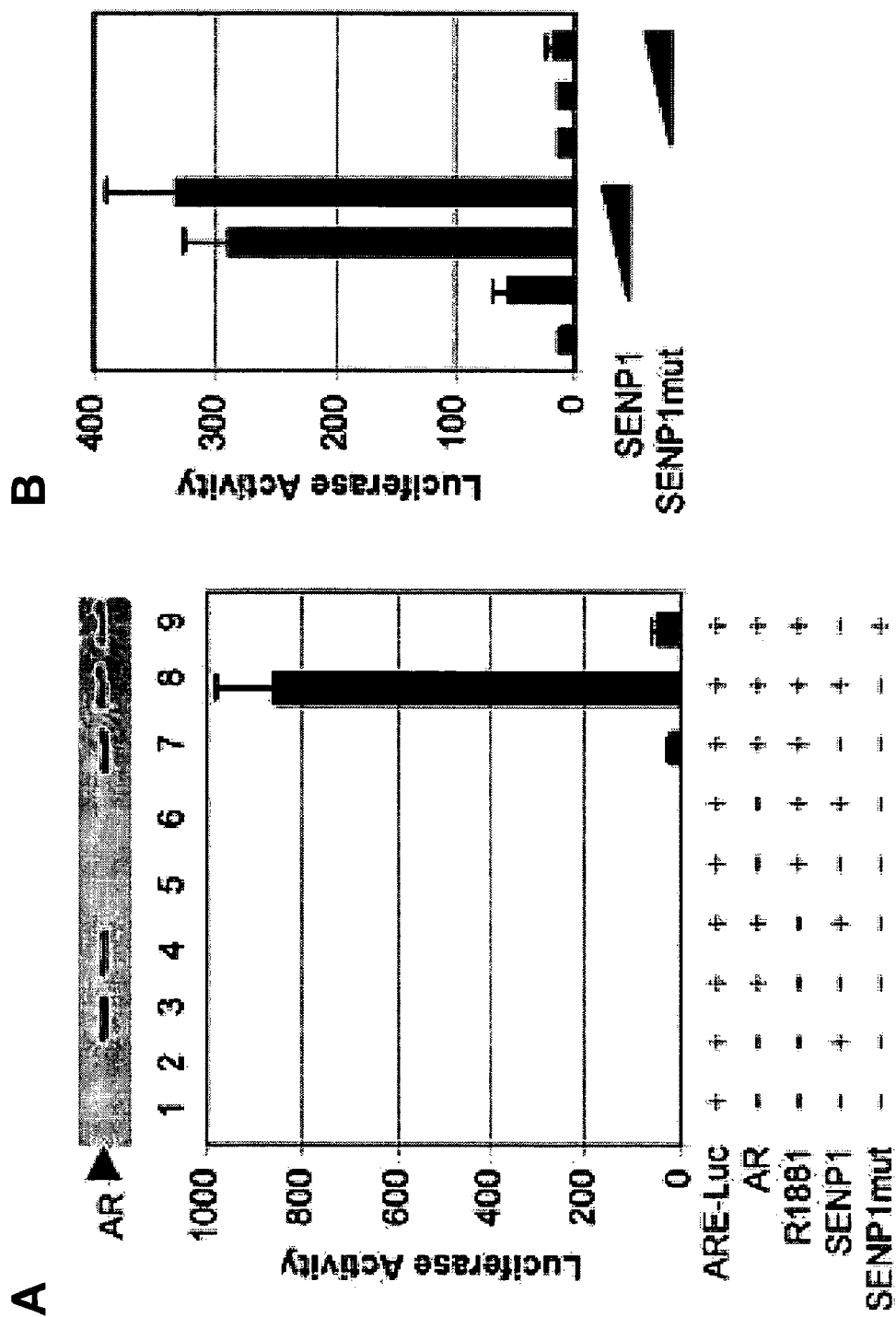
FIG. 10A-10G show that SENP1 enhances AR-dependent transcription.
Figure 10:
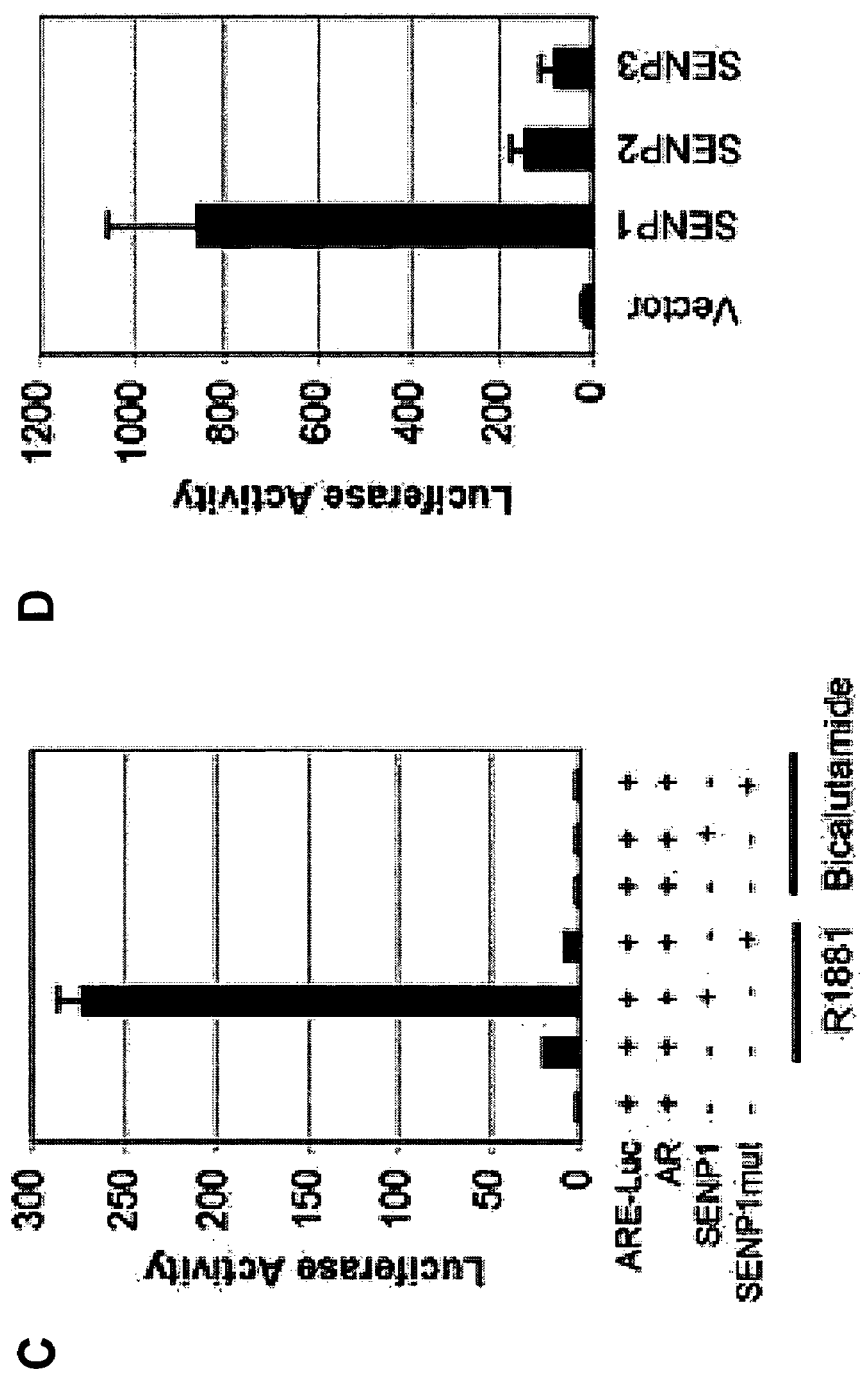
Figure 10:
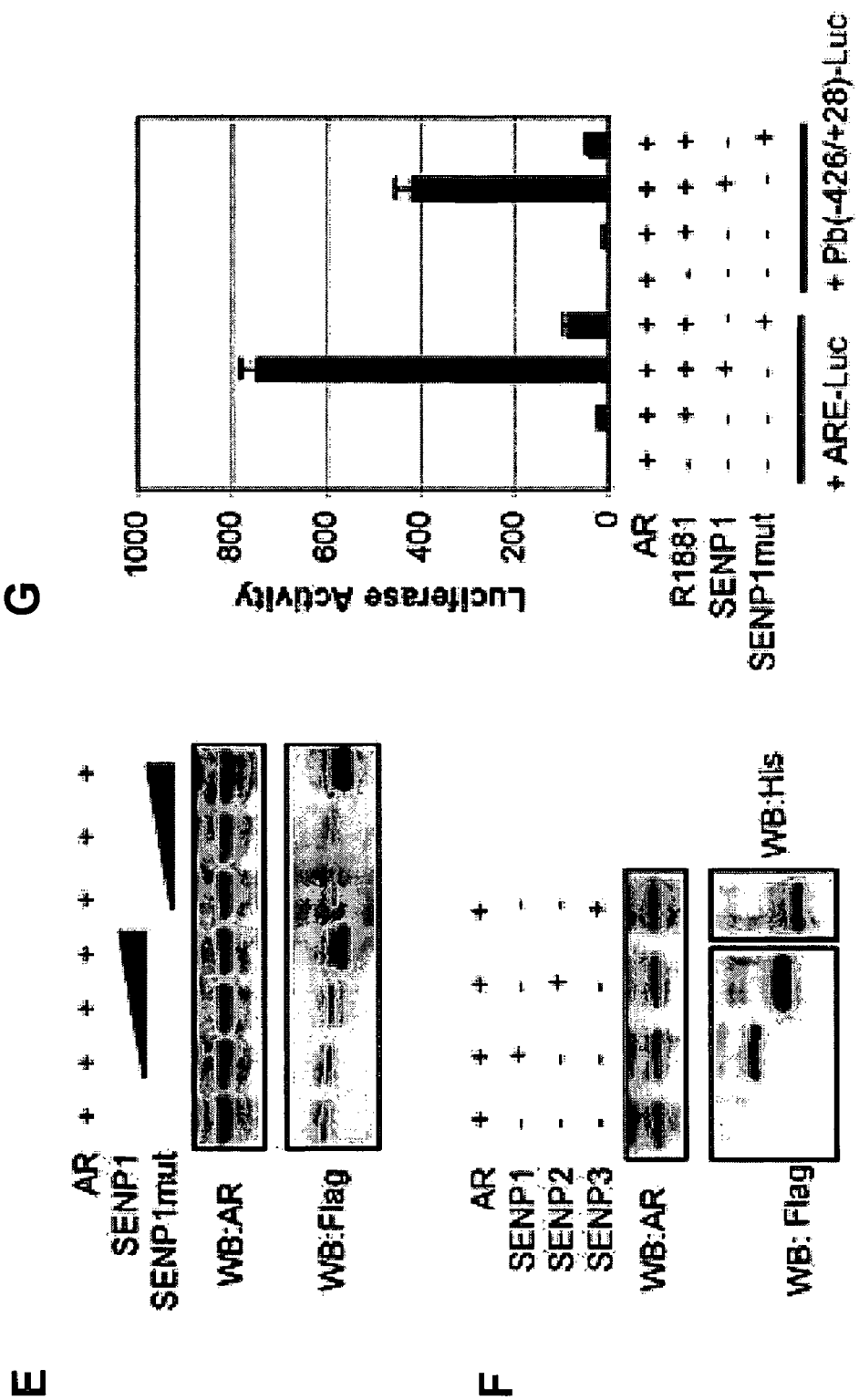

ARE-luciferase reporter assays were also used in AR positive cell line LNCaP cell. In the presence of ligand, expression of SENP1 induced endogenous AR activity by 7-fold (FIG. 10A). This effect was also dependent on SENP1 catalytic activity, as SENP1 mutant has a minor effect (FIG. 10A).

The effects of SENP1 on an endogenous androgen-responsive gene PSA expression in LNCaP cells were examined. As PSA is a secreted protein, an ELISA assay was used to examine the PSA secretion in the cultural medium. As showed in FIG. 10B, the concentration of secreted PSA protein in the cultural medium was increased by R1881. The increase was further enhanced in the SENP1 transfected cell, but not in the SENP1 mutant transfected cell (FIG. 10B). To further confirm the effect of SENP1 in regulation of AR-dependent transcription, an siRNA molecule (SEQ. ID. NO. 7) was used to silence endogenous SENP1 in LNCaP cells. As expected, PSA expression was decreased in SENP1-siRNA-transfected cells (FIG. 10C). The level of endogenous SENP1 mRNA in LNCaP cells transfected with SENP1 siRNA plasmid was decreased by 53% (FIG. 10D). Collectively, these data indicated that SENP1 acts as strong activator for AR-dependent transcription and the catalytic activity of SENP1 is required for this action.

Example 18

HDAC1 can be Desumoylated by SENP1 In Vivo

Figure 11:
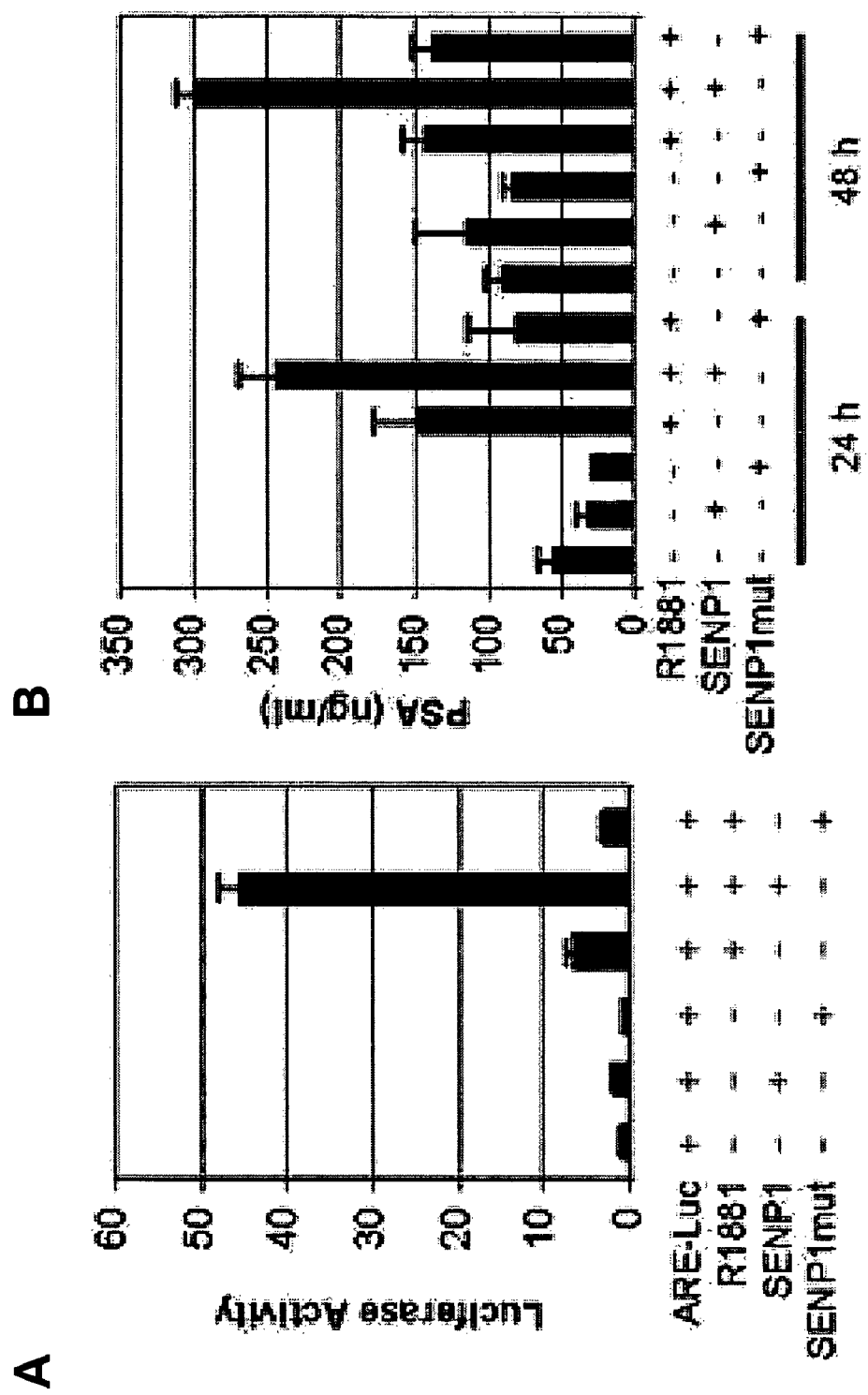
FIG. 11A-11D show that SENP1 increases PSA expression.
Figure 11:
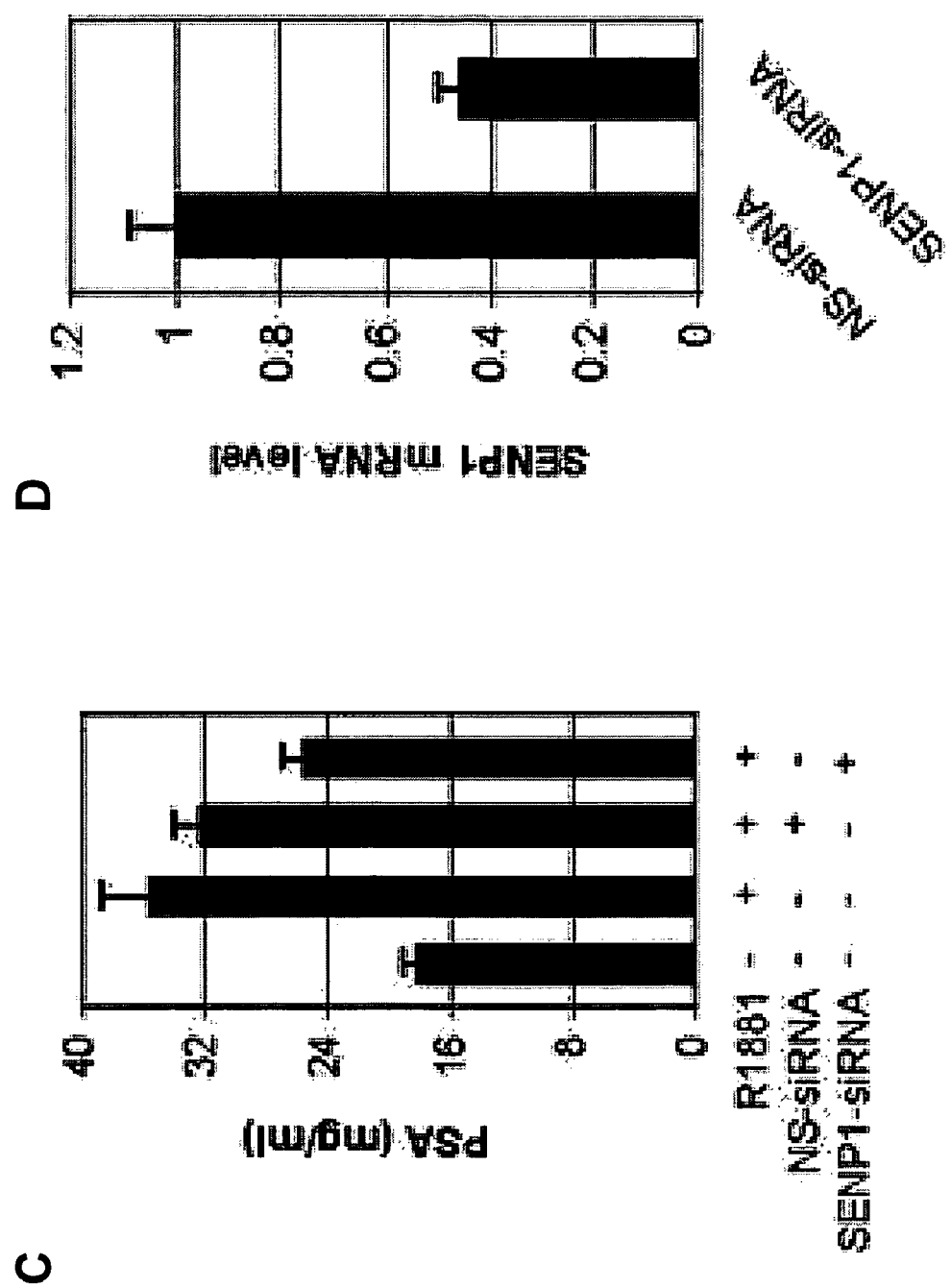

Since it was determined that SENP1's enhancement of AR-dependent transcription is independent of the sumoylation status of AR, histone deacetylases were examined to determine if they are responsible for the enhancement of AR-dependent transcription by SENP1. There are at least 10 histone deacetylases in the mammalian genome (de Ruijter et al., 2003). Both HDAC1 and HDAC2 are involved in the formation of repression complex for the AR (Shang et la., 2002), but only HDAC1 could be conjugated by SUMO (Chauchereau et al., 2003). Thus, HDAC1 could be a potential mediator in SENP1's enhancement of AR-dependent transcription. To test this hypothesis, it was first determined whether HDAC1 could associate with SENP1 in vivo. HDAC1 co-precipitated with SENP1 in cell extracts (FIG. 11A, lane 4). Next, it was determined whether HDAC1 could be desumoylated by SENP1. As shown in FIG. 11B, HDAC1 was sumoylated and that sumoylated HDAC1 was deconjugated by SENP1 (FIG. 11B, top panel). This was dependent on SENP1's catalytic activity because SENP1 mutant did not deconjugate sumoylated HDAC1 (FIG. 11B, top panel). HDAC1 levels were also evaluated to ensure that immunoprecipitates were equally loaded in all lanes (FIG. 11B, bottom panel).

Example 19

SENP1 Inhibits HDAC1's Transcriptional Repression

Figure 12:
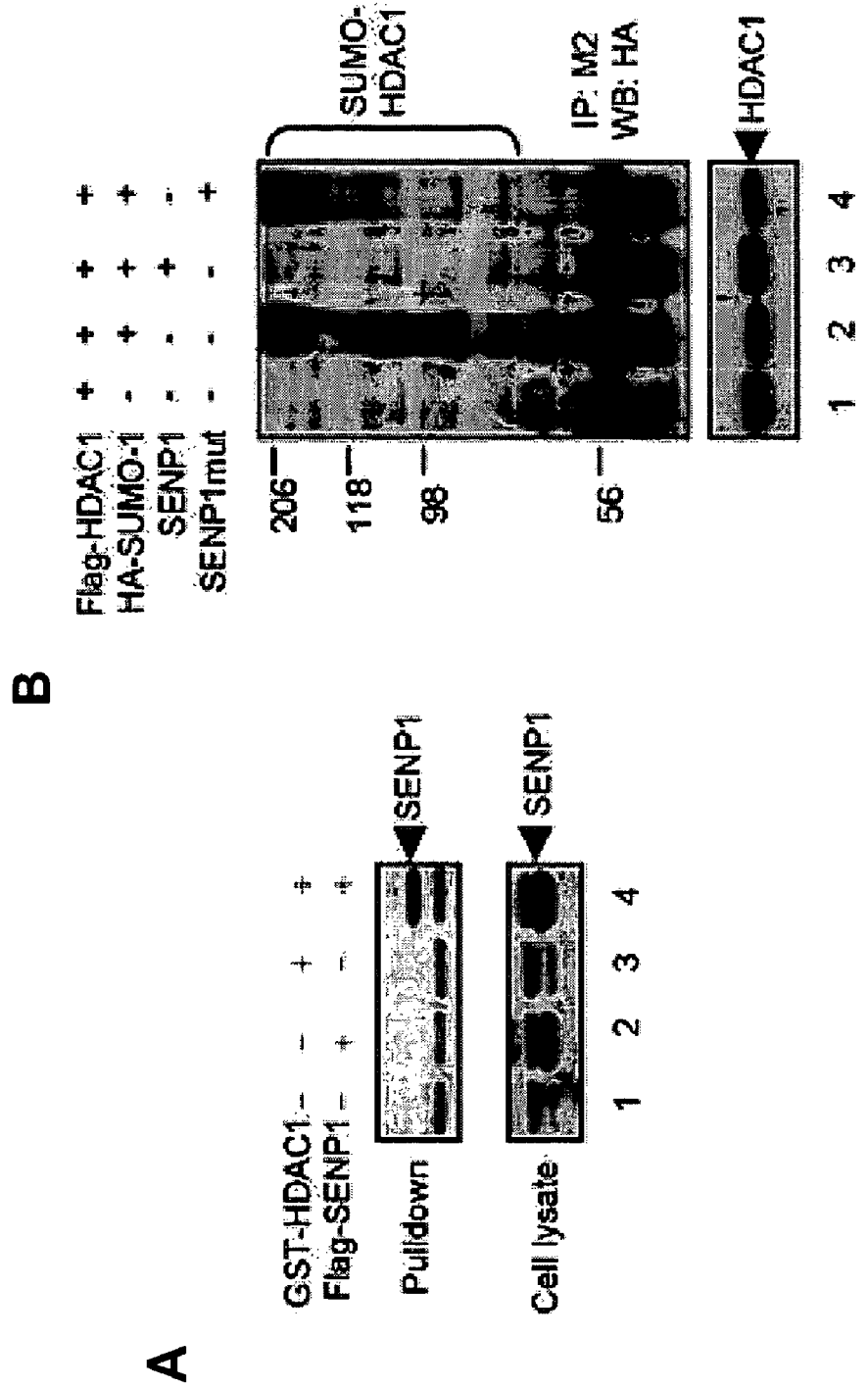
FIG. 12A-12E show SENP desumoylates HDAC1 and inhibits HDAC1 repressive activity.
Figure 12:
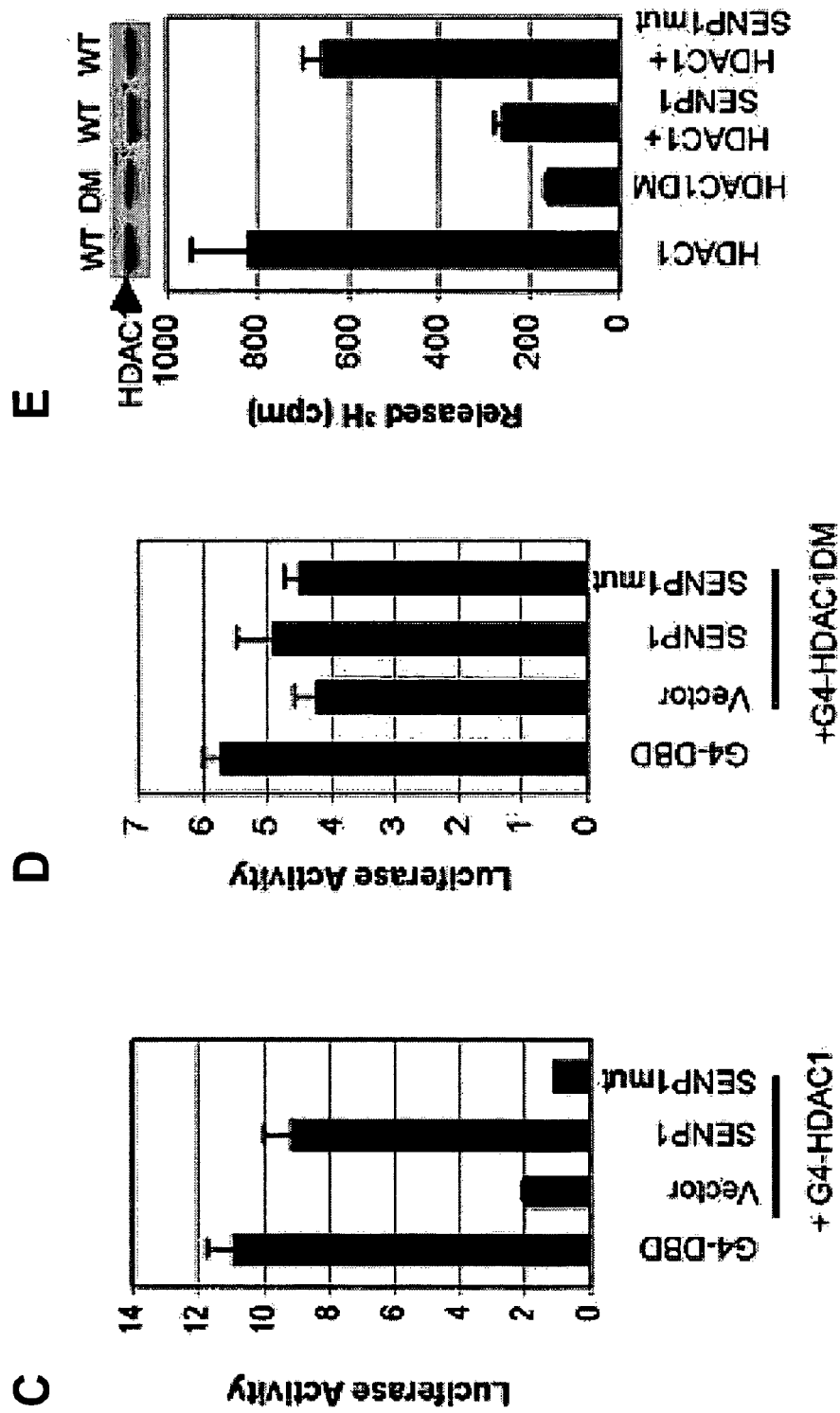

Two approaches were used to determine whether SENP1 could affect HDAC1's transcriptional repressive activity. First, a Gal4-DBD reporter system in PC-3 cells was used. HDAC1 tethered to DNA via fusion to Gal4-DBD was shown to repress the reporter gene activity driven by a minimal promoter harboring 5×Gal4 binding sites (David et al., 2002) (FIG. 12C). Co-expression of SENP1 strongly overcame the HDAC1-mediated transcriptional repression, whereas SENP1 mutant could not overcome this effect (FIG. 12C). To further determine whether SENP1 action was through the desumoylation of HDAC1, the inventors used a Gal4-DBD fused HDAC1 mutant (HDAC1 DM), where two major sumoylation sites, K444 and K476, were substituted by Arg, and tested the activity using the same assay. The sumoylation site mutant has minimal repressive activity (FIG. 12D). Co-expression of SENP1 had no effect on the repression of HDAC1 DM (FIG. 12D), suggesting that the SENP1 action was mainly mediated through the direct desumoylation of HDAC1. The second approach was to examine the effect of SENP1 on HDAC1 deacetylase activity, which was believed to be the major repressive mechanism for transcription. In the presence of SENP1, the deacetylase activity of HDAC1 precipitates had a 70% reduction (FIG. 12E). In contrast, expression of SENP1 mutant did not affect HDAC1's deacetylase activity (FIG. 12E). The inventors also examined the deacetylase activity of HDAC1 DM and showed that this mutant had a markedly reduced histone deacetylase activity (FIG. 12E). Collectively, these data indicated that SENP1 inhibited the repressive effect of HDAC1 through desumoylation of HDAC1.

Example 20

HDAC1 Mediates SENP1 Action on AR-Dependent Transcription

Figure 13:
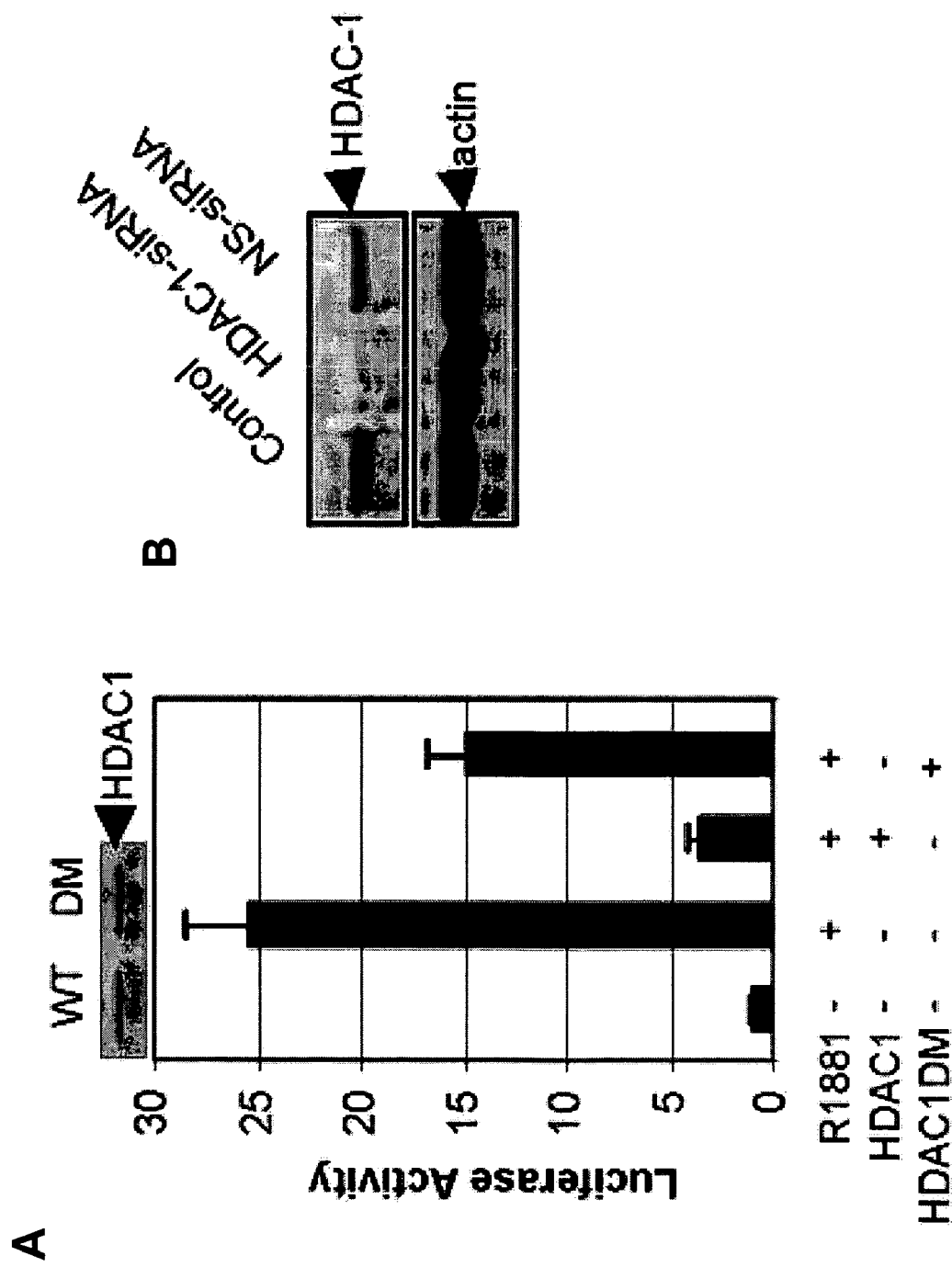
FIG. 13A-13D show that HDAC1 is required for SENP1's effect on AR transactivation.
Figure 13:
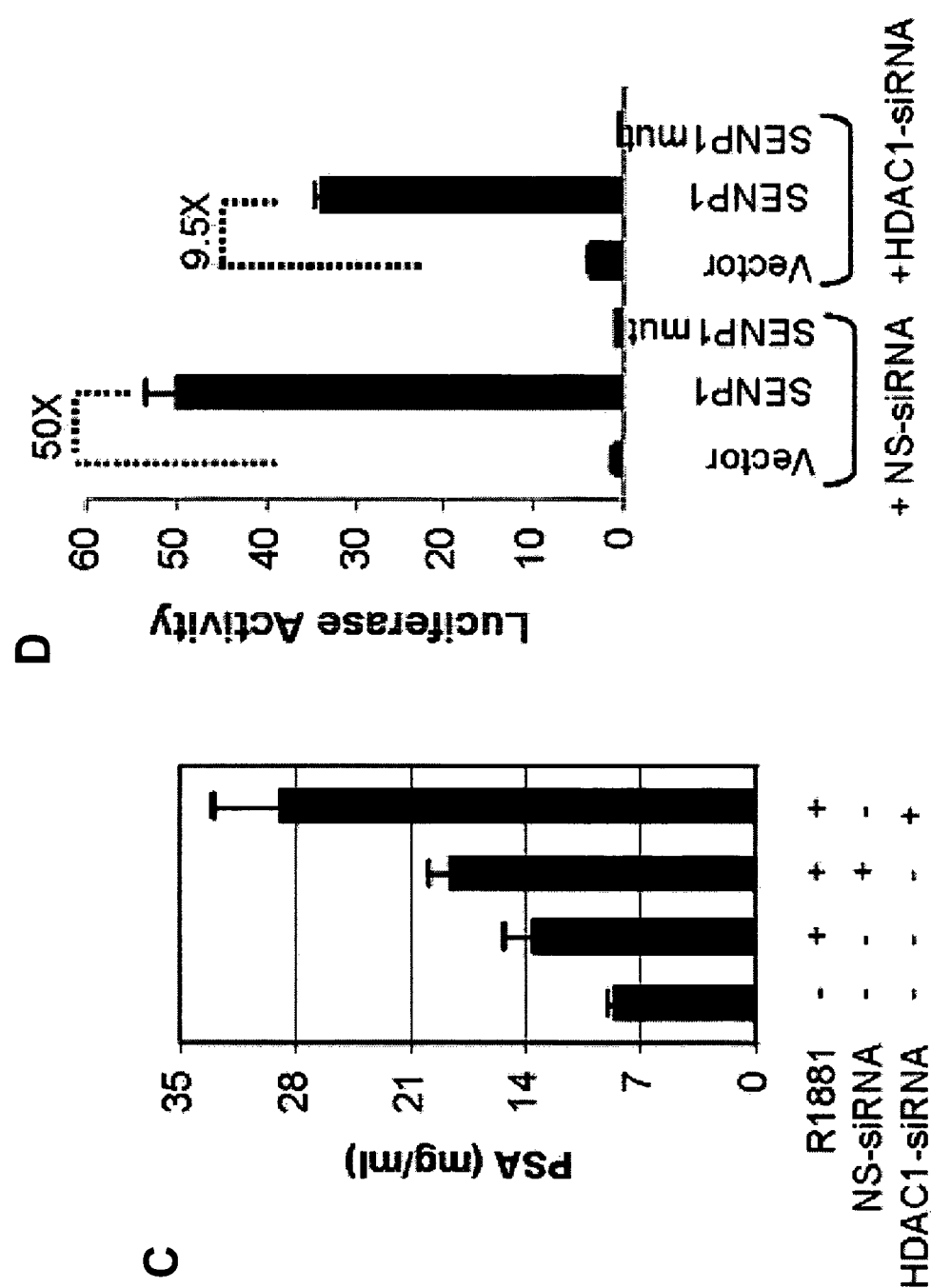

To further confirm that desumoylation of HDAC1 was required for SENP1 to overcome HDAC1's repressive effect on AR-dependent transcription, the inventors compared the repressive effect of HDAC1 DM to HDAC1 wild-type on AR-dependent transcription. As shown in FIG. 13A, while HDAC1 wild-type repressed the AR activity up to 90%, the HDAC1 mutant lost 50% repression activity on AR transactivation. These data indicated that SENP1's ability to inhibit HDAC1's repressive effect was mediated in part through desumoylation of HDAC1.

To confirm that HDAC1 was required for the enhancement of AR-dependent transcription by SENP1, the inventors determined the effect of SENP1 on AR-dependent transcription with HDAC1 siRNA duplexes to knock down the expression of endogenous HDAC1. The expression of endogenous HDAC1 was markedly decreased by transfection of HDAC1 siRNA oligos (FIG. 13B, lane 2) but not the NS-siRNA. Endogenous PSA expression was analyzed in LNCaP cells after transfected with HDAC1-siRNA. As expected, PSA expression was enhanced by transfection of HDAC1-siRNA (FIG. 13C). When SENP1 was cotransfected with HDAC1 siRNA or non-specific control siRNA, a 9.5-fold enhancement of AR-dependent transcription by SENP1 was observed in HDAC1 silenced cells (FIG. 13D). In contrast, non-specific siRNA oligos did not interfere with the SENP1's enhancement of AR-dependent transcription (50-fold) (FIG. 13D). Furthermore, SENP1 mutant had no effect on AR-dependent transcription in both siRNA oligos transfected cells. These data clearly demonstrated that HDAC1 was the main target of SENP1 in its ability to enhance AR-dependent transcription.

Example 21

Silencing of SENP1 Inhibits Cell Proliferation and G1-S Phase Progression

Figure 14:
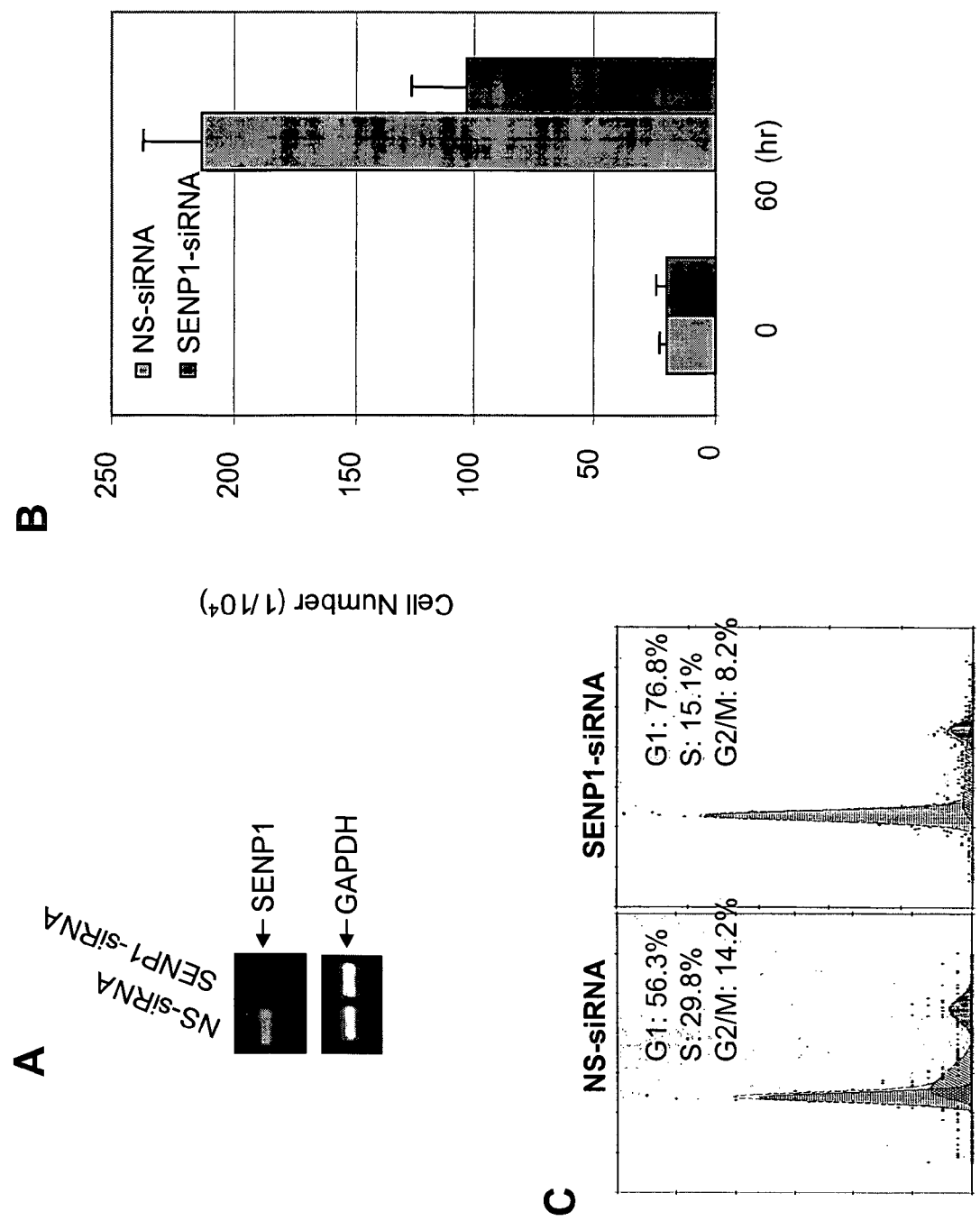
FIG. 14A-14C show that silence of SENP1 inhibits cell growth and G1-S phase progression. PC-3 cells were transfected with non-specific siRNA or SENP1-siRNA. At 60 hr after re-plating the transfected cells, endogenous SENP1 mRNA level (FIG. 14A), cell numbers (FIG. 14B), and cell cycle distribution (FIG. 14C) was determined.

Over-expression of SENP1 in prostate cancer cells could be involved in the regulation of cell proliferation and cell cycle progression, Since PC3 cells expressed high level of endogenous SENP1 (FIG. 1E), it was chosen as a model cells to correlate SENP1 expression and cell proliferation. Endogenous SENP1 mRNA level in PC3 cells was dramatically reduced by specific SENP1 siRNA, but not by non-specific siRNA (FIG. 14A). The reduction in SENP1 mRNA led to a corresponding reduction in the proliferation of PC3 cells (FIG. 14B). To exclude the possibility that reduction in the number of PC3 cells 60 hours after the introduction of SENP1 siRNA was due to cell death, the transfected PC3 cells were examined by trypan blue exclusion assay. SENP1 siRNA did not increase trypan blue-positive PC-3 cells in comparison to non-specific siRNA. Next, it was determined whether SENP1 played a role in cell cycle progression of PC-3 cells by cell cycle analysis. As shown in FIG. 14C, SENP1-silenced PC-3 cells had significantly increased G1 phase and decreased S and G2/M phase, indicating that SENP1 played a role in G1-S transition in PC-3 cells. The slowing of cell proliferation in SENP1-silenced PC-3 cells was due to an alteration in G1-S progression.

Example 22

SENP1 Regulates Cyclin D1 Expression

Figure 15:
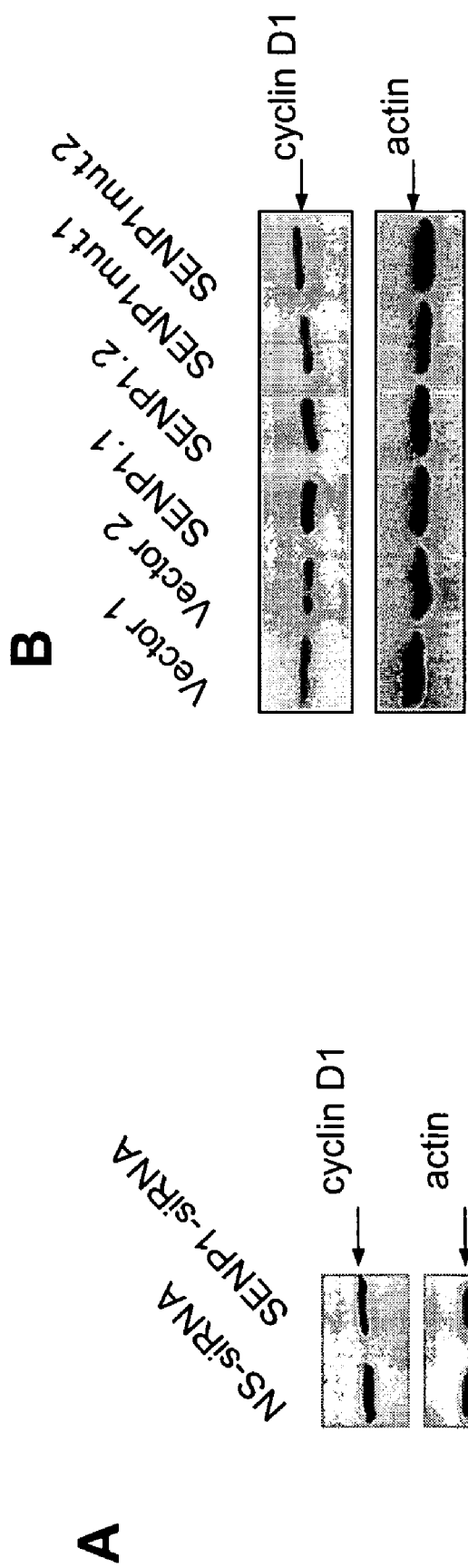
FIG. 15A-15D show that SENP1 regulates cyclin D1 expression.
Figure 15:
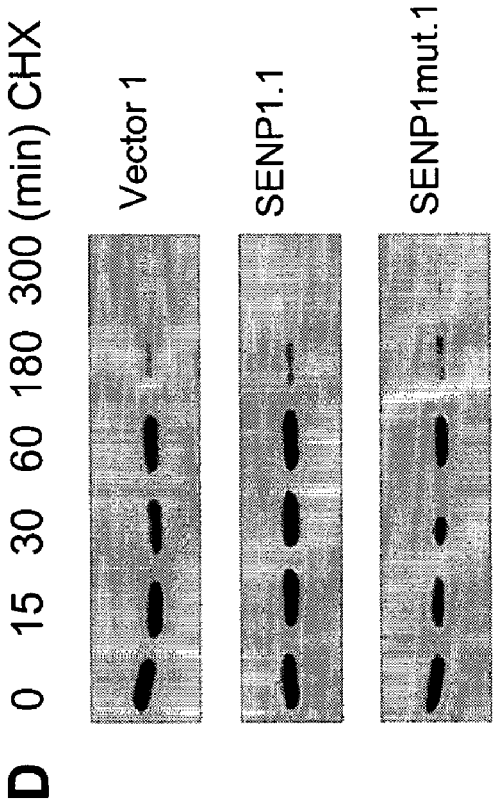
Figure 15:
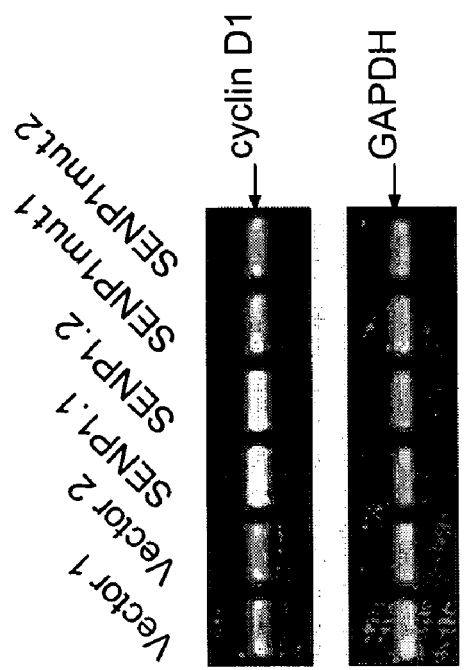

There are numerous cell cycle regulators controlling the cell proliferation and cell cycle progression (Murray, 2004; Harper et al., 2001). Among them, cyclin D1 was predominantly associated with cell growth regulation and G1-S phase transition (Fu et al., 2004; Wang et al., 2004; Stacey 2003). It was reasoned that SENP1 might modulate cell proliferation and cell cycle progression through regulation of cyclin D1 expression. To examine this mechanism, the inventors first determined whether SENP1 played a role in the regulation of cyclin D1 expression in PC-3 cells. PC-3 cells, which were transfected with SENP1 siRNA, had a 50% reduction of cyclin D1 protein level in comparison to the non-specific siRNA-transfected cells, indicating that SENP1 was an important regulator for cyclin D1 expression in PC-3 cells (FIG. 15A). This finding was also confirmed by using SENP1 ectopic expression in LNCaP cells, which expressed a relative low level of endogenous SENP1.

Next, SENP1 and SENP1 mutant stably transfected cells were generated by introducing EGFP-fused SENP1 and SENP1 mutant plasmids or empty vectors into LNCaP cells. After selection by G418 and sorting by flow cytometer, several clones were grown from each stable cell lines. Two clones from each stable cell lines were randomly selected for further analysis. These stably transfected clones expressed GFP, GFP-SENP1, and GFP-SENP1mutant proteins equally. Cyclin D1 protein levels in these clones were determined by immunoblot (FIG. 15B). As expected, SENP1 stably transfected LNCaP cell clones expressed more cyclin D1 protein than vector control cells. Interestingly, SENP1 induction of cyclin D1 expression was dependent on its catalytic activity, as cyclin D1 expression in the SENP1 catalytic mutant cell clones was lower than that of the wild-type clones. These results suggested that SENP1 action on cyclin D1 expression was regulated by the sumoylation pathway.

Since abundance of cyclin D1 in cells can be regulated through transcription and protein stability (Harper et al, 2001), the inventors then asked which mechanism could account for the induction of cyclin D1 by SENP1. The message RNA of cyclin D1 in these clones was examined. As shown in FIG. 15C, semi-quantitative RT-PCR analysis confirmed that mRNA of cyclin D1 was increased in SENP1 cell clones in comparison to vector control and SENP1 mutant cell clones. Next, it was tested whether SENP1 also played a role in the protein stability of cyclin D1. Vector-, SENP1-, and SENP1mut-transcfected cells were treated with cycloheximide, which blocked de novo protein synthesis. Cellular extracts were prepared at different times after cycloheximide addition and the level of cyclin D1 protein was determined by immunoblot analysis. FIG. 15D showed that over-expression of SENP1 did not change the rate of cyclin D1 degradation. Taken together, these results suggested that the increase in cyclin D1 protein in SENP1 over-expressed LNCaP cells was due to transcriptional induction.

Example 23

SENP1 Activates Cyclin D1 Promoter

Figure 16:
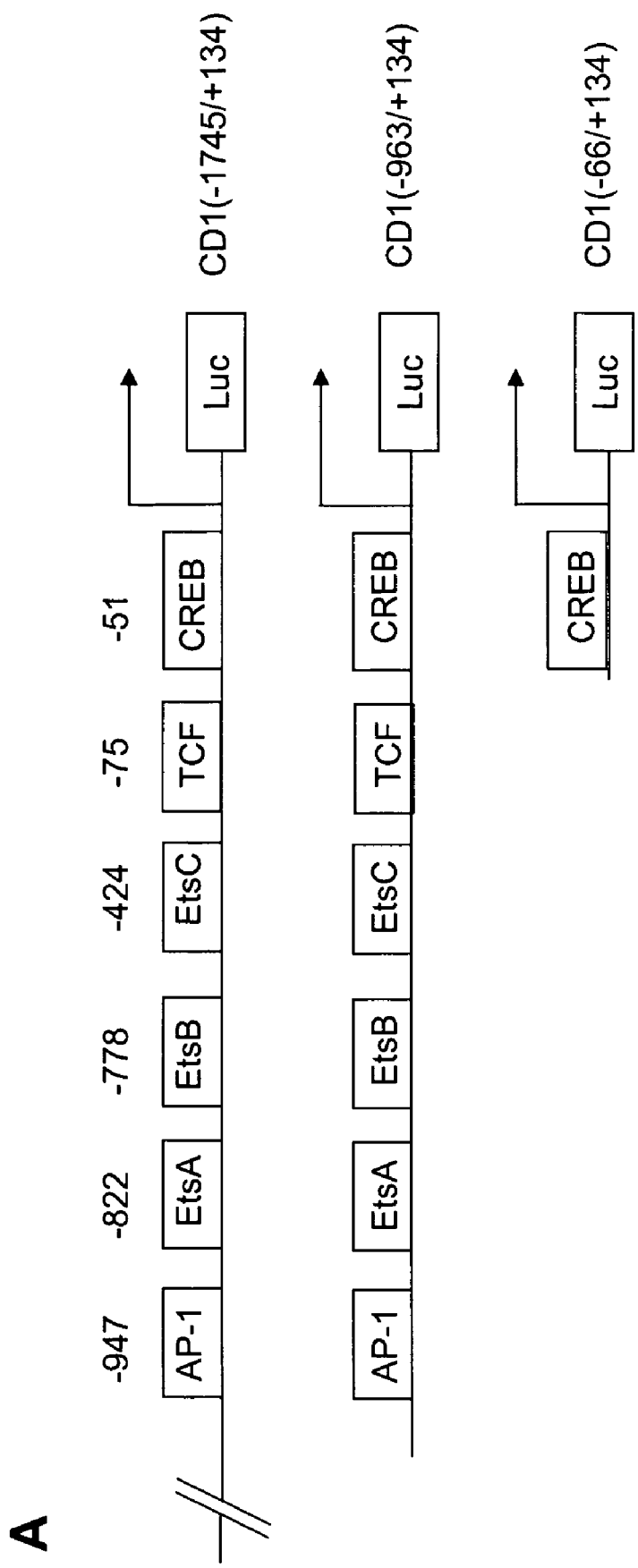
FIG. 16A-16E show that SENP1 activates cyclin D1 promoter.
Figure 16:
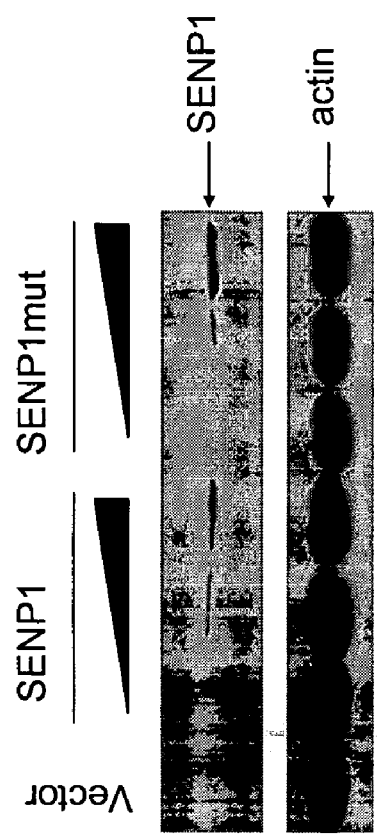
Figure 16:
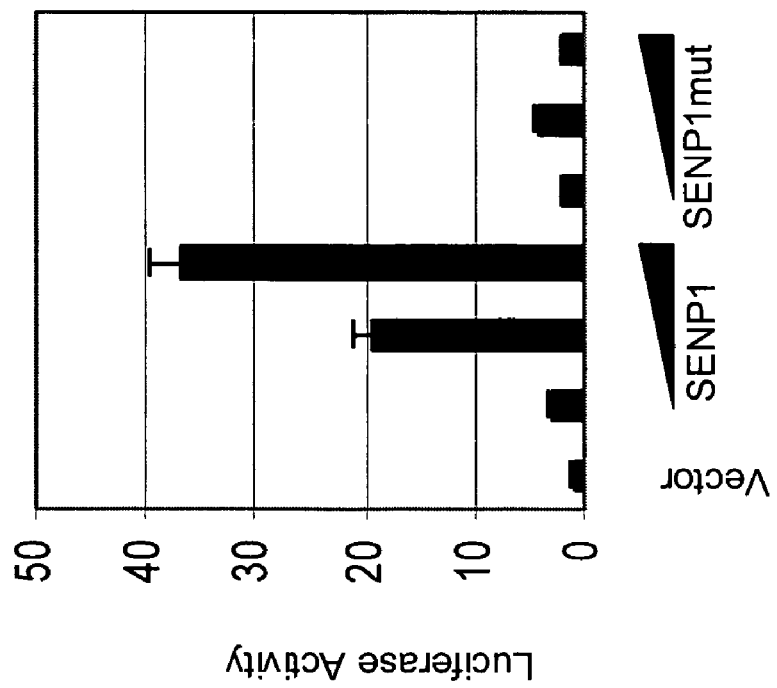
Figure 16:
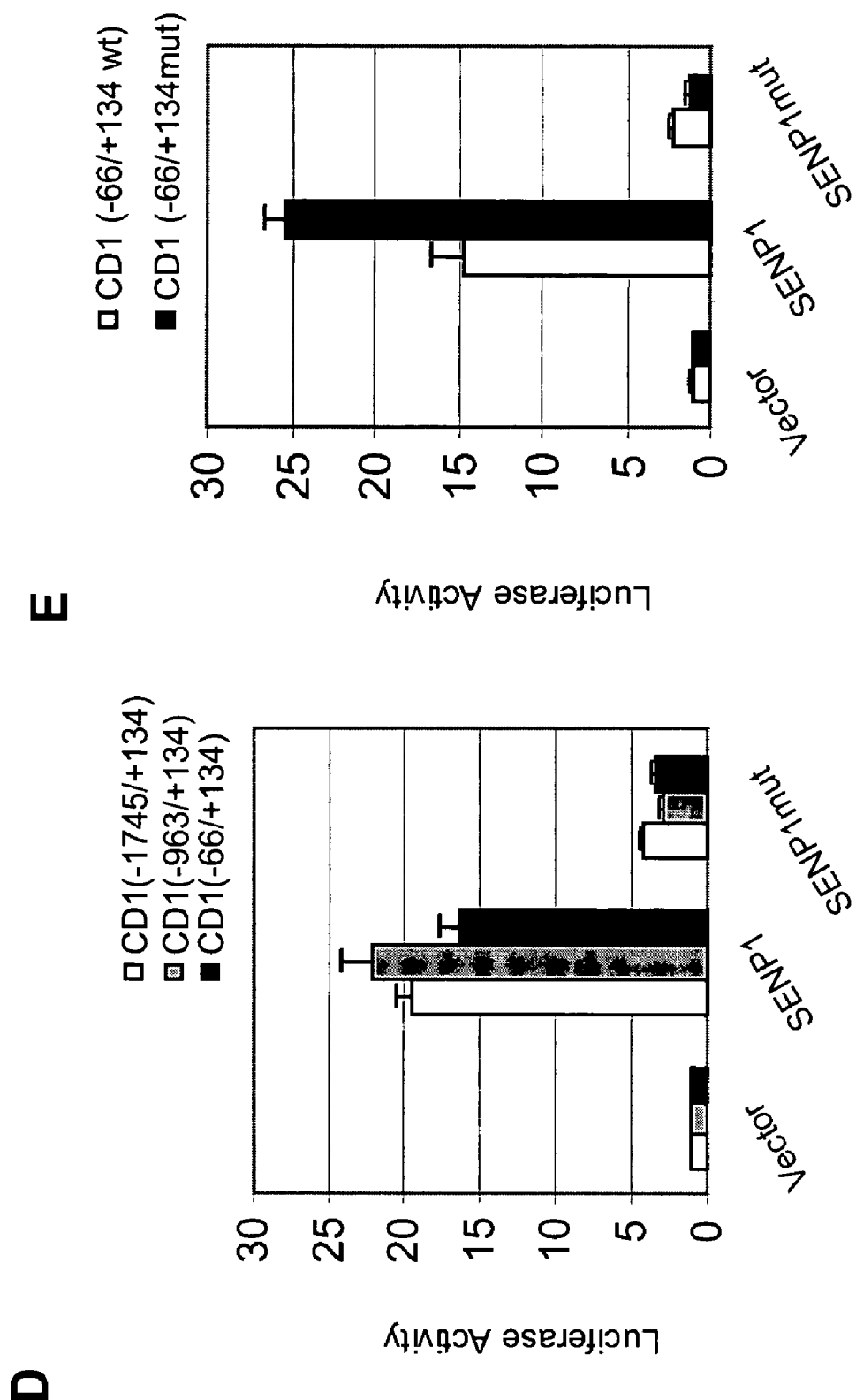

To further confirm the role of SENP1 in cyclin D1 transcription, we performed a cyclin D1 promoter-driven luciferase reporter assay (FIG. 16A) as described by Cheng et al, 2004. CD1 (−1745/+134), which corresponded to the original fragment of cyclin D1 5' sequence cloned from the PRAD1 breakpoint, was transfected into PC-3 cells and its response to SENP1 was measured. FIG. 16B showed that cyclin D1 promoter was strongly induced by SENP1 in a dose-dependent manner.

Also, enhanced transcription was not observed in cells co-transfected with SENP1 mutant, indicating that the SENP1 activation of cyclin D1 promoter is dependent on its catalytic activity. Therefore, it was reasoned that some transcription factors of cyclin D1 promoter, which can be modified by SUMO, might mediate SENP1 action. Cyclin D1 promoter contains multiple regulatory elements (Albanese et al., 1995; Albanese et al., 1999; Albanese et al., 2003). Among these are several elements including the binds sites for transcription factor AP-1, Ets, TCF, and CREB that have been shown previously to be targets of SUMO modification (FIG. 16A) (Comerford et al., 2003; Ihara et al., 2005; Muller et al., 2000; Yang et al., 2003). To determine whether these elements are necessary for SENP1 responsiveness to cyclin D1 promoter, luciferase reporter assay using several mutants of cyclin D1 promoter were preformed. First, two truncated CD1 promoter were tested. One, CD1 (−963/+134), is the minimum 5' sequence that retained responsiveness to Ras (19). Another, CD1 (−66/+134), contained 66 bp of the cyclin D1 promoter. As shown in FIG. 16C, deletion (up to −66) of the cyclin D1 promoter did not affect its response to SENP1, suggesting at least AP-1, Ets, and TCF sites located upstream of −66 bp did not mediate SENP1 action. Next, the inventors also examined the mutants of these sites and confirmed these sites were not required for SENP1 induction. Although there are additional potential TCF sites located downstream of −66 bp of the cyclin D1 promoter, the TCF site located at the −75 bp position is the major one that responds to β-catenin/TCF signal pathway (Tetsu et al., 1999), which was also regulated by SUMO modification (33). The transcription factor CREB, which binds to the CREB site at −51 bp, was also a SUMO-conjugated protein (comerford et al., 2003). To examine whether the CREB was essential for CD1 (−66/+134) response to SENP1, the inventors tested a CD1 (−66/+134) mutant, which contained only two base-pair substitutes at the consensus CREB site, as described (Tetsu et al., 1999). Elimination of the CREB site did not abolished the ability of SENP1 to cyclin D1 promoter (FIG. 16D). Collectively, these results suggested that these sumoylated transcription factors were not essential for activation of the cyclin D1 promoter by SENP1.

Example 24

SENP1 Action on Cyclin D1 Promoter is Mainly Mediated by HDAC1

Figure 17:
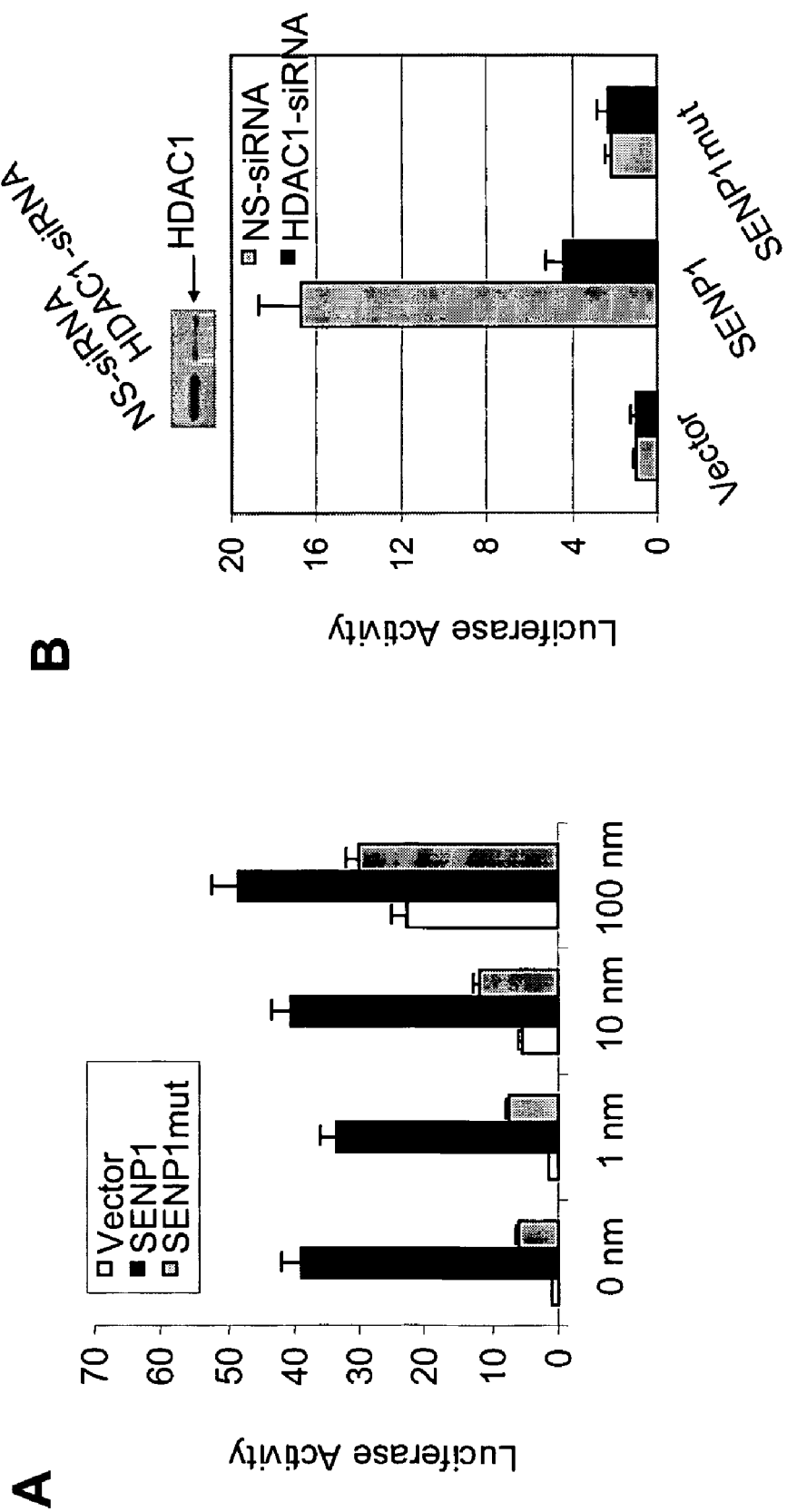
FIG. 17A-17C show that SENP1 action on cyclin D1 promoter is mainly mediated by HDAC1.
Figure 17:
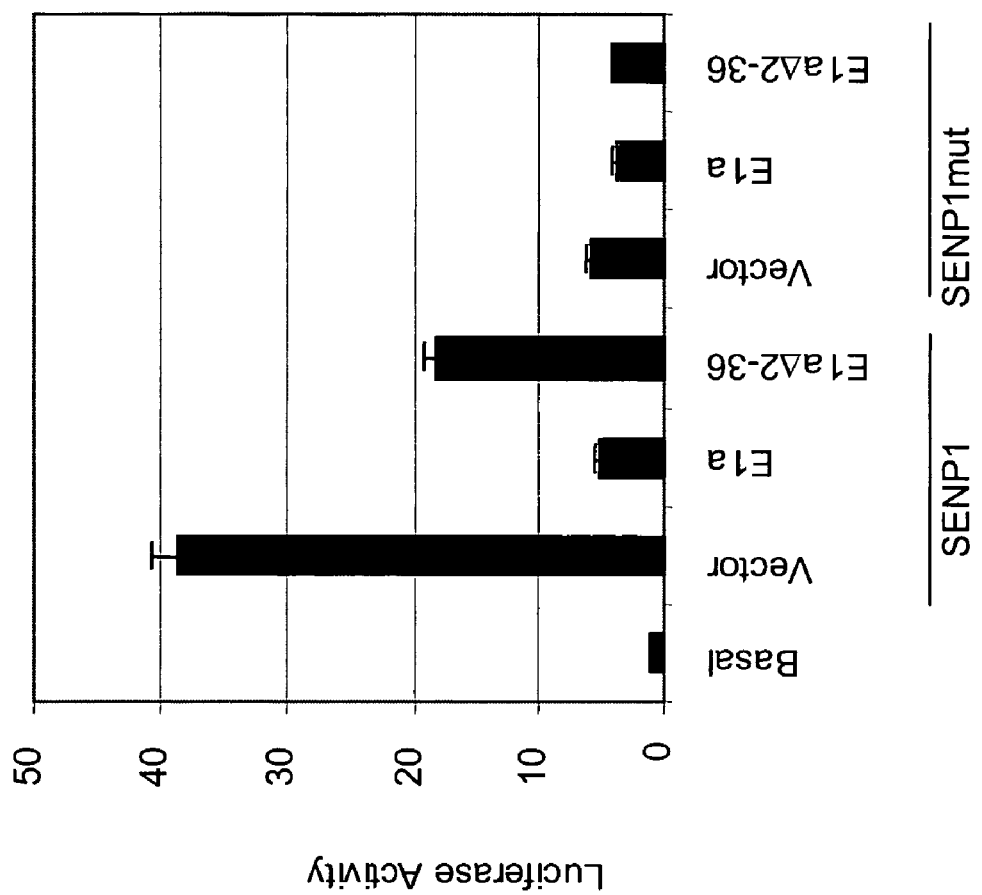

Based on these results, we thought that SENP1 action might be mainly mediated by co-regulators rather than transcription factors. The inventors have reported previously that SENP1 regulated the transcriptional activity of androgen receptor and c-Jun through the desumoylation of co-regulator HDAC1 or p300 respectively (Cheng et al., 2004; Cheng et al., 2005). These co-regulators can modulate chromatin structure and thus affect the gene transcription. To examine whether SENP1 activation of cyclin D1 transcription was mediated by co-regulators, the inventors first used TSA, a HDAC inhibitor, to test HDACs' effect on SENP1 induction of cyclin D1 promoter. For this purpose, PC-3 cells, which were co-transfected with CD1 (−1745/+134) promoter and SENP1 or SENP1 mutant plasmids, were treated with TSA. SENP1 induction of cyclin D1 promoter activity was decreased by TSA in a dose-dependent manner, indicating that HDAC was required for the SENP1 activation of cyclin D1 promoter (FIG. 17A). To further determine the potential role of HDAC1, siRNA approach was used to silence endogenous HDAC1 in PC3 cells. As shown in FIG. 17B, silencing HDAC1 expression dramatically decreased SENP1 induction of cyclin D1 promoter. The inventors also examined whether p300 played a role in SENP1 activation. Although E1a, a p300 inhibitor, almost abolished the promoter activity; E1a 2-36, a p300-binding domain mutant, only recovered p300 SENP1 activity by 38%, suggesting that p300 was not a major target for SENP1 in induction of cyclin D1 transcription (FIG. 17C). These results suggested that HDAC1 mainly mediated SENP1 activation of cyclin D1 promoter.

Example 25

Induction of Cyclin D1 by SENP1 Increases Cell Proliferation

Figure 18:
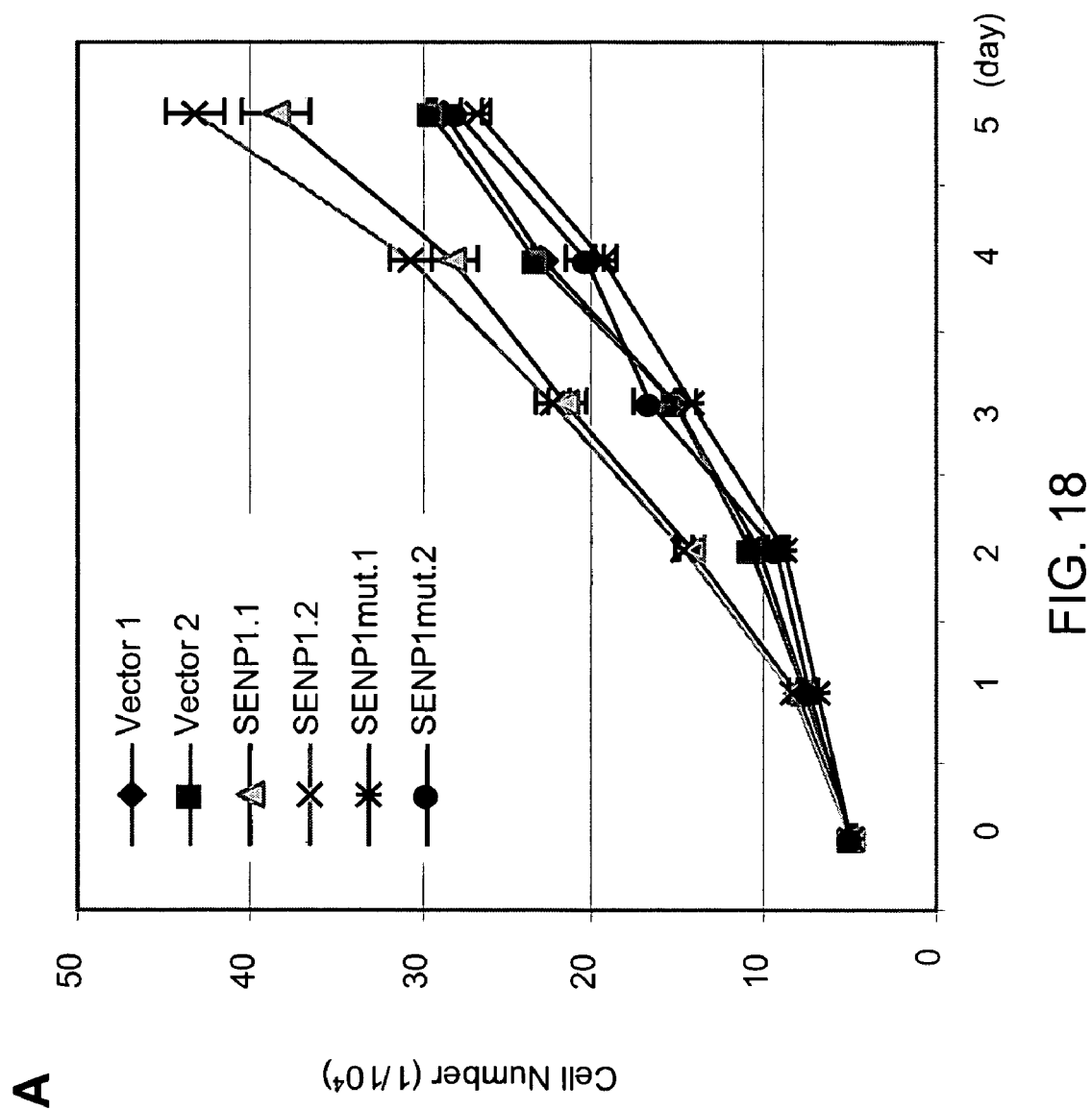
FIG. 18A-18E shows that induction of cyclin D1 by SENP1 increases cell proliferation. Cell growth curves (FIG. 18A) and cell cycle distribution (FIG. 18B) of Vector-, SENP1-, or SENP1mut-LNCaP cell clones were analyzed. The proportion of cells in each phase of the cell cycle was quantitated and shown as the percentage of cells in G1, S, and G2/M phases (FIG. 18C). Data are shown as means of three independent experiments ±SD.
Figure 18:
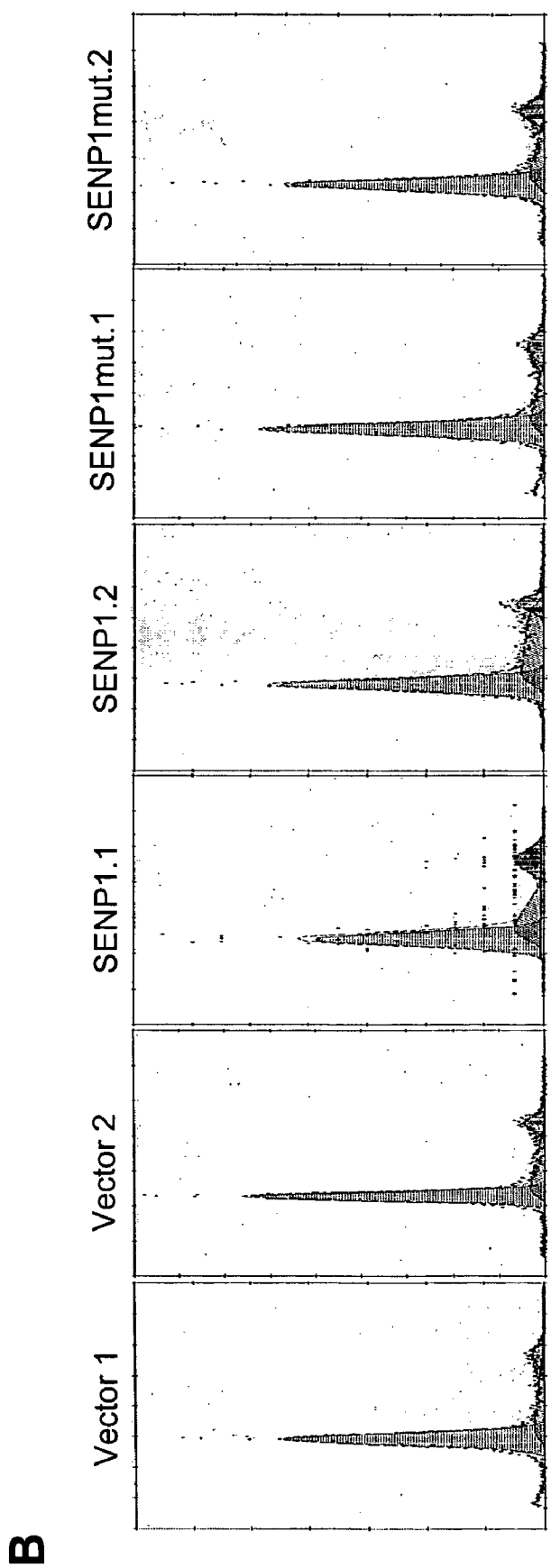
Figure 18:
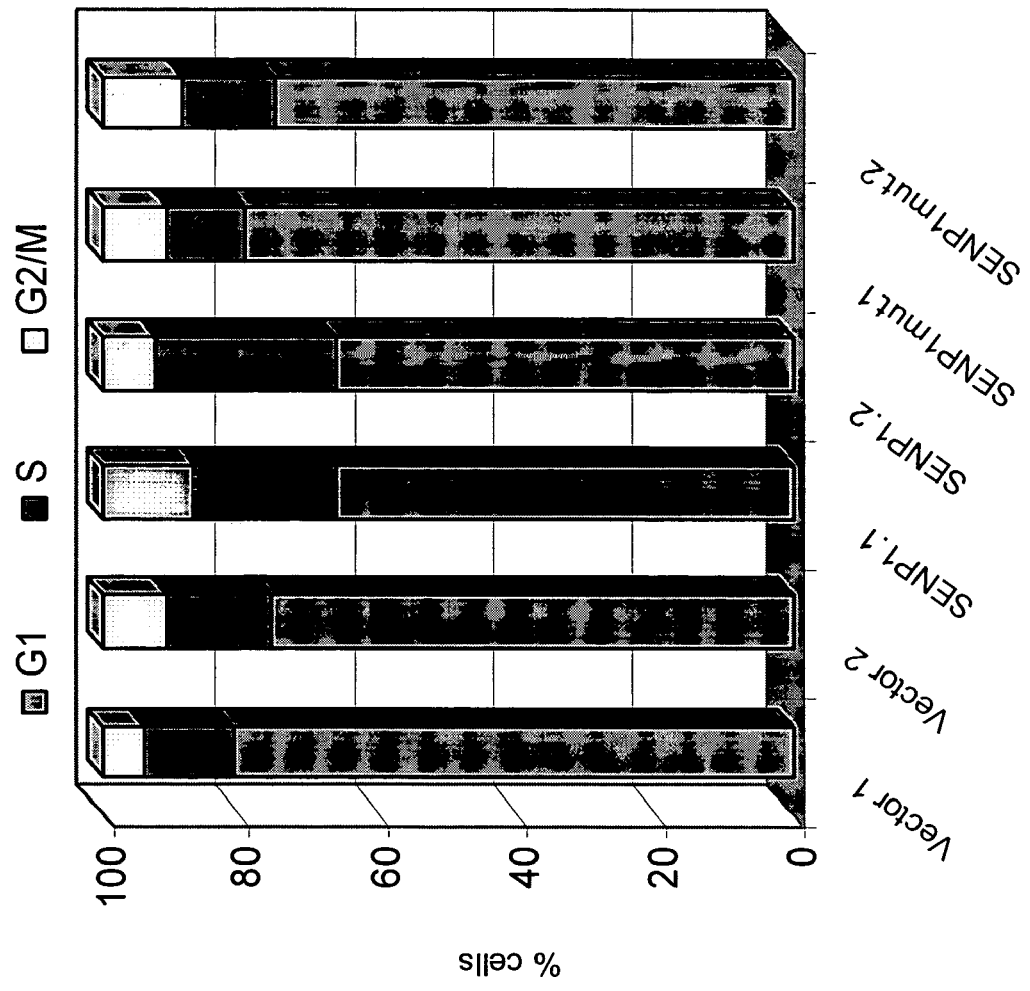
Figure 18:
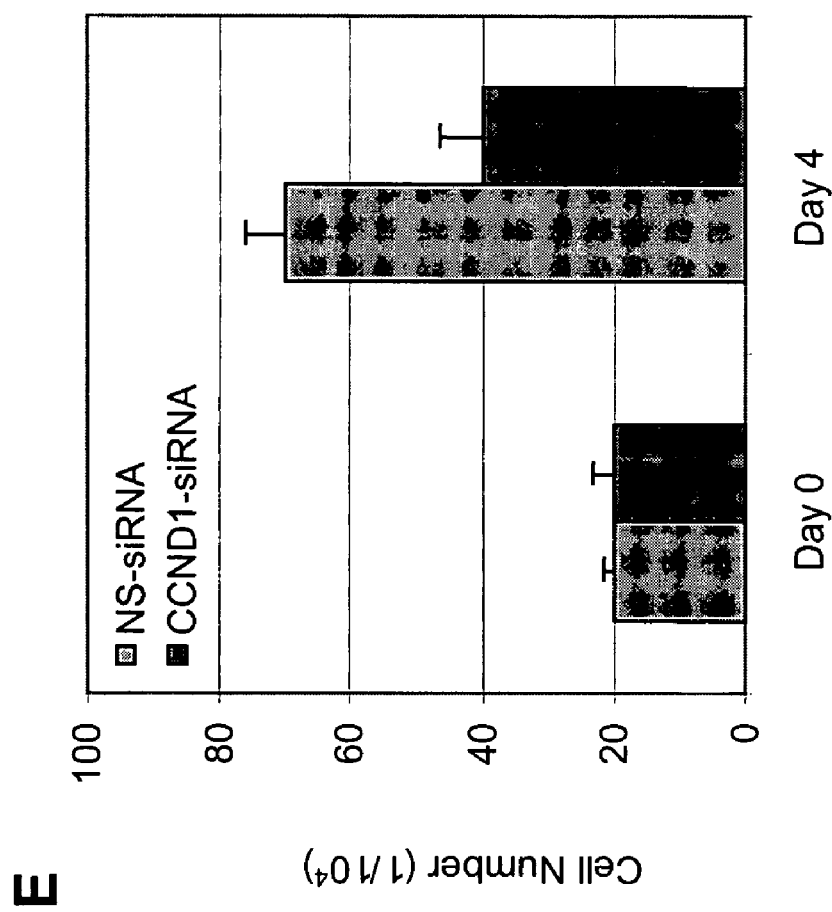

Next, it was examined whether SENP1 over-expression in LNCaP cells would increase cell growth. The cell numbers of two Vector-, SENP1-, or SENP1mut-LNCaP cell clones were counted at different time after plating. As shown in FIG. 18A, cell number of SENP1 cell clones was significantly increased in comparison to vector and SENP1mut cells. The growth increase was also confirmed by flow cytometric assay to evaluate the cell cycle distribution. The G1 phase was decreased in SENP1-LNCaP cells, whereas S phase was significantly increased (FIG. 18B).

To determine whether cyclin D1 was an essential for SENP1's effect on cell proliferation, cyclin D1-specific siRNA was used to silence cyclin D1 expression in SENP1-LNCaP cell. Transfection of cyclin D1 siRNA (CCND1-siRNA) significantly decreased cyclin D1 expression (FIG. 18D) and also greatly decreased the growth of SENP1-LNCaP cells (FIG. 6E). These results suggested that SENP1 induction of cell growth was mainly attributed to the fact that SENP1 up-regulated the expression of cyclin D1.

Example 26

Generating Transgenic Mice that Over-Express SENP1 in the Prostate Gland

Transgenic mice that over-express SENP1 were constructed. A murine SENP1 transgenic vector was constructed by ligating the following gene fragments to the pBluescript (SK+) backbone (Stratagene). The 5' flanking promoter region (−244/−96+−286/+28) of the rat probasin gene was subcloned into the SacI and NotI sites located in MCS. The HA-FLAG tagged murine SENP1 cDNA was subcloned into NotI and SalI sites of the SK+ backbone. The poly (A) tail of the hGH was subcloned into the SalI and ApaI sites of the SK+ multiple cloning site. The rat probasin promoter used in this study was modified according to Sawyers and Matusik (Ellwood-Yen et al., 2003; Zhang et al., 2000). The promoter −244/−96+−286/+28 of the rat probasin gene contains the probasin sequences (−286/+28) plus duplicate androgen response elements (−244/−96) (Zhang et al., 2000). Comparing to the original promoter (−426/+28), the activity of modified rat probasin promoter has a 20-fold increase in transcription activity.

It is envisioned that this modified probasin promoter will drive SENP1 gene to high expression level in the prostate of transgenic mice, thereby enhancing PIN/prostate cancer development.

The completed construct was sequenced and tested for promoter inducibility by androgen in LNCaP cells by transient transfection. After verifying the inducibility of the murine SENP1 constructs by androgen and its biological activity, this construct was microinjected into fertilized C57BL/6 ova and transplanted them into pseudo-pregnant female mice.

Pubs were born following the first microinjection and some were identified to carry the SENP1 transgene by PCR analysis and Southern blot. These are known as the transgenic mouse founders.

These transgenic mouse founders are bred with non-transgenic mice to establish transgenic mouse lines for further analysis. The expression of SENP1 in the transgenic mouse is determined by Western blot analysis using the protein extracts from the mouse prostate at 2 months. Then, anti-HA or anti-Flag in Western blot analysis is used to confirm the expression level of the murine SENP1 transgene in the prostate tissues. The offspring are aged to determine if PIN and/or prostate cancer develops in the male mice that harbor the murine SENP1 transgene.

Example 27

Histological Analysis of the SENP1 Transgenic Mice

These transgenic mice are compared to age-matched wild-type mice, which serve as controls for the assessment of prostate carcinogenesis since prostate carcinoma do not spontaneously occur in mice. Prostates are isolated "en block" from transgenic and wild type mice at 2, 4, 6, 8, 10, 12 weeks, as well at 6, 9, 12, and 16 months. Superficial and deep H&E sections are examined on the same tissue in order to document the presence of PIN, micro-invasion, and invasive adenocarcinoma. A histological grading system is utilized to closely assess the glandular structure of the prostate based on the identification of the following features: 1) normal epithelium: no excess proliferation, small round nuclei, properly formed basement membrane, 2) low-grade PIN: less cytoplasm, nuclei enlargement, slight loss of cellular polarity, 3) high-grade PIN: more cell invasion, atypical nuclei, thinning of the basement membrane, cribriform, and 4) non-differentiated prostate carcinoma: loss of glandular structure, numerous malignant cells.

Example 28

Analysis of Cellular Proliferation, Apoptosis, and Angiogenesis in the SENP1 Transgenic Mice Before the development of PIN, some early pre-cancerous events, such as cell proliferation and reduced apoptosis, may be occurring in SENP1 transgenic mice. To directly demonstrate these early events, proliferation and apoptosis of prostate epithelium from the SENP1 transgenic mice is assessed as early as 2 weeks of age. Proliferation of prostate epithelium is examined by immunostaining the prostate gland for the Ki-67 proliferation antigen. Immunohistochemical procedure is performed in the prostate tissue specimens as described previously (Kamitani et al., 1998). The commercially available Ki-67 antibody (Immunotech, Westbrook, Me.) is employed in this analysis. Apoptosis of the prostate epithelium of the murine SENP1 transgenic mice will also be examined by using the TUNEL assay (Roche) as specified by the manufacturer (Higuchi et al., 1997).

It is envisioned that there will be an increase in cellular proliferation and decrease in cellular apoptosis in the SENP1 over-expressing mice. Another clinical correlate of tumor development is angiogenesis. Thus, angiogenesis is evaluated by changes in the blood vessel density and tortuosity following perfusion with FITC-conjugated lycopersicum esculentum lectin (Rodriguez-Manzaneque et al., 2001). To demonstrate that changes in cellular proliferation, apoptosis, and angiogenesis are dependent on the catalytic activity of SENP1, similar analysis is carried out in transgenic mice that over-express the SENP1 catalytically inactive mutant.

Example 29

The Effect of Hormone Ablation in the SENP1 Transgenic Mice

AR is known to play an important role in prostate cancer initiation and progression (Culig et al., 2003; Gelmann, E. P. 2002; Lee and Chang 2003; Chatterjee 2003). Although the expression of AR is not altered in majority of prostate cancer, the activity of AR is essential for the cancer cell growth (Culig et al., 2003; Gelmann, E. P. 2002; Lee and Chang 2003; Chatterjee 2003; Heinlein et al., 2002; Li et al., 2002). Hence, hormone ablation therapy is the primary treatment for prostate cancer patients with advanced stage disease (Culig et al., 2003, Lee and Chang 2003). Thus, the effect of hormone ablation is studied on the development of PIN and adenocarcinoma and possibly regression of adenocarcinoma in the SENP1 transgenic mice. The timing of castration is decided when the temporal sequence for PIN and adenocarcinoma development in the SENP1 transgenic mice is determined. Mice are castrated that have definite PIN lesion to determine whether PIN will regress with hormone ablation. It is expected that PIN will regress following castration because SENP1 expression in driven by androgen in our SENP1 transgenic mice. Mice are castrated following the development of adenocarcinoma to determine whether adenocarcinoma will regress.

Example 30

The Molecular Signatures in the SENP1 Transgenic Mice

Prostate tissues from SENP1 transgenic mice and non-transgenic littermate controls are isolated at various time points following birth. The timing of sacrifice is decided when the temporal sequence for PIN and adenocarcinoma development in the SENP1 transgenic mice is determined.

Tissues are obtained prior to the development of PIN, after the development of PIN, during PIN/adenocarcinoma transition, following complete development of adenocarcinoma, and following metastasis of adenocarcinoma. Total RNA (30 µg) extracted from these samples is reverse transcribed with an oligo (dT) primer that has a T7 RNA polymerase promoter at the 5' end. Second-strand synthesis is followed by cRNA production incorporating a biotinylated base. The products are hybridized to Affymetrix murine U74Av2 arrays (Santa Clara, Calif.) containing 36,000 full-length mouse genes and EST clusters from the UniGene database (Build 74). After washing and labeling using a fluorescent labeled antibody, chips are scanned by GeneChip Scanner 3000 according to Affymetrix protocols.

The data analysis are performed according to instructions and recommendations provided by Affymetrix. The inventors select candidates with p-value<0.0005 in comparing SENP1 transgenic mice to non-transgenic mice control by t-test and changed in all 6 of 6 SENP1 transgenic mice and non-transgenic mice samples. Then, a fold change is calculated to generate the genes rank lists. Additionally, hierarchical clustering analysis are performed using the genes with significant variation across all samples. The gene lists are generated to distinguish wild type mice from age-matched SENP1 transgenic mice. Gene changes between the different age of mice are analyzed to correlate to the prostate cancer initiation and progression. Furthermore, the gene profiles at different stages of PIN/adenocarcinoma development are compared with exiting dataset of gene profiles of prostate cancers (Ford et al., 2003; et al., 2002; Fu et al., 2003; Hay, 2001; Kretz-Remy et al., 1999; Verger et al., 2003; Yeh et al., 2000).

It is envisioned that the list of gene changes in SENP1 transgenic mice include some genes related to common events like Nkx3.1 decrease, and some specifically related to SENP1 target genes through its desumoylation activity. These genes are analyzed to correlate with the cancer initiation and progression in SENP1 transgenic model.

REFERENCES

All patents and publications mentioned in the specifications are indicative of the levels of those skilled in the art to which the invention pertains. All patents and publications are herein incorporated by reference to the same extent as if each individual publication was specifically and individually indicated to be incorporated by reference.

U.S. Pat. No. 3,817,837
U.S. Pat. No. 3,850,752
U.S. Pat. No. 3,939,350
U.S. Pat. No. 3,996,345
U.S. Pat. No. 4,277,437
U.S. Pat. No. 4,275,149
U.S. Pat. No. 4,366,241
U.S. Pat. No. 4,650,764
U.S. Pat. No. 4,980,289
U.S. Pat. No. 4,988,617
U.S. Pat. No. 5,124,263
U.S. Pat. No. 5,190,856
U.S. Pat. No. 5,324,631
U.S. Pat. No. 5,399,346
U.S. Pat. No. 5,496,699
U.S. Pat. No. 5,633,365
U.S. Pat. No. 5,639,611
U.S. Pat. No. 5,665,549
U.S. Pat. No. 6,201,165
U.S. Pat. No. 6,596,527
U.S. Pat. No. 6,613,308
International Patent Publication No. WO 95/07358
International Patent Publication No. WO 95/28494
International Patent Publication No. WO 99/32619
International Patent Publication No. WO 00/44914
International Patent Publication No. WO 01/36646

International Patent Publication No. WO 01/68836
Albanese et al., J Biol Chem, 270: 23589-23597, 1995.
Albanese et al., J Biol Chem, 274: 34186-34195, 1999.
Albanese et al., Mol Biol Cell, 14: 585-599, 2003.
Amanatullah et al., Methods Enzymol, 333: 116-127, 2001.
Angel et al., Cell 1988; 55:875-885.
Angerer et al., METHODS ENZYMOL., 152: 649-660 (1987)
Arap et al., Cancer Res., 1995; 55(6):1351-1354.
Bachant et al., Mol Cell, 9: 1169-1182, 2002.
Balk, Urology, 60: 132-138; discussion 138-139, 2002.
Barany and Merrifield, The Peptides, 1979; pp. 1-284.
Barany, 1991, Proc. Natl. Acad. Sci. USA 88:189
Barringer et al., 1990, Gene, 89: 117.
Berzal-Herranz et al, Genes Dev. 1992; 6(1):129-34.
Best et al., Mol Cell, 10: 843-855, 2002.
Blackwell et al., Chem Biol. 2001; 8:1167-82.
Blanchard et al., 1996, Biosensors & Bioelectronics 11:687.
Boddy et al., Oncogene 1996; 13:971-982.
Buschmann, T., et al., Cell 2000 101:753-762.
Caldas et al., Nat. Genet., 1994; 8(1):27-32.
Canto et al., Urol Clin North Am 2003; 30 (2):263-77.
Cech et al., Cell. 1987; 27(3 Pt 2):487-96.
Chatterjee, Mol Cell Biochem 2003; 253:89-101.
Chauchereau et al. J. Biol Chem 2003; 14:14.
Chen et al., Oncogene, 16: 1913-1920, 1998.
Cheng et al., Cancer Res., 54(21):5547-5551.
Cheng et al., J Biol Chem, 280: 14492-14498, 2005.
Cheng et al., Mol Cell Biol, 24: 6021-6028, 2004.
Chlenski et al., Prostate 2001; 47 (1):66-75.
Chowrira et al, J Biol. Chem. 1994; 269(41):25856-64.
Chowrira et al., J Biol. Chem. 1993; 268(26):19458-62.
Cleary and Sklar, Proc. Natl. Acad. Sci. USA, 1985; (21): 7439-7443.
Cleary et al., J. Exp. Med., 1986; 164(1):315-320.
Clemons et al., Chem Biol. 2001; 8:1183-95.
Colombo et al., EMBO Rep 2002; 3:1062-1068.
Comerford et al., Proc Natl Acad Sci USA, 100: 986-991, 2003.
Compton, 1991. Nature 350:91.
Courey et al., Cell 1988; 55(5):887-98.
Culig et al., J Urol 2003; 170 (4 Pt 1):1363-9.
Culig et al., Br J Cancer 1998; 78 (8):1004-11.
Culig J Urol 2003; 170:1363-1369.
David et al., J Biol Chem 2002; 277 (26):23658-63.
David et al., J Biol Chem, 277: 23658-23663, 2002.
De Ruijter et al., Biochem J 2003; 370:737-749.
Debes et al., Cancer Res 2002; 62:5632-5636.
DeMarzo, A. M., et al., Lancet 2003; 361:955-964.
Desterro, J. M., et al. Mol Cell 1998; 2:233-239.
Dobson et al., Mol Cell Biol, 25: 4299-4310, 2005.
Drobnjak et al., Clin Cancer Res, 6: 1891-1895, 2000.
Eckert and Kunkel, (1991) PCR METHODS AND APPLICATIONS 1: 17; PCR, eds. McPherson, Quirkes, and Taylor, IRL Press, Oxford.
Ellwood-Yen et al., Cancer Cell 2003; 4:223-238.
Fahy et al., 1992, PCR Methods Appl. 1:25.
Fodor et al., 1991, Science 251:767.
Fodor et al., Science, 1991; 251:767-773.
Ford et al., J Urol 2003; 170:1817-1821.
Forster and Symons, Cell 1987; 49:211-220.
Fu et al., Endocrinology, 145: 5439-5447, 2004.
Fu et al., Mol Cell Biol 2003; 23:8563-8575.
Gall and Pardue Proc. Natl. Acad. Sci., U.S.A., 63: 378-383 (1969).
Gelmann, J Clin Oncol 2002; 20:3001-3015.
Gerster et al., EMBO J. 1990; (5):1635-43.
Giet et al., J. Cell Biol. 2001; 152(4):669-82.
Gill, Genes Dev, 18: 2046-2059, 2004.
Girdwood, D., et al. Mol Cell, 2003; 11:1043-1054.
Gong et al., J Biol Chem, 275: 3355-3359, 2000.
Gostissa, M., et al. Cell, 1999; 18:6462-6471.
Guatelli et al., 1990, Proc. Nat. Acad. Sci. USA, 87: 1874.
Hacia et al., Nature Genetics, 1996; 14:441-447.
Hammond et al., Nat Rev Genet. 2001; 2(2):110-9.
Han et al., Mol Cell Biol 1992; 12:4472-4477.
Han et al., Prostate, 35: 95-101, 1998.
Hang et al., J Biol Chem, 277: 19961-19966, 2002.
Harper et al., Chem Rev, 101: 2511-2526, 2001.
Haseloff and Gerlach, Nature. 1988; 334(6183):585-91.
Hay et al., Philos Trans R Soc Lond B Biol Sci 1999; 354: 1601-1609.
Hay, Mol Cell, 18: 1-12, 2005.
Hay, Trends Biochem Sci 2001; 26:332-333.
Heinlein et al., Endocr Rev 2002; 23:175-200.
Heinlein et al., Endocr Rev, 25: 276-308, 2004.
Hershko and Ciechanover; Annu. Rev. Biochem., 1998; 67:425-479.
Higgins et al., Comput Appl Biosci. 1992; 8:189-91.
Higuchi et al., J. Clin. Invest. 1997; 99:1751-1758.
Hobisch et al., Cancer Res 1998; 58 (20):4640-5.
Hogan et al., Manipulating the Mouse Embryo (Cold Spring Harbor Laboratory, Cold Spring Harbor, N.Y., 1986)
Hope et al., EMBO J. 1987; 6(9):2781-4.
Hulit et al., Biochem Pharmacol, 64: 827-836, 2002.
Hussussian et al., Nat. Genet., 1994; 8(1):15-21.
Ihara et al., Mol Cell Biol, 25: 3506-3518, 2005.
John et al., Nature, 223: 582-587 (1969).
Johnson, Annu Rev Biochem, 73: 355-382, 2004.
Kadoya et al., Mol Cell Biol, 22: 3803-3819, 2002.
Kamb et al., Nat. Genet., 1994; 8(1):23-2.
Kamitani et al., J Biol Chem 1997a; 272:14001-14004.
Kamitani et al., J Biol Chem 1997b; 272:28557-25862.
Kamitani et al., J Biol Chem 1998; 273:26675-26682.
Kaplitt et al., Nat'l Genet., 1994; 8:148-153.
Kerr et al., Br. J. Cancer, 1972; 26(4):239-257.
Khan et al., 1992, Neurosci. Lett. 147:114.
Kim and Cech, Proc. Nat'l Acad. Sci. USA, 1987; 84:8788-8792.
Kim et al., J Biol Chem 2000; 275:14102-14106.
Kirsh et al., Embo J 2002; 21:2682-2691.
Kishi et al., Am J Physiol Endocrinol Metab 2003; 284:E830-840.
Kotaja et al. J. Biol. Chem. 2002. 277:30283-30288.
Kretz-Remy et al., Biochem Cell Biol 1999; 77:299-309.
Kuo et al., Blood, 1993; 82:845.
Kwoh et al., 1989, Proc. Natl. Acad. Sci. USA, 86: 1173.
Lamb et al., Cell, 114: 323-334, 2003.
Landegren et al., 1988. Science, 241: 1077.
Lee and Chang, Cell Mol Life Sci 2003; 60:1613-1622.
Lee et al., Clin Cancer Res 2003; 9 (1):370-6.
Lehembre, F., et al., Onogene 2001; 20:1-9.
Li et al., Am J Pathol 2002; 161:1467-1474.
Li et al., Mol Cell Biol, 20: 2367-2377, 2000.
Li et al., Nature, 398: 246-251, 1999.
Li P et al., Am J Pathol 2002; 161 (4):1467-74.
Li, S. J., et al., Nature 1999; 398:246-251.
Lieber et al., Mol Cell Biol. 1995; 15(1):540-51.
Lin et al., Proc Natl Acad Sci USA, 97: 4262-4266, 2000.
Lin, H. K., et al., Embo J 2002; 21:4037-4048.
Lockhart et al., 1996, Nature Biotech 14:1675.
Lomell et al., 1989. J. Clin Chem., 35:1826.
Ma et al., 1987; 50:137-42.
Mahajan, R. et al., Cell 1997; 88:97-107.

Manila et al., 1991, Nucleic Acids Res. 19: 4967.
Mann et al., Cell 1983; 33:153-159.
Markowitz et al., J. Virol., 1988; 65:1120.
Martin et al., Genes Dev. 1990; (11): 1886-98.
Marx, Science, 307: 836-839, 2005.
Matunis, M. J. et al., J. Cell Biol 1996; 135:1457-1470.
McKenna, N. J., et al., Cell 2002; 108:465-474.
Melchior, Annu Rev Cell Dev Biol, 16: 591-626, 2000.
Mermod et al, Cell 1989; 58(4):741-53.
Merrifield, Science, 1986; 232: 341-347.
Miyamoto et al., Prostate, 61: 332-353, 2004.
Mizokami et al., J Urol 2000; 164 (3 Pt 1):800-5.
Mohler et al., Clin Cancer Res 2004; 10 (2):440-8.
Mossessova et al., Mol Cell, 5: 865-876, 2000.
Muller et al., J Biol Chem 2000; 275:13321-13329
Muller et al., J Biol Chem, 275: 13321-13329, 2000.
Muller-Immergluck et al., EMBO J. 1990; 9(5):1625-34.
Murray, Cell, 116: 221-234, 2004.
Nakamura et al., In: Handbook of Experimental Immunology (4th Ed.). 1987.
Nakashima et al., Clin Cancer Res 1998; 4 (7):1743-8.
NASBA, Cangene, Mississauga, Ontario.
Nawaz, Z., et al., Proc Natl Acad Sci USA 1999; 96:1858-1862.
Negro-Vilar, J. Clin. Endocrinol. Metab., 54(10):3459-62 (1999).
Nishida et al., J Biol Chem 2001; 276:39060-39066.
Nishida et al., Eur J Biochem 2000; 267:6423-6427.
Okamoto et al., Proc Natl Acad Sci USA, 1994; 1(23):11045-11049.
Okura et al., J. Immunol 1996; 157 4277-4281.
Pease et al., 1994, Proc. Natl. Acad. Sci. USA 91:5022.
Pease et al., Proc. Nat'l Acad. Sci. USA, 1994; 91:5022-5026.
Perriman et al., Gene. 1992; 113(2):157-63.
Perrotta and Been, Biochemistry. 1992; 31(1):16-21.
Perry et al., Prostate, 35: 117-124, 1998.
Poukka et al., J Biol Chem 1999; 274:19441-19446.
Poukka et al., Proc Natl Acad Sci USA 2000; 97:14145-14150.
Reinhold-Hurek and Shub, Nature 1992; 357:173-176.
Rodriguez-Manzaneque et al., Proc Natl Acad Sci USA 2001; 98:12485-12490.
Roselli et al., Biol. Reprod. 58: 79-87 (1998)
Ross et al., Mol Cell 2002; 10:831-842.
Rowlands et al., Cell Cycle, 3: 145-148, 2004.
Sachdev et al., Genes Dev, 15: 3088-3103, 2001.
Sadowski et al., Nature 1988; 335(6190):563-4.
Samulski et al., J. Virol., 1987; 61(10):3096-3101
Sarver et al., Science, 1990; 247:1222-1225.
Sawaya et al., J. Invest. Dermatol. 109: 296-300 (1997)
Scanlon et al., Proc. Nat'l Acad. Sci. USA, 1991; 88:10591-10595.
Schena et al., 1996, Genome Res. 6:639
Scherr et al., Urology 2003; 61 (2 Suppl 1):14-24.
Shalon et al., 1996, Genome Research 6:639.
Shang et al., Mol. Cell 2003; 9:601-610.
Shiraishi et al., Urol Int, 61: 90-94, 1998.
Shoemaker et al., Nature Genetics 1996; 14:450-456.
Sioud et al., J Mol. Biol. 1992; 223(4):831-5.
Smith et al., Prostate 2001; 48 (1):47-53.
Stacey et al., Curr Opin Cell Biol, 15: 158-163, 2003.
Stanbrough, M., et al., Proc Natl Acad Sci USA 2001; 98:10823-10828.
Stein et al., Biochem Biophys Res Commun. 2002 291(5): 1119-22.
Stewart and Young, (1984) Solid Phase Peptide Synthesis, 2d. ed., Pierce Chemical Co. Stratford-Perricaudet et al., Bone Marrow Transplant. 1992; 9 Suppl 1:151-2.
Svoboda et al., Biochem Biophys Res Commun. 2001 287 (5):1099-104.
Svoboda et al., Development. 2000; 127(19):4147-56.
Symons, Annu Rev Biochem. 1992; 61:641-71.
Tam et al., J. Am. Chem. Soc., 1983; 105:6442.
Taplin et al., J Cell Biochem, 91: 483-490, 2004.
Taylor et al., J Cell Sci, 115: 1113-1122, 2002.
Temin, In: Gene Transfer, Kucherlapati (ed.) 1986; 149-188.
Tetsu et al., Nature, 398: 422-426, 1999.
Theill et al., Nature. 1989; 342(6252):945-8.
Thompson et al., Nucleic Acids Res. 1994; 22:4673-80.
Thompson et al., Nucleic Acids Res. 1995; 23(12):2259-68.
Tian, S., et al., Biochem J 2002; 367:907-911.
Tojo, M., et al., J Biol Chem 2002; 277:46576-46585.
Tremblay et al., Genes Dev. 2001; 15:833-8.
Tsujimoto and Croce, 1986; Proc Natl Acad Sci USA. 83(14): 5214-5218.
Tsujimoto et al., Science, 1985; 228(4706):1440-1443.
Tussie-Luna, M. I., et al., Proc Natl Acad Sci USA 2002; 99:12807-12812.
Tyagi et al., 1996, Proc. Nat. Acad. Sci. USA, 93: 5395
Ueda et al., J Biol Chem 2002; 277 (9):7076-85.
Urdea, 1994, Bio/Tech. 12:926.
Verger et al., EMBO Rep 2003; 4:137-142.
Vogt, Oncogene 2001; 20:2365-2377.
Walker et al., 1992, Proc. Natl. Acad. Sci. U.S.A. 89:392-396.
Wang et al., Cancer Treat Res, 119: 217-237, 2004.
Wood et al., Proc Natl Acad Sci USA, 100: 3257-3262, 2003.
Wu and Wallace. 1989, Genomics 4:560.
Wu and Wu, Biochemistry 1988; 27:887-892.
Xu et al., Biochem J, 386: 325-330, 2005.
Yamaguchi et al., Mol Cell Biol, 25: 5171-5182, 2005.
Yamamoto et al., Embo J, 22: 2047-2059, 2003.
Yang et al., Biochem Biophys Res Commun 2003; 305 (3): 462-9.
Yang et al., Mol Cell, 12: 63-74, 2003.
Yeh et al., Gene, 248: 1-14, 2000.
Yu et al., Mol. Cell. Bio. 2001; 21:4614-4625.
Yuan and Altman, Science 1994; 263(5151):1269-73.
Yuan et al., (1992) Proc. Nat'l Acad. Sci. USA 89(17):8006-10.
Zhang et al., Cancer Res 2003; 63 (15):4552-60.
Zhang et al., Endocrinology 2000; 141:4698-4710.
Zhou et al., Cancer Lett, 162: 3-17, 2001.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method of diagnosing a hyperproliferative prostate disease in a subject comprising:
   obtaining a sample that is from the prostate of the subject;
   performing an assay on the sample to assess SENP1 expression therein; and comparing the SENP1 expression in the biological sample to the expression of SENP1 in a corresponding normal control, wherein an increase in SENP1 expression relative to the control is indicative of a hyperproliferative prostate disease.

2. The method of claim 1, wherein the subject is a human patient.

3. The method of claim 1, wherein the hyperproliferative disease is a prostate cancer.

4. The method of claim 3, wherein the prostate cancer is prostatic intraepithelial neoplasia, prostatic primary tumor or prostatic metastatic tumor.

5. The method of claim 1, wherein the biological sample is a tissue sample.

6. The method of claim 5, wherein the biological sample comprises a cell.

7. The method of claim 6, wherein the cell is a tumor cell.

8. The method of claim 7, wherein the tumor cell is a prostate tumor cell or a prostatic intraepithelial neoplasia.

9. The method of claim 1, wherein a biological sample is obtained from the subject.

10. The method of claim 1, wherein the hyperproliferative disease is prostatic intraepithelial neoplasia (PIN).

* * * * *

UNITED STATES PATENT AND TRADEMARK OFFICE
CERTIFICATE OF CORRECTION

PATENT NO. : 7,579,152 B2 Page 1 of 1
APPLICATION NO. : 11/214440
DATED : August 25, 2009
INVENTOR(S) : Edward T. H. Yeh It is certified that error appears in the above-identified patent and that said Letters Patent is hereby corrected as shown below:

In column 1, line 17, delete "W81XWH-04-0877" and insert --W81XWH-04-1-0877-- therefor.

Signed and Sealed this

Twenty-seventh Day of October, 2009

David J. Kappos
*Director of the United States Patent and Trademark Office*